(12) United States Patent
Ashkenazi et al.

(10) Patent No.: US 7,629,136 B2
(45) Date of Patent: Dec. 8, 2009

(54) ASSAYS AND METHODS USING BIOMARKERS

(75) Inventors: Avi J. Ashkenazi, San Mateo, CA (US); Klaus W. Wagner, Carmel, IN (US)

(73) Assignee: Genentech, Inc., South San Francisco, CA (US)

(*) Notice: Subject to any disclaimer, the term of this patent is extended or adjusted under 35 U.S.C. 154(b) by 98 days.

(21) Appl. No.: 11/542,318

(22) Filed: Oct. 3, 2006

(65) Prior Publication Data
US 2007/0141023 A1 Jun. 21, 2007

Related U.S. Application Data

(63) Continuation of application No. PCT/US2005/027480, filed on Aug. 3, 2005.

(60) Provisional application No. 60/599,425, filed on Aug. 6, 2004.

(51) Int. Cl.
*G01N 33/53* (2006.01)
*C12Q 1/68* (2006.01)

(52) U.S. Cl. ................ 435/7.23; 435/6; 514/2

(58) Field of Classification Search ........... None
See application file for complete search history.

(56) References Cited

U.S. PATENT DOCUMENTS

| | | | |
|---|---|---|---|
| 5,763,223 | A | 6/1998 | Wiley et al. |
| 6,072,047 | A | 6/2000 | Rauch et al. |
| 6,252,050 | B1 | 6/2001 | Ashkenazi et al. |
| 6,284,236 | B1 | 9/2001 | Wiley et al. |
| 6,313,269 | B1 | 11/2001 | Deen et al. |
| 6,342,383 | B1 | 1/2002 | Perron et al. |
| 6,433,147 | B1 | 8/2002 | Ni et al. |
| 6,461,823 | B1 | 10/2002 | Ni et al. |
| 6,569,642 | B1 | 5/2003 | Rauch et al. |
| 6,642,358 | B1 | 11/2003 | Rauch et al. |
| 2001/0010924 | A1 | 8/2001 | Deen et al. |
| 2002/0048785 | A1 | 4/2002 | Holtzman |
| 2002/0072091 | A1 | 6/2002 | Ni et al. |
| 2002/0098550 | A1 | 7/2002 | Ni et al. |
| 2002/0160446 | A1 | 10/2002 | Holtzman |
| 2003/0125554 | A1 | 7/2003 | Bernard et al. |
| 2003/0133932 | A1 | 7/2003 | Zhou et al. |

FOREIGN PATENT DOCUMENTS

| | | |
|---|---|---|
| EP | 870827 | 3/2004 |
| WO | 97/01633 | 1/1997 |
| WO | 97/25428 | 7/1997 |
| WO | 98/32856 | 7/1998 |
| WO | 98/35986 | 8/1998 |
| WO | 98/41629 | 9/1998 |
| WO | WO 98/51793 | 11/1998 |
| WO | 99/02653 | 1/1999 |
| WO | 99/09165 | 2/1999 |
| WO | 99/11791 | 3/1999 |
| WO | 99/36535 | 7/1999 |
| WO | 99/37684 | 7/1999 |
| WO | WO 00/73349 | 12/2000 |
| WO | 01/00832 A1 | 1/2001 |
| WO | 02/097033 A2 | 12/2002 |
| WO | WO 03/037913 | 5/2003 |
| WO | WO 03/038043 | 5/2003 |
| WO | WO 03/042367 | 5/2003 |

OTHER PUBLICATIONS

Togayachi et al, 1999, Int. J. Cancer vol. 83, pp. 70-79.*
Science, 277:818-821 (1997).*
Ashkenazi et al., "Safety and antitumor activity of recombinant soluble Apo2 ligand" *Journal of Clinical Investigation* 104(2):155-162 (1999).
Ichikawa, K. et al., "Tumoricidal activity of a novel anti-human DR5 monoclonal antibody without hepatocyte cytotoxicity" *Nature Med.* 7(8):954-960 (2001).
Matsumoto et al. *Br. J. Cancer* 86(2):161-167 (2002).
Ugorski et al. *Acta Biochimica Polonica* 49(2):303-311 (2002).
Walczak et al., "Tumoricidal activity of tumor necrosis factor-related apoptosis-including ligand in vivo" *Nature Med.* 5:157-163 (1999).
Akamatsu et al. *Glycoconjugate Journal* 13:1021-1029 (1996).
Asao et al., "Serum alpha (1-3)-L-Fucosyltransferase, Carcinoembryonic Antigen, and Sialyl Lewis X-i Antigen Levels in Lung Cancer" *Cancer* 64(12):2541-2545 (1989).
Ashizawa et al., "The clinical significance of sialyl Lewis antigen expression in the spread of gastric cancer. Flow cytometric DNA analysis" *J. Exp. Clin Cancer Res.* 22(1):91-8 (2003).
Ashkenazi and Dixit., "Death Receptors: Signaling and Modulation." *Science.* 281(5381):1305-1308 (1998).
Ashkenazi et al. *Curr. Opin. Cell Biol.* 11:255-260 (1999).
Ashkenazi et al., "Targeting death and decoy receptors of the tumour-necrosis factor superfamily" *Nature Reviews—Cancer* 2:420-430 (2002).
Azuma et al., "Expression of cell surface Lewis X and Y antigens and FUT4 mRNA is increased in Jurkat cells undergoing apoptosis" *Biochimica et Biophysica Acta* 1672(3):157-163 (2004).
Chuntharapai et al., "Isotype-dependent inhibition of tumor growth in vivo by monoclonal antibodies to death receptor 4" *J. Immunol.* 166:4891-4898 (2001).

(Continued)

*Primary Examiner*—Misook Yu
(74) *Attorney, Agent, or Firm*—Diane L. Marschang

(57) ABSTRACT

Methods and assays examining expression of one or more biomarkers in a mammalian tissue or cell sample are provided. According to the disclosed methods and assays, detection of the expression of one or more such biomarkers is predictive or indicative that the tissue or cell sample will be sensitive to apoptosis-inducing agents such as Apo2L/TRAIL and anti-DR5 agonist antibodies. Certain biomarkers which may be examined include fucosyltransferases, in particular fucosyltransferase 3 (FUT3) and/or fucosyltransferase 6 (FUT6), as well as sialyl Lewis A and/or X antigens. Kits and articles of manufacture are also provided.

13 Claims, 22 Drawing Sheets

OTHER PUBLICATIONS

Degli-Esposti et al., "Cloning and Characterization of TRAIL-R3, a Novel Member of the Emerging TRAIL Receptor Family" *Journal of Experimental Medicine* 186(7) :1165-1170 (1997).

Degli-Esposti et al., "The Novel Receptor TRAIL-R4 Induces NF-κB and Protects against TRAIL-Mediated Apoptosis, yet Retains an Incomplete Death Domain" *Immunity* 7:813-820 (1997).

Dermer, G., "Another anniversry for the war on cancer" *Biotechnology* 12:320 (1994).

Freshney, R. *Culture of Animal Cells: A Manual of Basic Technique*, New York:Alan R. Liss, Inc. pp. 3-4 (1983).

Fujii et al., "Significance of carbohydrate antigen sialyl-Lewis X, sialyl-Lewis A, and possible unknown ligands to adhesion of human urothelial cancer cells to activated endothelium" *Urol Int.* 64(3):129-33 (2000).

Fujiwara et al., "Lung Cancer Cell Line Producing Cytokeratin 19 Fragment and Sialyl Lewis X-i Antigen" *Anticancer Research* 18(2A):1043-46 (1998).

Fukuoka et al., "Increased Expression of Sialyl Lewis(x) Antigen is associated with distant metastasis in lung cancer patients: Immunohistochemical Study on Bronchofiberscopic Biopsy Specimens" *Lung Cancer* 20(2) :109-116 (1998).

Griffith et al., "Functional Analysis of TRAIL Receptors Using Monoclonal Antibodies" *The Journal of Immunology* 162:2597-2605 (1999).

Gura, T., "Systems for identifying new drugs are often faulty" *Science* 278:1041-1042 (Nov. 7, 1997).

Hamanaka et al, "Sialyl Lewis(a) ganglioside in pnacreatic cancer tissue correlates with the serum CA 19-9 level" *Pancreas.* 13(2):160-5 (1996).

Ho et al., "Association of sialyl-Lewis(a) and sialyl-Lewis(x) with MUC-1 apomucin in a pancreatic cancer cell line" *Cancer Research* 55(16):3659-63 (1995).

Hylander et al., "An antibody to DR5 (TRAIL-Receptor 2) suppresses the growth of patient derived gastrointestinal tumors grown in SCID mice." (Abstract, 2d International Congress on Monoclonal Antibodies in Cancers, Aug. 29-Sep. 1, 2002, Banff, Canada).

Idikio, "Sialyl-lewis-X, Gleason grade and stage in non-metastatic human prostate cancer" *Glycoconjugate Journal* 14:875-877 (1997).

Ikeda et al., "Immunohistochemical expression of sialyl Tn, sialyl Lewis a, sialyl Lewis a-b-, and sialyl Lewis x in primary tumor and metastatic lymph nodes in human gastric cancer" *J Surg Oncol.* 62(3):171-6 (1996).

Ikeda et al., "Immunohistochemical expression of sialyl Tn and sialyl Lewis(a) antigens in stromal tissue correlates with peritoneal dissemination in stage IV human gastric cancer" *Eur J Surg Oncol* 21(2):168-75 (1995).

Inoue et al., "Sialyl-Tn, sialyl-Lewis Xi, CA 19-9, CA 125, carcinoembryonic antigen, and tissue polypeptide antigen in differentiating ovarian cancer from benign tumors" *Obstet Gynecol.* 79(3):434-440 (1992).

Ito et al., "Paired tumor marker of soluble E-selectin and its ligand sialyl Lewis A in colorectal cancer" *J. Gastroenterology* 36(12):823-829 (2001).

Izawa et al, "Expression of Sialyl 6-Sulfo Lewis X Is Inversely Correlated with Conventional Sialyl Lewis X Expression in Human Colorectal Cancer" *Cancer Research* 60:1410-1416 (2000).

Koszdin et al. *Biochemical and Biophysical Research Communications* 187(1):152-157 (1992).

Kukowska-Latallo et al. *Genes Dev.* 4(8):1288-1303 (1990).

Kumamoto et al., "Increased Expression of UDP-Galactose Transporter Messenger RNA in Human Colon Cancer Tissues and Its Implication in Synthesis of Thomsen-Freidenreich Antigena nd Sialyl Lewis A/X determinants" *Cancer Research* 61:4620-4627 (2001).

Li et al., "The expression of sialyl Lewis-X antigen in LoVo, HT29 cell lines of colorectal cancer and its correlation with metastatic potential" *Zhonghua Bing Li Xue Za Zhi* 29(2):119-122 (2000).

Locksley et al., "The TNF and TNF Receptor Superfamilies: Integrating Mammalian Biology" *Cell* 104:487-501 (Feb. 23, 2001).

MacFarlane et al. *Journal of Biological Chemistry* 272:25417-25420 (1997).

Marsters et al., "A Novel Receptor for Apo2L/TRAIL Contains a Truncated Death Domain" *Current Biology* 7:1003-1006 (1997).

Matsushita et al., "Selectins induced by interleukin-1/142 on the human liver endothelial cells act as ligands for sialyl Lewis X-expressing human colon cancer cell metastasis" *Cancer Letters* 133:151-160 (1998).

Matsushita et al., "Sialyl-dimeric Lewis-X antigen expressed on mucin-like glycoproteins in colorectal cancer metastases" *Lab Invest* 63(6):780-91 (1990).

Mongkolsapaya et al., "Cutting Edge: Lymphocyte Inhibitor of TRAIL (TNF-Related Apoptosis-Inducing Ligand): A New Receptor Protecting Lymphocytes From the Death Ligand TRAIL" *J. Immunol.* 160(1):3-6 (1998).

MSNBC News Services, "Mixed results on new cancer drug" (online article) pp. 1-4 (Nov. 2000).

Murata et al., "Expression of N-Acetyl Glucose Aminyl Transferase V (GnT-V) Induces Sialyl Lewis X (sLex) Antigen in Human Colorectal Cancer: (RF2)" *Dis Colon Rectum* 44(4):A2-A4 (2001).

Nakagoe et al., "Circulating sialyl Lewis, sialyl Lewis, and sialyl Tn antigens in colorectal cancer patients: multivariate analysis of predictive factors for serum antigen levels" *J. Gastroenterology* 36:166-172 (2000).

Nakagoe et al., "Difference in prognostic value between sialyl Lewis(a) and sialyl Lewis(x) antigen levels in the preoperative serum of gastric cancer patients." *J. Clin Gastroenterol.* 34(4):408-15 (2002).

Nakagoe et al., "Evaluation of sialyl Lewis(a), sialyl Lewis(x), and sialyl Tn antigens expression levels as pedictors of recurrence after curative surgery in node-negative colorectal cancer patients" *J. Exp. Clin Cancer Research* 21(1):107-113 (2002).

Nakagoe et al., "Expression of Lewis(a), sialyl Lewis(a), Lewis(x) and sialyl Lewis(x) antigens as prognostic factors in patients with colorectal cancer" *Canadian Journal of Gastroenterology* 14(9):753-60 (2000).

Nakagoe et al., "Increased expression of sialyl Lewis(x) antigen as a prognostic factor in patients with stage 0, I, and II gastric cancer" *Cancer Letters* 175(2):213-21 (2002).

Nakagoe et al., "Increased expression of sialyl Lewis(x) antigen in penetrating growth type A early gastric cancer" *J. Exp. Clin Cancer Res.* 21(3):363-9 (2002).

Nakagoe et al., "Increased serum level of sialyl Lewis(x) antigen in blood from the tumor drainage vein in patients with non-polypoid growth type of colorectal cancer" *J. Exp. Clin Cancer Res.* 20(1):85-90 (2001).

Nakagoe et al., "Predictive factors for preoperative serum levels of sialyl Lewis(x), sialyl Lewis(a) and sialyl Tn antigens in gastric cancer patients" *Anticancer Research* 22(1A):451-8 (2002).

Nakagoe et al., "Preoperative serum levels of sialyl Lewis(a), sialyl Lewis(x), and sialyl Tn antigens as prognostic markers after curative resection for colorectal cancer" *Cancer Detection & Prevention* 25(3):299-308 (2001).

Nakagoe et al., "Prognostic value of serum sialyl Lewis(a), sialyl Lewis(x) and sialyl Tn antigens in blood from the tumor drainage vein of colorectal cancer patients" *Tumour Biology* 22(2):115-122 (2001).

Nakagoe et al., "Sialyl Lewis(x)—I (SLX) as a tumor-associated carbohydrate antigen in sera in patients with gastric and colorectal cancer-evaluation according to clinicopathological factors" *Gan To Kagaku Ryoho* 16(4 Pt 1):819-25 (1989).

Nakamori et al., "Involvement of Carbohydrate Antigen Sialyl Lewis(x) in colorectal cancer metastasis" *Dis Colon Rectum* 40(4):420-31 (1997).

Narita et al., "Adhesion of Human Breast Cancer Cells to Vascular Endothelium Mediated by Sialyl Lewis & supx; /E-Selectin" *Breast Cancer* 3(1):19-23 (1996).

Ogawa et al., "Glucose-transporter-type-I-gene amplification correlates with sialyl-Lewis-X synthesis and proliferation in lung cancer" *Int. J. Cancer* 74(2):189-192 (1997).

Ogawa et al., "Relation between recurrence and expression of proliferating cell nuclear antigen, sialyl LewisX, and sialyl Lewis(a) in lung cancer" *J. Thorac Cardiovasc Surg.* 108(2):329-336 (1994).

Pan et al., "An Antagonist Decoy Receptor and a Death-Domain Containing Receptor for TRAIL" *Science* 277:815-818 (Aug. 1997).

Pan et al., "The Receptor for the Cytotoxic Ligand TRAIL" *Science* 276:111-113 (Apr. 4, 1997).

Pan et al., "TRUNDD, A New Member of the TRAIL Recepter Family That Antagonizes TRAIL Signalling" *FEBS Letters* 424(1-2):41-45 (1998).

Paulson et al., "Glycosyltransferases" *Journal of Biological Chemistry* 264(30):17615-17618 (Oct. 25, 1989).

Pitti et al., "Induction of Apoptosis by Apo-2 Ligand, a New Member of the Tumor Necrosis Factor Cytokine Family" *Journal of Biological Chemistry* 271:12687-12690 (1996).

Punnoose et al., "O-Glycocsyl Transferases Predict Sentivity in Apomab in Tumor Cell Lines of Epithelial and Non-Epithelial Origin" *AACR Annual Meeting 2009* (Apr. 19, 2009).

Rapoport et al. *Glycobiology* 9:1337-1345 (1999).

Saito et al., "Increased expression of sialyl-Lewis A correlates with poor survival in upper urinary tract urothelial cancer patients." *Anticancer Research* 23(4):3441-3446 (2003).

Sato et al., "The association of sialyl Lewis(a) antigen with the metastatic potential of human colon cancer cells" *Anticancer Research* 17(5A):3505-11 (1997).

Satoh et al., "Elevated Serum Sialyl Lewis X-i Antigen Levels in Non-Small Cell Lung Cancer with Lung Metastasis" *Respiration* 65(4):295-298 (1998).

Satoh et al., "Predictive Value of Preoperative Serum Sialyl Lewis X-i Antigen Levels in Non-Small Cell Lung Cancer" *Anticancer Research* 18(4B):2865-2868 (1998).

Satoh et al., "Serum Sialyl Lewis X-i Antigen Lewis in Non-Small Cell Lung Cancer: Correlation with Distant Metastasis and Survival" *Clin Cancer Research*. 3(4):495-499 (1997).

Schneider et al., "Characterization of Two Receptors for TRAIL" *FEBS Letters* 416:329-334 (1997).

Screaton et al., "TRICK2, A New Alternatively Spliced Receptor that Transduces the Cytotoxic Signal From TRAIL" *Current Biology* 7:693-696 (1997).

Sheridan et al., "Control of TRAIL-Induced Apoptosis by a Family of Signaling and Decoy Receptors" *Science* 277:818-821 (1997).

Shimizu et al., "Sialyl Lewis X-i (SLX) in the bronchoalveolar lavage fluid from patients with lung cancer" *Nihon Kyobu Shikkan Gakkai Zasshi* 30(5):815-820 (1992).

Sikut et al., "Distinct sub-populations of carcinoma-associated MUC1 mucins as detected by the monoclonal antibody 9H8 and antibodies agains the sialyl-Lewis a and sialyl-Lewis x epitopes in the circulation of breast-cancer patients" *Int. J. Cancer* 66(5):617-623 (1996).

Srinivas et al., "E-selectin: sialyl Lewis, a dependent adhesion of colon cancer cells, is inhibited differently by antibodies against E-selectin ligands" *Scan J Immunol* 44(3):197-203 (1996).

Takada et al., "Contribution of Carbohydrate Antigens Sialyl Lewis A and Sialyl Lewis X to Adhesion of Human Cancer Cells to Vascular Endothelium" *Cancer Research* 53:354-361 (1993).

Tanaka et al., "Sialyl Lewis X expression in vascular permeating lesions as a factor for predicting colorectal cancer metastasis" *Hepatogastroenterology* 46(26):875-82 (1999).

Tatsumi et al., "Immunohistochemical expression of the sialyl Lewis x antigen on gastric cancer cells correlates with the presence of liver metastasis" *Clin Exp Metastasis* 16(8):743-50 (1998).

Togayachi et al., "Up-Regulation of Lewis Enzyme (Fuc-TIII) and Plasma-Type α 1,3Fucosyltransferase (Fuc-TVI) Expression Determines The Augmented Expression of Sialyl Lewis X Antigen In Non-Small Cell Lung Cancer" *Int J Cancer* 83(1):70-79 (1999).

Ueoka et al., "A stastical analysis of serum sialyl Lewis X-1 (SLX), CEA, SCC and NSE levels in patients with lung cancer" *Nihon Kyobu Shikkan Gakkai Zasshi* 29(8):1022-1028 (1991).

Wagner et al., "Death-receptor O-glycosylation controls tumor-cell sensitivity to the proapoptotic ligand Apo2L/TRAIL" *Nature Medicine* 13(9):1070-1077 (2007).

Walczak et al., "TRAIL-R2: A Novel Apoptosis-Mediating Receptor for TRAIL" *EMBO Journal* 16(17):5386-5397 (1997).

Wallach, "TNF Ligand and TNF/NGF Receptor Families" *Cytokine Reference*, Academic Press pp. 377-411 (2000).

Wiley et al., "Identification and Characterization of a New Member of the TNF Family that Induces Apoptosis" *Immunity* 3:673-682 (1995).

Wu et al., "KILLER/DR5 is a DNA Damage-Inducible p53-Regulated Death Receptor Gene" *Nature Genetics* 17:141-143 (1997).

Yamada et al., "Increased sialyl Lewis A expression and fucosyltransferase activity with acquisition of a high metastatic capacity in a colon cancer cell line" *Br J Cancer* 76(5):582-7 (1997).

Yamaguchi et al., "Expression of nm23-H1 gene and Sialyl Lewis X antigen in breast cancer" *Oncology* 55(4):357-362 (1998).

Yamanda et al., "Immunohistochemical expression of sialyl-Lewis antigens in lung cancer" *Nippon Rinsho* 53(7):1776-1780 (1995).

Yamashita et al., "Forskolin and phorbol ester have opposite effects on the expression of mucin-associated sialyl-Lewis(a) in pancreatic cancer cells" *Eur J Cancer* 36(1):113-20 (2000).

\* cited by examiner

```
  1  TTTCCTCACTGACTATAAAGAATAGAAGAAGGGCTTCAGTGACCGGCTGCCTGACTTACAGCAGTCAGACTCTGACAGGATC

181 ATGGCTATGATGGAGGTCCAGGGGTCCAGGGGGACCCAGCCTGCTGCTGATCTTCACAGTTCCTGCAGTCTCTGT
   1 MetAlaMetMetGluValGlnGlyProSerLeuGlyProSerLeuGlyGlnThrCysValLeuIleValIlePheThrValLeuLeuGlnSerLeuCys

181 GTGGCTGTAACTTACGTGTACTTTACCAACGAGCTGAAGCAGATGACGAGGTACTCCAAAAGTGGCATTGCTTGTTTCTTAAAGAA
  31 ValAlaValThrTyrValTyrPheThrAsnGluLeuLysGlnMetGlnAspLysPheThrSerLysGlyIleAlaCysPheLeuLysGlu

271 GATGACAGTTATTGGGACCCCAATGACGAAGAGTATGAACAGCCCCTGCTGCAAGTGCAACTCCGTCAGCTCGTTAGAAAG
  61 AspAspSerTyrTrpAspProAsnAspGluGluTyrGluGlnProLeuLeuGlnValLysLeuArgGlnLeuValArgLys

361 ATGATTTTGAGAACCTCTGAGGAAACCATTCTACAGTTCTACAAAGAAAAGCAACAAAATATTCTCCCCTAGTGAGAGAAGAGGTCCNCAG
  91 MetIleLeuArgThrSerGluGluThrIleLeuGlnPheTyrLysGluLysGlnGlnAsnIleSerProLeuValArgGluArgGlyProGln

451 AGAGTAGCAGCTCACATAACTGGGACCAGAAGAAGCAACACATTGTCTTCTCCAAACTCCAAGAATGAAAAGGCTCTGGGCCCGCAAA
 121 ArgValAlaAlaHisIleThrGlyThrArgGlyThrArgGlyArgSerArgArgSerArgSerProAsnSerLysAsnGluLysAlaLeuGlyArgLys

541 ATAAACTCCTGGGAATCATCATCAAGGAGTGGGCATTCATTCCTGAGCAACTTGAGGAATGGTGAACTGGTCATCCATCATGAAAAGGG
 151 IleAsnSerTrpGluSerArgSerGlyHisSerPheLeuSerAsnLeuHisLeuArgAsnGlyGluLeuValIleHisGluLysGly

631 TTTTACTACATCTATTCCCAAACATACTTTCGATTTCAGGAGGAAATAAAAGAAAACAAAAACAAATGGTCAATATTT
 181 PheTyrTyrIleTyrSerGlnThrTyrPheArgPheArgGlnGluGluIleLeuLysGluAsnThrLysAsnAspLysGlnMetValGlnTyrIle

721 TACAAATACACAAGTTATCCTGACCCTATATTGTTGATGAAAAGTGCTAGAAAATAGTTGTTGGTCTAAAGATGCAGAATATGGACTCTAT
 211 TyrLysTyrThrSerTyrProAspProIleLeuLeuMetLysSerAlaArgAsnSerCysTrpSerLysAspAlaGluTyrGlyLeuTyr

811 TCCATCTATCAAGGGGAATATTTGAGCTTAAGGAACTTGAGGAACTTGAGCCAAAATGACACAGATTTTGTTTCTGTAACAAATGACACTTGATAGACATGGACCAT
 241 SerIleTyrGlnGlyIleGlyIlePheGluLeuLysGluAsnAspArgIlePheValSerValThrAsnGluHisLeuIleAspMetAspHis

901 GAAGCCAGTTTTTCGGGGCCTTTTAGTTGAGCTTAAGCTAACTGACCTGGAAAAGAAAAAGCAATAACCTCAAAGTGACTATTCAGTTTTCAGGAT
 271 GluAlaSerPhePheGlyAlaPheLeuValGlyStp

991 GATACACTATGAAGATGTTTCAAAAAAATCTGACCAAAATCTGACCAAAATCAAACAAACAGAAA
```

FIG. 1

```
  1 ATGGCGCCAC CACCAGCTAG AGTACATCTA GGTGCGTTCC TGGCAGTGAC
    TACCGCGGTG GTGGTCGATC TCATGTAGAT CCACGCAAGG ACCGTCACTG
  1 MetAlaProP roProAlaAr gValHisLeu GlyAlaPheL euAlaValTh

51 TCCGAATCCC GGGAGCGCAG CGAGTGGGAC AGAGGCAGCC GCGGCCACAC
    AGGCTTAGGG CCCTCGCGTC GCTCACCCTG TCTCCGTCGG CGCCGGTGTG
    rProAsnPro GlySerAlaA laSerGlyTh rGluAlaAla AlaAlaThrPro

101 CCAGCAAAGT GTGGGGCTCT TCCGCGGGGA GGATTGAACC ACGAGGCGGG
    GGTCGTTTCA CACCCCGAGA AGGCGCCCCT CCTAACTTGG TGCTCCGCCC
 35    SerLysVa lTrpGlySer SerAlaGlyA rgIleGluPr oArgGlyGly

151 GGCCGAGGAG CGCTCCCTAC CTCCATGGGA CAGCACGGAC CCAGTGCCCG
    CCGGCTCCTC GCGAGGGATG GAGGTACCCT GTCGTGCCTG GGTCACGGGC
    GlyArgGlyA laLeuProTh rSerMetGly GlnHisGlyP roSerAlaArg

201 GGCCCGGGCA GGGCGCGCCC CAGGACCCAG GCCGGCGCGG GAAGCCAGCC
    CCGGGCCCGT CCCGCGCGGG GTCCTGGGTC CGGCCGCGCC CTTCGGTCGG
 68   AlaArgAla GlyArgAlaP roGlyProAr gProAlaArg GluAlaSerP

251 CTCGGCTCCG GGTCCACAAG ACCTTCAAGT TTGTCGTCGT CGGGGTCCTG
    GAGCCGAGGC CCAGGTGTTC TGGAAGTTCA AACAGCAGCA GCCCCAGGAC
    roArgLeuAr gValHisLys ThrPheLysP heValValVa lGlyValLeu

301 CTGCAGGTCG TACCTAGCTC AGCTGCAACC ATGATCAATC AATTGGCACA
    GACGTCCAGC ATGGATCGAG TCGACGTTGG TACTAGTTAG TTAACCGTGT
101 LeuGlnValV alProSerSe rAlaAlaThr IleLysLeuH isAspGlnSe

351 AATTGGCACA CAGCAATGGG AACATAGCCC TTTGGGAGAG TTGTGTCCAC
    TTAACCGTGT GTCGTTACCC TTGTATCGGG AAACCCTCTC AACACAGGTG
    rIleGlyThr GlnGlnTrpG luHisSerPr oLeuGlyGlu LeuCysProPro

401 CAGGATCTCA TAGATCAGAA CGTCCTGGAG CCTGTAACCG GTGCACAGAG
    GTCCTAGAGT ATCTAGTCTT GCAGGACCTC GGACATTGGC CACGTGTCTC
135    GlySerHi sArgSerGlu ArgProGlyA laCysAsnAr gCysThrGlu

451 GGTGTGGGTT ACACCAATGC TTCCAACAAT TTGTTTGCTT GCCTCCCATG
    CCACACCCAA TGTGGTTACG AAGGTTGTTA AACAAACGAA CGGAGGGTAC
    GlyValGlyT yrThrAsnAl aSerAsnAsn LeuPheAlaC ysLeuProCys

501 TACAGCTTGT AAATCAGATG AAGAAGAGAG AAGTCCCTGC ACCACGACCA
    ATGTCGAACA TTTAGTCTAC TTCTTCTCTC TTCAGGGACG TGGTGCTGGT
168   ThrAlaCys LysSerAspG luGluGluAr gSerProCys ThrThrThrA

551 GGAACACAGC ATGTCAGTGC AAACCAGGAA CTTTCCGGAA TGACAATTCT
    CCTTGTGTCG TACAGTCACG TTTGGTCCTT GAAAGGCCTT ACTGTTAAGA
    rgAsnThrAl aCysGlnCys LysProGlyT hrPheArgAs nAspAsnSer

601 GCTGAGATGT GCCGGAAGTG CAGCACAGGG TGCCCCAGAG GGATGGTCAA
    CGACTCTACA CGGCCTTCAC GTCGTGTCCC ACGGGGTCTC CCTACCAGTT
201 AlaGluMetC ysArgLysCy sSerThrGly CysProArgG lyMetValLy

651 GGTCAAGGAT TGTACGCCCT GGAGTGACAT CGAGTGTGTC CACAAAGAAT
    CCAGTTCCTA ACATGCGGGA CCTCACTGTA GCTCACACAG GTGTTTCTTA
    sValLysAsp CysThrProT rpSerAspIl eGluCysVal HisLysGluSer
```

*FIG. 2A*

```
701 CAGGCAATGG ACATAATATA TGGGTGATTT TGGTTGTGAC TTTGGTTGTT
    GTCCGTTACC TGTATTATAT ACCCACTAAA ACCAACACTG AAACCAACAA
235    GlyAsnGl yHisAsnIle TrpValIleL euValValTh rLeuValVal

751 CCGTTGCTGT TGGTGGCTGT GCTGATTGTC TGTTGTTGCA TCGGCTCAGG
    GGCAACGACA ACCACCGACA CGACTAACAG ACAACAACGT AGCCGAGTCC
    ProLeuLeuL euValAlaVa lLeuIleVal CysCysCysI leGlySerGly

801 TTGTGGAGGG GACCCCAAGT GCATGGACAG GGTGTGTTTC TGGCGCTTGG
    AACACCTCCC CTGGGGTTCA CGTACCTGTC CCACACAAAG ACCGCGAACC
268    CysGlyGly AspProLysC ysMetAspAr gValCysPhe TrpArgLeuG

851 GTCTCCTACG AGGGCCTGGG GCTGAGGACA ATGCTCACAA CGAGATTCTG
    CAGAGGATGC TCCCGGACCC CGACTCCTGT TACGAGTGTT GCTCTAAGAC
    lyLeuLeuAr gGlyProGly AlaGluAspA snAlaHisAs nGluIleLeu

901 AGCAACGCAG ACTCGCTGTC CACTTTCGTC TCTGAGCAGC AAATGGAAAG
    TCGTTGCGTC TGAGCGACAG GTGAAAGCAG AGACTCGTCG TTTACCTTTC
301 SerAsnAlaA spSerLeuSe rThrPheVal SerGluGlnG lnMetGluSe

951 CCAGGAGCCG GCAGATTTGA CAGGTGTCAC TGTACAGTCC CCAGGGGAGG
    GGTCCTCGGC CGTCTAAACT GTCCACAGT ACATGTCAGG GGTCCCCTCC
    rGlnGluPro AlaAspLeuT hrGlyValTh rValGlnSer ProGlyGluAla

1001 CACAGTGTCT GCTGGGACCG GCAGAAGCTG AAGGGTCTCA GAGGAGGAGG
     GTGTCACAGA CGACCCTGGC CGTCTTCGAC TTCCCAGAGT CTCCTCCTCC
335     GlnCysLe uLeuGlyPro AlaGluAlaG luGlySerGl nArgArgArg

1051 CTGCTGGTTC CAGCAAATGG TGCTGACCCC ACTGAGACTC TGATGCTGTT
     GACGACCAAG GTCGTTTACC ACGACTGGGG TGACTCTGAG ACTACGACAA
     LeuLeuValP roAlaAsnGl yAlaAspPro ThrGluThrL euMetLeuPhe

1101 CTTTGACAAG TTTGCAAACA TCGTGCCCTT TGACTCCTGG GACCAGCTCA
     GAAACTGTTC AAACGTTTGT AGCACGGGAA ACTGAGGACC CTGGTCGAGT
368    PheAspLys PheAlaAsnI leValProPh eAspSerTrp AspGlnLeuM

1151 TGAGGCAGCT GGACCTCACG AAAAATGAGA TCGATGTGGT CAGAGCTGGT
     ACTCCGTCGA CCTGGAGTGC TTTTTACTCT AGCTACACCA GTCTCGACCA
     etArgGlnLe uAspLeuThr LysAsnGluI leAspValVa lArgAlaGly

1201 ACAGCAGGCC CAGGGGATGC CTTGTATGCA ATGCTGATGA AATGGGTCAA
     TGTCGTCCGG GTCCCCTACG GAACATACGT TACGACTACT TTACCCAGTT
401    ThrAlaGlyP roGlyAspAl aLeuTyrAla MetLeuMetL ysTrpValAs

1251 CAAAACTGGA CGGAACGCCT CGATCCACAC CCTGCTGGAT GCCTTGGAGA
     GTTTTGACCT GCCTTGCGGA GCTAGGTGTG GGACGACCTA CGGAACCTCT
     nLysThrGly ArgAsnAlaS erIleHisTh rLeuLeuAsp AlaLeuGluArg

1301 GGATGGAAGA GAGACATGCA AAAGAGAAGA TTCAGGACCT CTTGGTGGAC
     CCTACCTTCT CTCTGTACGT TTTCTCTTCT AAGTCCTGGA GAACCACCTG
435     MetGluGl uArgHisAla LysGluLysI leGlnAspLe uLeuValAsp

1351 TCTGGAAAGT TCATCTACTT AGAAGATGGC ACAGGCTCTG CCGTGTCCTT
     AGACCTTTCA AGTAGATGAA TCTTCTACCG TGTCCGAGAC GGCACAGGAA
     SerGlyLysP heIleTyrLe uGluAspGly ThrGlySerA laValSerLeu

1401 GGAGTGA
     CCTCACT
468  GluOP*
```

*FIG. 2B*

```
  1 MEQRGQNAPAASGARKRHGPGPREARGARPGLRVPKTLVLVVAAVLLLVSAESALITQQD
 61 LAPQQRAAPQQKRSSPSEGLCPPGHHISEDGRDCISCKYGQDYSTHWNDLLFCLRCTRCD
121 SGEVELSPCTTTRNTVCQCEEGTFREEDSPEMCRKCRTGCPRGMVKVGDCTPWSDIECVH
181 KESGIIIGVTVAAVVLIVAVFVCKSLLWKKVLPYLKGICSGGGGDPERVDRSSQRPGAED
241 NVLNEIVSILQPTQVPEQEMEVQEPAEPTGVNMLSPGESEHLLEPAEAERSQRRRLLVPA
301 NEGDPTETLRQCFDDFADLVPFDSWEPLMRKLGLMDNEIKVAKAEAAGHRDTLYTMLIKW
361 VNKTGRDASVHTLLDALETLGERLAKQKIEDHLLSSGKFMYLEGNADSALS
```

FIG. 3A

Met Glu Gln Arg Gly Gln Asn Ala Pro Ala Ala Ser Gly Ala Arg Lys
1           5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65              70                  75                      80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
            245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

*FIG. 3B*

```
Met Glu Val Gln Glu Pro Ala Glu Pro Thr Gly Val Asn Met Leu Ser
    290             295             300
Pro Gly Glu Ser Glu His Leu Leu Glu Pro Ala Glu Ala Glu Arg Ser
305             310             315                 320
Gln Arg Arg Arg Leu Leu Val Pro Ala Asn Glu Gly Asp Pro Thr Glu
                325             330             335
Thr Leu Arg Gln Cys Phe Asp Asp Phe Ala Asp Leu Val Pro Phe Asp
            340             345                 350
Ser Trp Glu Pro Leu Met Arg Lys Leu Gly Leu Met Asp Asn Glu Ile
        355             360             365
Lys Val Ala Lys Ala Glu Ala Ala Gly His Arg Asp Thr Leu Tyr Thr
    370             375             380
Met Leu Ile Lys Trp Val Asn Lys Thr Gly Arg Asp Ala Ser Val His
385             390             395                 400
Thr Leu Leu Asp Ala Leu Glu Thr Leu Gly Glu Arg Leu Ala Lys Gln
            405             410                 415
Lys Ile Glu Asp His Leu Leu Ser Ser Gly Lys Phe Met Tyr Leu Glu
            420             425             430
Gly Asn Ala Asp Ser Ala Met Ser   *
            435         440
```

```
 401 CAGAGGGTGT GGATTACACC AACGCTTCCA ACAATGAACC TTCTTGCTTC CCATGTACAG TTTGTAAATC AGATCAAAAA CATAAAGTT CCTGCACCAT
     GTCTCCCACA CCTAATGTGG TTGCGAAGGT TGTTACTTGG AAGAACGAAG GGTACATGTC AAACATTTAG TCTAGTTTTT GTATTTTCAA GGACGTGGTA
  71        GluGlyVa  lAspTyrThr  AsnAlaSerA  snAsnGluPr  oSerCysPhe  ProCysThrV  alCysLysSe  rAspGlnLys  HisLysSers  erCysThrMet 501 GACCAGAGAC ACAGTGTGTC AGTGTAAAGA AGGCACCTTC CGGAATGAAA ACTCCCCAGA GATGTGCCGG AAGTGTAGCA GGTGCCCTAG TGGGAAGTC
     CTGGTCTCTG TGTCACACAG TCACATTTCT TCCGTGGAAG GCCTTACTTT TGAGGGGTCT CTACACGGCC TTCACATCGT CCACGGATC ACCCCTTCAG
 104        ThrArgAsp  ThrValCysG  lnCysLysGl  uGlyThrPhe  ArgAsnGluA  snSerProGl  uMetCysSerA  rgCysProSe  rGlyGluVal 601 CAAGTCAGTA ATTGTACGTC CTGGGATGAT TTGAAGAATT ATCCAGTGTG TGGTGCCAAT GCCACTGTGG AAACCCCAGC TGCTGAAGAG ACAATGAACA
     GTTCAGTCAT TAACATGCAG GACCCTACTA AACTTCTTAA TAGGTCACAC ACCACGGTTA CGGTGACACC TTTGGGGTCG ACGACTTCTC TGTTACTTGT
 137        GlnValSerA  snCysThrSe  rTrpAspAsp  leuLysAsnT  yrProValCy  sGlyAlaAsn  AlaThrValG  luThrProAl  aAlaGluGlu  ThrMetAsnThr 701 CCAGCCCGGG GACTCCTGCC CCAGCCCAGC GAACACCAGC AAGAGACAAT CCGGGGACTC CTGCCCCAGC TGCTGAAGAG ACAATGACCA CCAGCCCGGG
     GGTCGGGCCC CTGAGGACGG GGTCGGGTCG CTTGTGGTCG TTCTCTGTTA GGCCCCTGAG GACGGGGTCG ACGACTTCTC TGTTACTGGT GGTCGGGCCC
 171        SerProGl  yThrProAla  ProAlaAlaG  luHisGlnGl  nSerAspPro  ProGlyThrP  roAlaProAl  aAlaGluGlu  ThrMetThrT  hrSerProGly 801 GACTCCTGCC CCAGCCCAGC AAGAGACAAT GACCACCAGC CCGGGGACTC CTGCCCCAGC TGCTGAAGAG ACAATGACCA CCAGCCCGGG GACTCCTGCC
     CTGAGGACGG GGTCGGGTCG TTCTCTGTTA CTGGTGGTCG GGCCCCTGAG GACGGGGTCG ACGACTTCTC TGTTACTGGT GGTCGGGCCC CTGAGGACGG
 204        ThrProAla  ProAlaAlaG  luThrThrSer  tThrThrSer  ProGlyThrP  roAlaProAl  aAlaGluGlu  ThrMetThrT  hrSerProGl  yThrProAla 901 TCTTCTCATT ACCTCTCATG CACCATCGTA GGGATCATAG TTCTAATTGT GCTTCTGATT GTGTTTGTTT GAAAGACTTC ACTGTGGAAG AAATTCCTTC
     AGAAGAGTAA TGGAGAGTAC GTGGTAGCAT CCCTAGTATC AAGATTAACA CGAAGACTAA CACAAACAAA CTTTCTGAAG TGACACCTTC TTTAAGGAAG
 237        SerSerHisT  yrLeuSerCy  sThrIleVal  GlyIleIleV  alLeuIleu  lLeuLeuVal  ValPheVal 1001 CTTACCTGAA AGGTTCAGTT TCCAAGTCCA ACTCCCGACCG GGGCGCTGGA CACTCTCTGC CCTGCCTCCC TCTGCCTGTGT TCCCACAGAC AGAAACGCCT
     GAATGGACTT TCCAAGTCAA AGGTTCAGGT TGAGGGCTGG TGAGGGCCGC CCCGGCGACCT GTGAGAGACG GGACGACACA AGGGTGTCTG TCTTTGCGGA 1101 GCCCCTGCCC CAAAAAAAAA AAAAAAAAAA AAAAAAAAAA AAAAAAAAAA AAAAAAAAAA AAAAAAAAAA AAAAAAAAAA
     CGGGGACGGG GTTTTTTTTT TTTTTTTTTT TTTTTTTTTT TTTTTTTTTT TTTTTTTTTT TTTTTTTTTT TTTTTTTTTT
```

FIG. 3D-3

```
  1 CCAACTGCAC CTCGGTTCTA TCGATTGAAT TCCCCGGGGA TCCTCTAGAG ATCCCTCGAC
 61 CTCGACCCAC GCGTCCGGAA CCTTTGCACG CCTTTGCACG CGTCCGGAA CCTTTGCACG CGCACAAACT ACGGGGACGA TTTCTGATTG
121 ATTTTTGGCG CTTTCGATCC ACCCTCCTCC CTTCTCATGG GACTTTGGGG ACAAAGCGTC
                                                   M  G   L  W  G    Q  S  V
181 CCGACCGCCT CGAGCGCTCG AGCAGGGCGC TATCCAGGAG CCAGGACAGC GTCGGGAACC
  1  P  T  A  S   S  A  R    A  G  R    Y  P  G  A    R  T  A    S  G  T
241 AGACCATGGC TCCTGGACCC CAAGATCCTT AAGTTCGTCG TCTTCATCGT CGCGGTTCTG
 29  R  P  W  L    L  D  P    K  I  L    K  F  V  V    F  I  V    A  V  L
301 CTGCCGGTCC GGGTTGACTC TGCCACCATC CCCCGGCAGG ACGAAGTTCC CCAGCAGACA
 49  L  P  V  R    V  D  S    A  T  I    P  R  Q  D    E  V  P    Q  Q  T
361 GTGGCCCCAC AGCAACAGAG GCGCAGCCTC AAGGAGGAGG AGTGTCCAGC AGGATCTCAT
 69  V  A  P  Q    Q  Q  R    R  S  L    K  E  E  E    C  P  A    G  S  H
421 AGATCAGAAT ATACTGGAGC CTGTAACCCG TGCACAGAGG GTGTGGATTA CACCATTGCT
 89  R  S  E  Y    T  G  A    C  N  P    C  T  E  G    V  D  Y    T  I  A
481 TCCAACAATT TGCCTTCTTG CCTGCTATGT ACAGTTTGTA AATCAGGTCA AACAAATAAA
109  S  N  N  L    P  S  C    L  L  C    T  V  C  K    S  G  Q    T  N  K
541 AGTTCCTGTA CCACGACCAG AGACACCGTG TGTCAGTGTG AAAAAGGAAG CTTCCAGGAT
129  S  S  C  T    T  T  R    D  T  V    C  Q  C  E    K  G  S    F  Q  D
601 AAAAACTCCC CTGAGATGTG CCGGACGTGT AGAACAGGGT GTCCCAGAGG GATGGTCAAG
149  K  N  S  P    E  M  C    R  T  C    R  T  G  C    P  R  G    M  V  K
661 GTCAGTAATT GTACGCCCCG GAGTGACATC AAGTGCAAAA ATGAATCAGC TGCCAGTTCC
169  V  S  N  C    T  P  R    S  D  I    K  C  K  N    E  S  A    A  S  S
721 ACTGGGAAAA CCCCAGCAGC GGAGGAGACA GTGACCACCA TCCTGGGGAT GCTTGCCTCT
189  T  G  K  T    P  A  A    E  E  T    V  T  T  I    L  G  M    L  A  S
781 CCCTATCACT ACCTTATCAT CATAGTGGTT TTAGTCATCA TACCTCAAAG GGTTGTGGTT
209  P  Y  H  Y    L  I  I    H  I  V  V    L  V  I    H  L  K  K    V  V  V
841 GGCTTTTCAT GTCGGAAGAA ATTCATTTCT TACCTCAAAG GCATCTGCTC AGGTGGTGGA
229  G  F  S  C    R  K  K    F  I  S    Y  L  K  G    I  C  S    G  G  G
```

FIG. 3E-1

```
 901 GGAGGTCCCG AACGTGTGCA CAGAGTCCTT TTCCGGCGGC GTTCATGTCC TTCACGAGTT
 249  G  G  P     N  V  H     R  V  L     F  R  R  R     S  C  P     S  R  V

961 CCTGGGGCGG AGGACAATGC CCGCAACGAG ACCCTGAGTA ACAGATACTT GCAGCCCACC
 269  P  G  A     D  N  A     R  N  E     T  L  S  N     R  Y  L     Q  P  T

1021 CAGGTCTCTG AGCAGGAAAT CCAAGGTCAG GAGCTGGCAG AGCTAACAGG TGTGACTGTA
1289  Q  V  S     E  Q  E  H    Q  G  Q     E  L  A  E     L  T  G     V  T  V

1081 GAGTYGCCAG AGGAGCCACA GCGTCTGCTG GAACAGGCAG AAGCTGAAGG GTGTCAGAGG
1309  E Xaa P     E  P  Q     R  L  L     E  Q  A  E     A  E  G     C  Q  R

1141 AGGAGGCTGC TGGTTCCAGT GAATGACGCT GACTCCGCTG ACATCAGCAC CTTGCTGGAT
1329  R  R  L     V  P  V     N  D  A     D  S  A  D     I  S  T     L  L  D

1201 GCCTCGGCAA CACTGGAAGA AGGACATGCA AAGGAAACAA TTCAGGACCA ACTGGTGGGC
1349  A  S  A  T    L  E  E     G  H  A     K  E  T  I     Q  D  Q     L  V  G

1261 TCCGAAAAGC TCTTTTATGA AGAAGATGAG GCAGGCTCTG CTACGTCCTG CCTGTGAAAG
1369  S  E  K  L    F  Y  E     E  D  E     A  G  S  A     T  S  C     L

1321 AATCTCTTCA GGAAACCAGA GCTTCCCTCA TTTACCTTTT CTCCTACAAA GGGAAGCAGC

1381 CTGGAAGAAA CAGTCCAGTA CTTGACCCAT GCCCCAACAA ACTCTACTAT CCAATATGGG

1441 GCAGCTTACC AATGGTCCTA ACATCTAACT GAACTTTGTT AACGCACTTG TATGAAATAC

1501 TGCGTGTGAT AAGCAAACGG GAGAAATTTA TATCAGATTC TTGGCTGCAT AGTTATACGA

1561 TTGTGTATTA AGGGTCGTTT TAGGCCACAT GCGGTGGCTC ATGCCTGTAA TCCCAGCACT

1621 TTGATAGGCT GAGGCAGGTG TCCCATCTCA GCTCGGGAGT TTGAGACCAG CCTCATCAAC

1681 ACAGTGAAAC TCCATCTCAA TTTAAAAAGA AAAAAAGTGG TTTTAGGATG TCATTCTTTG

1741 CAGTTCTTCA TCATGAGACA AGTCTTTTTT TCTGCTTCTT ATATTGCAAG CTCCATCTCT

1801 ACTGGTGTGT GCATTTAATG ACATCTAACT ACAGCCACCG CACAGCCACA ATGCTTTGCC

1861 TTATAGTTTT TTAACTTTAG AACGGGATTA TCTTGTTATT ACCTGTATTT TCAGTTTCGG

1921 ATATTTTTGA CTTAATGATG AGATTATCAA GACGTACCCC TATGCTAAGT CATGAGCATA

1981 TGGACTTACG AGGGTTCGAC TTAGAGTTTT GAGCTTTAAG ATAGGATTAT TGGGGCTTA

2041 CCCCCACCTT AATTAGAAGA AACATTTTAT ATTGCTTTAC TA
```

FIG. 3E-2

FUT3
Structure Fucosyltransferase III

```
   1  ATGGATCCCCTGGGTGCAGCCAAGCCACAATGGCCATGGCGCCGCTGTCTGGCCGCACTG
      METAspProLeuGlyAlaAlaLysProGlnTrpProTrpArgArgCysLeuAlaAlaLeu
  61  CTATTTCAGCTGCTGGTGGCTGTGTGTTTCTTCCTACCTGCGTGTGTCCCGAGACGAT
      LeuPheGlnLeuLeuValAlaValCysPhePheSerTyrLeuArgValSerArgAspAsp
 121  GCCACTGGATCCCCTAGGGCTCCCAGTGGGTCCTCCCGACAGGACACCACTCCCACCCGC
      AlaThrGlySerProArgAlaProSerGlySerSerArgGlnAspThrThrProThrArg
 181  CCCACCCTCCTGATCCTGCTATGGACATGGCCTTTCCACATCCCTGTGGCTCTGTCCCGC
      ProThrLeuLeuIleLeuLeuTrpThrTrpProPheHisIleProValAlaLeuSerArg
 241  TGTTCAGAGATGGTGCCCGGCACAGCCGACTGCCACATCACTGCCGACCGCAAGGTGTAC
      CysSerGluMETValProGlyThrAlaAspCysHisIleThrAlaAspArgLysValTyr
 301  CCACAGGCAGACACGGTCATCGTGCACCACTGGGATATCATGTCCAACCCTAAGTCACGC
      ProGlnAlaAspThrValIleValHisHisTrpAspIleMETSerAsnProLysSerArg
 361  CTCCCACCTTCCCCGAGGCCGCAGGGGCAGCGCTGGATCTGGTTCAACTTGGAGCCACCC
      LeuProProSerProArgProGlnGlyGlnArgTrpIleTrpPheAsnLeuGluProPro
 421  CCTAACTGCCAGCACCTGGAAGCCCTGGACAGATACTTCAATCTCACCATGTCCTACCGC
      ProAsnCysGlnHisLeuGluAlaLeuAspArgTyrPheAsnLeuThrMETSerTyrArg
 481  AGCGACTCCGACATCTTCACGCCCTACGGCTGGCTGGAGCCGTGGTCCGGCCAGCCTGCC
      SerAspSerAspIlePheThrProTyrGlyTrpLeuGluProTrpSerGlyGlnProAla
 541  CACCCACCGCTCAACCTCTCGGCCAAGACCGAGCTGGTGGCCTGGGCGGTGTCCAACTGG
      HisProProLeuAsnLeuSerAlaLysThrGluLeuValAlaTrpAlaValSerAsnTrp
 601  AAGCCGGACTCAGCCAGGGTGCGCTACTACCAGAGCCTGCAGGCTCATCTCAAGGTGGAC
      LysProAspSerAlaArgValArgTyrTyrGlnSerLeuGlnAlaHisLeuLysValAsp
 661  GTGTACGGACGCTCCCACAAGCCCCTGCCCAAGGGGACCATGATGGAGACGCTGTCCCGG
      ValTyrGlyArgSerHisLysProLeuProLysGlyThrMETMETGluThrLeuSerArg
 721  TACAAGTTCTACCTGGCCTTCGAGAACTCCTTGCACCCCGACTACATCACCGAGAAGCTG
      TyrLysPheTyrLeuAlaPheGluAsnSerLeuHisProAspTyrIleThrGluLysLeu
 781  TGGAGGAACGCCCTGGAGGCCTGGGCCGTGCCCGTGGTGCTGGGCCCCAGCAGAAGCAAC
      TrpArgAsnAlaLeuGluAlaTrpAlaValProValValLeuGlyProSerArgSerAsn
 841  TACGAGAGGTTCCTGCCACCCGACGCCTTCATCCACGTGGACGACTTCCAGAGCCCCAAG
      TyrGluArgPheLeuProProAspAlaPheIleHisValAspAspPheGlnSerProLys
 901  GACCTGGCCCGGTACCTGCAGGAGCTGGACAAGGACCACGCCCGCTACCTGAGCTACTTT
      AspLeuAlaArgTyrLeuGlnGluLeuAspLysAspHisAlaArgTyrLeuSerTyrPhe
 961  CGCTGGCGGGAGACGCTGCGGCCTCGCTCCTTCAGCTGGGCACTGGATTTCTGCAAGGCC
      ArgTrpArgGluThrLeuArgProArgSerPheSerTrpAlaLeuAspPheCysLysAla
1021  TGCTGGAAACTGCAGCAGGAATCCAGGTACCAGACGGTGCGCAGCATAGCGGCTTGGTTC
      CysTrpLysLeuGlnGlnGluSerArgTyrGlnThrValArgSerIleAlaAlaTrpPhe
1081  ACCTGA
      ThrSTP
```

*FIG. 4*

FUT6
Structure Fucosyltransferase VI

```
  1  ATGGATCCCCTGGGCCCGGCCAAGCCACAGTGGTCGTGGCGCTGCTGTCTGACCACGCTG
     METAspProLeuGlyProAlaLysProGlnTrpSerTrpArgCysCysLeuThrThrLeu
 61  CTGTTTCAGCTGCTGATGGCTGTGTGTTTCTTCTCCTATCTGCGTGTGTCTCAAGACGAT
     LeuPheGlnLeuLeuMETAlaValCysPhePheSerTyrLeuArgValSerGlnAspAsp
121  CCCACTGTGTACCCTAATGGGTCCCGCTTCCCAGACAGCACAGGGACCCCCGCCCACTCC
     ProThrValTyrProAsnGlySerArgPheProAspSerThrGlyThrProAlaHisSer
181  ATCCCCCTGATCCTGCTGTGGACGTGGCCTTTTAACAAACCCATAGCTCTGCCCCGCTGC
     IleProLeuIleLeuLeuTrpThrTrpProPheAsnLysProIleAlaLeuProArgCys
241  TCAGAGATGGTGCCTGGCACGGCTGACTGCAACATCACTGCCGACCGCAAGGTGTATCCA
     SerGluMETValProGlyThrAlaAspCysAsnIleThrAlaAspArgLysValTyrPro
301  CAGGCAGACGCGGTCATCGTGCACCACCGAGAGGTCATGTACAACCCCAGTGCCCAGCTC
     GlnAlaAspAlaValIleValHisHisArgGluValMETTyrAsnProSerAlaGlnLeu
361  CCACGCTCCCCGAGGCGGCAGGGGCAGCGATGGATCTGGTTCAGCATGGAGTCCCCAAGC
     ProArgSerProArgArgGlnGlyGlnArgTrpIleTrpPheSerMETGluSerProSer
421  CACTGCTGGCAGCTGAAAGCCATGGACGGATACTTCAATCTCACCATGTCCTACCGCAGC
     HisCysTrpGlnLeuLysAlaMETAspGlyTyrPheAsnLeuThrMETSerTyrArgSer
481  GACTCCGACATCTTCACGCCCTACGGCTGGCTGGAGCCGTGGTCCGGCCAGCCTGCCCAC
     AspSerAspIlePheThrProTyrGlyTrpLeuGluProTrpSerGlyGlnProAlaHis
541  CCACCGCTCAACCTCTCGGCCAAGACCGAGCTGGTGGCCTGGGCAGTGTCCAACTGGGGG
     ProProLeuAsnLeuSerAlaLysThrGluLeuValAlaTrpAlaValSerAsnTrpGly
601  CCAAACTCCGCCAGGGTGCGCTACTACCAGAGCCTGCAGGCCCATCTCAAGGTGGACGTG
     ProAsnSerAlaArgValArgTyrTyrGlnSerLeuGlnAlaHisLeuLysValAspVal
661  TACGGACGCTCCCACAAGCCCCTGCCCCAGGGAACCATGATGGAGACGCTGTCCCGGTAC
     TyrGlyArgSerHisLysProLeuProGlnGlyThrMETMETGluThrLeuSerArgTyr
721  AAGTTCTATCTGGCCTTCGAGAACTCCTTGCACCCCGACTACATCACCGAGAAGCTGTGG
     LysPheTyrLeuAlaPheGluAsnSerLeuHisProAspTyrIleThrGluLysLeuTrp
781  AGGAACGCCCTGGAGGCCTGGGCCGTGCCCGTGGTGCTGGGCCCCAGCAGAAGCAACTAC
     ArgAsnAlaLeuGluAlaTrpAlaValProValValLeuGlyProSerArgSerAsnTyr
841  GAGAGGTTCCTGCCACCCGACGCCTTCATCCACGTGGACGACTTCCAGAGCCCCAAGGAC
     GluArgPheLeuProProAspAlaPheIleHisValAspAspPheGlnSerProLysAsp
901  CTGGCCCGGTACCTGCAGGAGCTGGACAAGGACCACGCCCGCTACCTGAGCTACTTTCGC
     LeuAlaArgTyrLeuGlnGluLeuAspLysAspHisAlaArgTyrLeuSerTyrPheArg
961  TGGCGGGAGACGCTGCGGCCTCGCTCCTTCAGCTGGGCACTCGCTTTCTGCAAGGCCTGC
     TrpArgGluThrLeuArgProArgSerPheSerTrpAlaLeuAlaPheCysLysAlaCys
1021 TGGAAACTGCAGGAGGAATCCAGGTACCAGACACGCGGCATAGCGGCTTGGTTCACCTGA
     TrpLysLeuGlnGluGluSerArgTyrGlnThrArgGlyIleAlaAlaTrpPheThrSTP
```

FIG. 5

| | Cell Line | Apo2L 0.5% FBS MTT Mean | STD | Apo2L 10% FBS MTT Mean | STD | DR5 mAb+XL 0.5% FBS MTT Mean | STD | DR5 mAb+10% FBS MTT Mean | STD | FUT3 | FUT6 | sialyl Lewis A | sialyl Lewis X |
|---|---|---|---|---|---|---|---|---|---|---|---|---|---|
| 1 | COLO 205 | 10.4 | 3.3 | 7.5 | 0.3 | 122.0 | 3.8 | 140.7 | | 3268.5 | 53507.2 | 783.6 | 326.7 |
| 2 | COLO 201 | 125.7 | 47.5 | 11.6 | 3.0 | 156.2 | 37.0 | 108.6 | | 1799.3 | 1994.9 | 1261.1 | 105.7 |
| 3 | COLO-206F | 40.2 | 4.2 | 17.9 | | 166.4 | 0.3 | 192.2 | | 417.5 | 195.3 | 1377.3 | 9.0 |
| 4 | SW948 | 27.6 | 21.0 | 19.1 | 12.7 | 181.3 | 102.4 | 202.5 | | 1256.9 | 1239.3 | 13.3 | 456.9 |
| 5 | HCT-15 | 45.9 | 24.3 | 510.6 | 692.0 | 136.3 | 12.1 | 268.5 | 127.5 | 90.1 | 137.7 | 7.3 | 10.5 |
| 6 | DLD-1 | 105.8 | 61.6 | 1000.0 | | 184.7 | 25.9 | 320.3 | | 147.2 | 86.1 | 460.3 | 7.0 |
| 7 | LS1034 | 97.7 | 60.6 | 1000.0 | | 59.1 | 19.0 | 338.4 | | 361.4 | 16799.0 | 530.0 | 153.7 |
| 8 | CL-40 | 847.8 | 215.3 | 1000.0 | | 379.0 | 74.5 | 435.8 | | 1275.6 | 11073.8 | 506.4 | 52.1 |
| 9 | COLO-678 | 1000.0 | 0.0 | 1000.0 | 0.0 | 107.3 | 14.7 | 132.5 | | 50.7 | 40.7 | 148.9 | 14.2 |
| 10 | SW403 | 1000.0 | 0.0 | 1000.0 | 0.0 | 201.0 | 62.2 | 300.0 | | 2033.9 | 39360.7 | 251.2 | 281.9 |
| 11 | LS 180 | 1000.0 | 0.0 | 1000.0 | 0.0 | 343.7 | 34.9 | 376.8 | 3.7 | 2076.9 | 57960.7 | 26.8 | 390.4 |
| 12 | SK-CO-1 | 814.2 | 371.6 | 1000.0 | 0.0 | 311.6 | 103.4 | 699.9 | 424.5 | 443.6 | 333.2 | 7.3 | 17.6 |
| 13 | HCT 116 | 347.6 | 438.2 | 1000.0 | 0.0 | 999.7 | 0.7 | 1000.0 | 0.0 | 42.6 | 40.7 | 1.4 | 2.1 |
| 14 | RKO-AS45-1 | 819.2 | 361.6 | 1000.0 | 0.0 | 552.2 | 517.1 | 1000.0 | 0.0 | 0.3 | 3.5 | 3.3 | 7.0 |
| 15 | SW480 | 569.6 | 497.0 | 1000.0 | 0.0 | 615.3 | 392.4 | 1000.0 | 0.0 | 0.3 | 6.3 | 6.6 | 5.1 |
| 16 | LoVo | 1000.0 | 0.0 | 1000.0 | 0.0 | 477.8 | 356.2 | 1000.0 | | 4.4 | 5.8 | 5.6 | 6.1 |
| 17 | SW620 | 1000.0 | 0.0 | 1000.0 | 0.0 | 651.5 | 412.9 | 1000.0 | 0.0 | 0.5 | 6.5 | 15.4 | 6.7 |
| 18 | RKO | 1000.0 | 0.0 | 1000.0 | 0.0 | 857.2 | 285.7 | 1000.0 | 0.0 | 0.1 | 0.6 | 4.5 | 4.9 |
| 19 | CX-1 | 1000.0 | 0.0 | 1000.0 | 0.0 | 902.2 | 195.6 | 1000.0 | 0.0 | 30.7 | 162.1 | 18.3 | 27.4 |
| 20 | HT-29 | 1000.0 | 0.0 | 1000.0 | 0.0 | 1000.0 | 0.0 | 1000.0 | | 63.8 | 12.8 | 5.0 | 28.8 |
| 21 | KM12 | 1000.0 | 0.0 | 1000.0 | 0.0 | 1000.0 | 0.0 | 1000.0 | | 13.4 | 28.3 | 7.0 | 6.5 |
| 22 | COLO 320HSR | 1000.0 | 0.0 | 1000.0 | 0.0 | 1000.0 | 0.0 | 1000.0 | | 0.9 | 0.7 | 3.8 | 4.1 |
| 23 | COLO 320DM | 1000.0 | 0.0 | 1000.0 | 0.0 | 1000.0 | 0.0 | 1000.0 | | 1.1 | 0.6 | 5.2 | 6.4 |
| 24 | SW1116 | 1000.0 | 0.0 | 1000.0 | 0.0 | 1000.0 | 0.0 | 1000.0 | 0.0 | 291.9 | 22176.9 | 386.0 | 577.9 |
| 25 | SW837 | 1000.0 | 0.0 | 1000.0 | 0.0 | 1000.0 | 0.0 | 1000.0 | | 65.2 | 9.1 | 7.2 | 12.5 |
| 26 | Caco-2 | 1000.0 | 0.0 | 1000.0 | 0.0 | 1000.0 | 0.0 | 1000.0 | | 3.0 | 149.7 | 5.4 | 8.9 |
| 27 | HCT-8 | 1000.0 | 0.0 | 1000.0 | 0.0 | 1000.0 | 0.0 | 1000.0 | | 3.2 | 6.8 | 1.3 | 3.9 |
| 28 | SW1417 | 1000.0 | 0.0 | 1000.0 | 0.0 | 1000.0 | 0.0 | 1000.0 | | 48.7 | 233.0 | 21.2 | 9.8 |

FIG. 6

Fisher's Exact Test
FUTIII/sialyl-Lewis A/X versus DR5 mAb

| Fisher's Exact Test | FUT3 | YES | NO | |
|---|---|---|---|---|
| DR5 mAb | SENS | 9 | 2 | 11 |
| | RES | 2 | 15 | 17 |
| | | 11 | 17 | 28 | p-value = 0.00035707

| Fisher's Exact Test | sLA/X | YES | NO | |
|---|---|---|---|---|
| DR5 mAb | SENS | 10 | 1 | 11 |
| | RES | 1 | 16 | 17 |
| | | 11 | 17 | 28 | p-value = 0.00000875

Statistically significant association between FUTIII and sialyl Lewis A/X expression and DR5 mAb sensitivity.

Test Set:

| Fisher's Exact Test | FUT3 | YES | NO | |
|---|---|---|---|---|
| DR5 mAb | SENS | 4 | 2 | 6 |
| | RES | 2 | 10 | 12 |
| | | 6 | 12 | 18 | p-value = 0.05726136

| Fisher's Exact Test | sLA/X | YES | NO | |
|---|---|---|---|---|
| DR5 mAb | SENS | 5 | 1 | 6 |
| | RES | 1 | 11 | 12 |
| | | 6 | 12 | 18 | p-value = 0.00393234

*FIG. 9B*

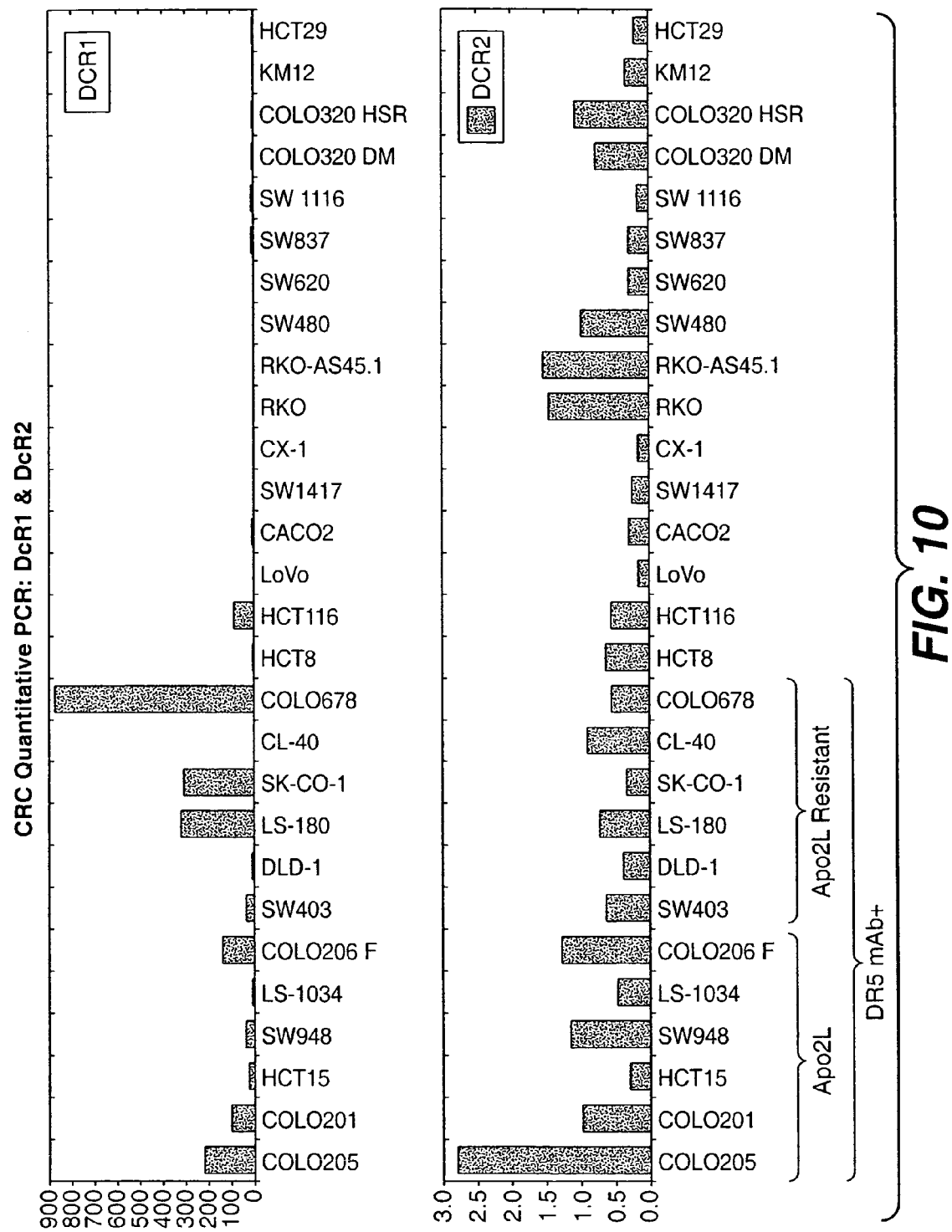

IHC Data on CRC Cell Lines
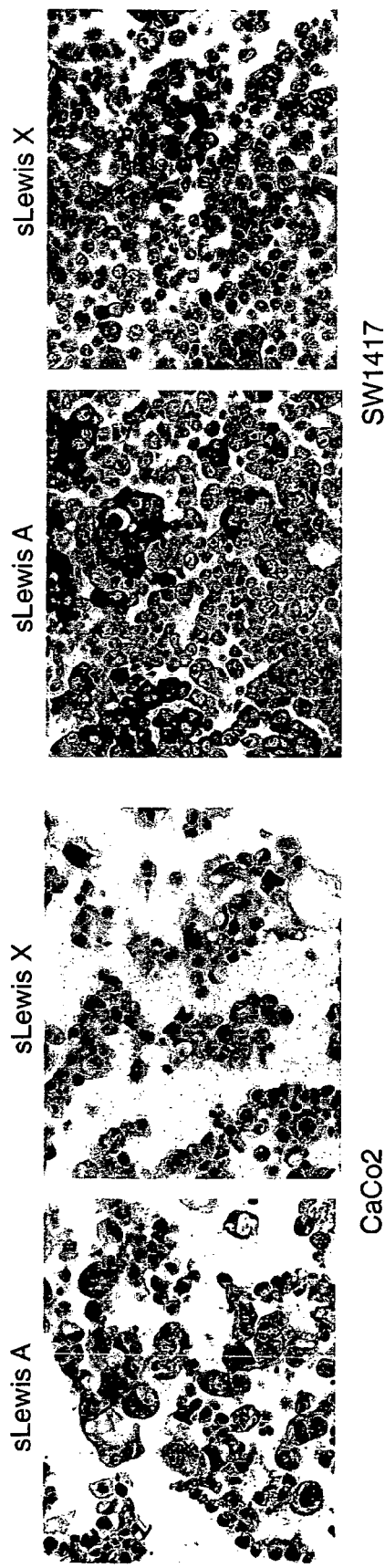
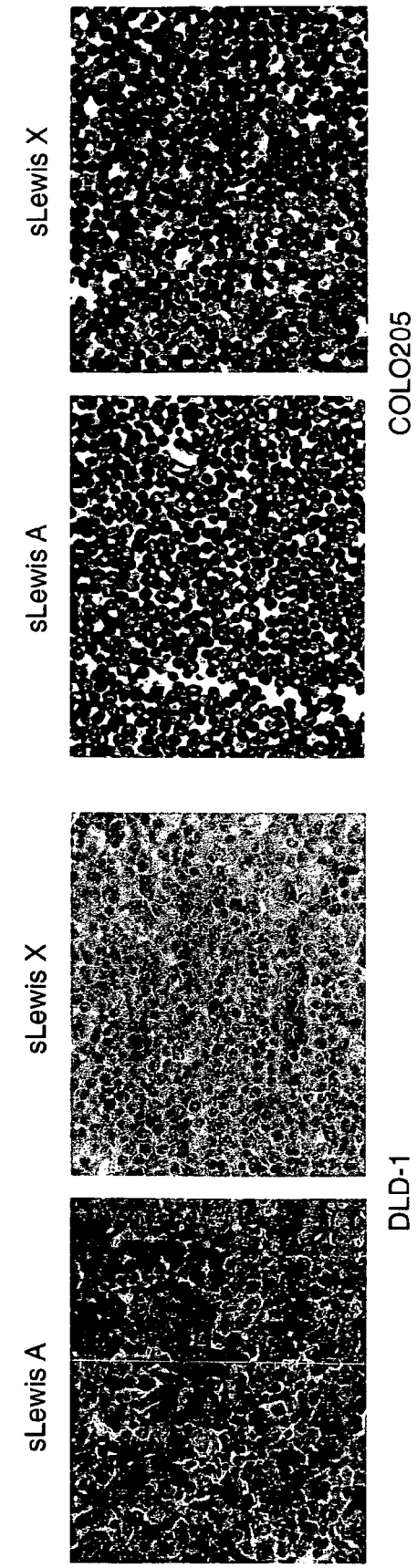
FIG. 12A

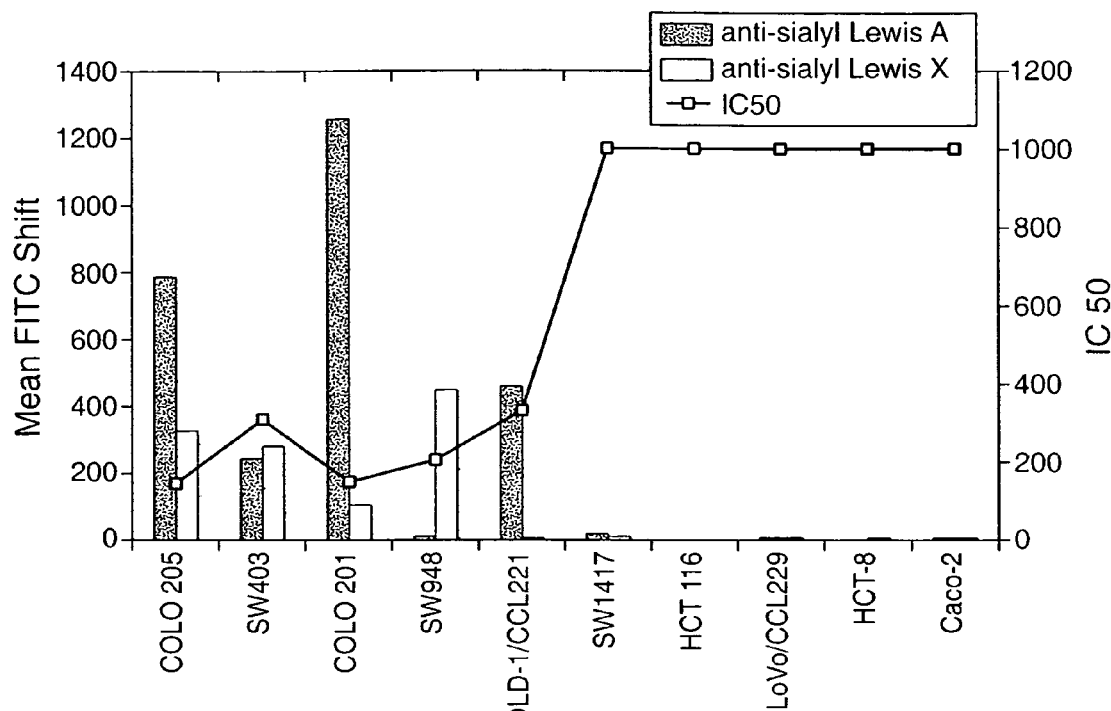

FIG. 12B

IHC Data on CRC Samples

☐ Sialyl-Lewis A staining of primary colorectal adenocarcinomas (Colorectal TMAs):

37 of 74 (50%) are positive; of these 37 cases
19 are 1+
10 are 2+
8 are 3+ in staining intensity
2 of 33 (6%) cases of benign mucosa show positive staining, both cases are 1+

☐ Sialyl-Lewis X staining of primary colorectal adenocarcinomas (Colorectal TMAs):

47 of 75 (63%) are positive; of these 47 cases
25 are 1+
19 are 2+
3 are 3+ in staining intensity
21 of 32 (66%) cases of benign mucosa show positive staining (19 cases are 1+, 2 cases are 2+).

☐ Benign liver tissue shows positive staining on biliary epithelium lining small and intermediate intrahepatic bile ducts; hepatocytes do not show positive staining.

☐ 8 of 9 (88%) metastatic colorectal adenocarcinomas are positive for sialyl-Lewis A and X
7 of the 8 positive cases show strong staining. There is a higher prevalence of sialyl-Lewis A and X expression and stronger reactivity in metastatic compared to primary colorectal adenocarcinomas.

FIG. 13

ASSAYS AND METHODS USING BIOMARKERS

RELATED APPLICATIONS

This application claims priority under Section 119(e) to U.S. provisional application No. 60/599,425 filed Aug. 6, 2004, the contents of which are incorporated herein by reference.

FIELD OF THE INVENTION

The invention described herein relates to methods and assays to detect biomarkers predictive of sensitivity of mammalian cells to Apo2L/TRAIL and/or death receptor agonist antibodies.

BACKGROUND OF THE INVENTION

Various ligands and receptors belonging to the tumor necrosis factor (TNF) superfamily have been identified in the art. Included among such ligands are tumor necrosis factor-alpha ("TNF-alpha"), tumor necrosis factor-beta ("TNF-beta" or "lymphotoxin-alpha"), lymphotoxin-beta ("Lt-beta"), CD30 ligand, CD27 ligand, CD40 ligand, OX-40 ligand, 4-1BB ligand, LIGHT, Apo-1 ligand (also referred to as Fas ligand or CD95 ligand), Apo-2 ligand (also referred to as Apo2L or TRAIL), Apo-3 ligand (also referred to as TWEAK), APRIL, OPG ligand (also referred to as RANK ligand, ODF, or TRANCE), and TALL-1 (also referred to as BlyS, BAFF or THANK) (See, e.g., Ashkenazi, *Nature Review*, 2:420-430 (2002); Ashkenazi and Dixit, *Science*, 281:1305-1308 (1998); Ashkenazi and Dixit, *Curr. Opin. Cell Biol.*, 11:255-260 (2000); Golstein, *Curr. Biol.*, 7:750-753 (1997) Wallach, *Cytokine Reference*, Academic Press, 2000, pages 377-411; Locksley et al., *Cell*, 104:487-501 (2001); Gruss and Dower, Blood, 85:3378-3404 (1995); Schmid et al., Proc. Natl. Acad. Sci., 83:1881 (1986); Dealtry et al., Eur. J. Immunol., 17:689 (1987); Pitti et al., J. Biol. Chem., 271:12687-12690 (1996); Wiley et al., Immunity, 3:673-682 (1995); Browning et al., Cell, 72:847-856 (1993); Armitage et al. Nature, 357:80-82 (1992); WO 97/01633 published Jan. 16, 1997; WO 97/25428 published Jul. 17, 1997; Marsters et al., Curr. Biol., 8:525-528 (1998); Chicheportiche et al., Biol. Chem., 272:32401-32410 (1997); Hahne et al., J. Exp. Med., 188:1185-1190 (1998); WO98/28426 published Jul. 2, 1998; WO98/46751 published Oct. 22, 1998; WO/98/18921 published May 7, 1998; Moore et al., Science, 285:260-263 (1999); Shu et al., J. Leukocyte Biol., 65:680 (1999); Schneider et al., J. Exp. Med., 189:1747-1756 (1999); Mukhopadhyay et al., J. Biol. Chem., 274:15978-15981 (1999)).

Induction of various cellular responses mediated by such TNF family ligands is typically initiated by their binding to specific cell receptors. Some, but not all, TNF family ligands bind to, and induce various biological activity through, cell surface "death receptors" to activate caspases, or enzymes that carry out the cell death or apoptosis pathway (Salvesen et al., *Cell*, 91:443-446 (1997). Included among the members of the TNF receptor superfamily identified to date are TNFR1, TNFR2, TACI, GITR, CD27, OX-40, CD30, CD40, HVEM, Fas (also referred to as Apo-1 or CD95), DR4 (also referred to as TRAIL-R1), DR5 (also referred to as Apo-2 or TRAIL-R2), DcR1, DcR2, osteoprotegerin (OPG), RANK and Apo-3 (also referred to as DR3 or TRAMP) (see, e.g., Ashkenazi, *Nature Reviews*, 2:420-430 (2002); Ashkenazi and Dixit, *Science*, 281:1305-1308 (1998); Ashkenazi and Dixit, *Curr. Opin. Cell Biol.*, 11:255-260 (2000); Golstein, *Curr. Biol.*, 7:750-753 (1997) Wallach, *Cytokine Reference*, Academic Press, 2000, pages 377-411; Locksley et al., *Cell*, 104:487-501 (2001); Gruss and Dower, Blood, 85:3378-3404 (1995); Hohman et al., J. Biol. Chem., 264:14927-14934 (1989); Brockhaus et al., Proc. Natl. Acad. Sci., 87:3127-3131 (1990); EP 417,563, published Mar. 20, 1991; Loetscher et al., Cell, 61:351 (1990); Schall et al., Cell, 61:361 (1990); Smith et al., Science, 248:1019-1023 (1990); Lewis et al., Proc. Natl. Acad. Sci., 88:2830-2834 (1991); Goodwin et al., Mol. Cell. Biol., 11:3020-3026 (1991); Stamenkovic et al., EMBO J., 8:1403-1410 (1989); Mallett et al., EMBO J., 9:1063-1068 (1990); Anderson et al., Nature, 390:175-179 (1997); Chicheportiche et al., J. Biol. Chem., 272:32401-32410 (1997); Pan et al., Science, 276:111-113 (1997); Pan et al., Science, 277:815-818 (1997); Sheridan et al., Science, 277:818-821 (1997); Degli-Esposti et al., J. Exp. Med., 186:1165-1170 (1997); Marsters et al., Curr. Biol., 7:1003-1006 (1997); Tsuda et al., BBRC, 234:137-142 (1997); Nocentini et al., Proc. Natl. Acad. Sci., 94:6216-6221 (1997); vonBulow et al., Science, 278:138-141 (1997)).

Most of these TNF receptor family members share the typical structure of cell surface receptors including extracellular, transmembrane and intracellular regions, while others are found naturally as soluble proteins lacking a transmembrane and intracellular domain. The extracellular portion of typical TNFRs contains a repetitive amino acid sequence pattern of multiple cysteine-rich domains (CRDs), starting from the $NH_2$-terminus.

The ligand referred to as Apo-2L or TRAIL was identified several years ago as a member of the TNF family of cytokines. (see, e.g., Wiley et al., Immunity, 3:673-682 (1995); Pitti et al., J. Biol. Chem., 271:12697-12690 (1996); WO 97/01633; WO 97/25428; U.S. Pat. No. 5,763,223 issued Jun. 9, 1998; U.S. Pat. No. 6,284,236 issued Sep. 4, 2001). The full-length native sequence human Apo2L/TRAIL polypeptide is a 281 amino acid long, Type II transmembrane protein. Some cells can produce a natural soluble form of the polypeptide, through enzymatic cleavage of the polypeptide's extracellular region (Mariani et al., J. Cell. Biol., 137:221-229 (1997)). Crystallographic studies of soluble forms of Apo2L/TRAIL reveal a homotrimeric structure similar to the structures of TNF and other related proteins (Hymowitz et al., *Molec. Cell*, 4:563-571 (1999); Cha et al., *Immunity*, 11:253-261 (1999); Mongkolsapaya et al., *Nature Structural Biology*, 6:1048 (1999); Hymowitz et al., Biochemistry, 39:633-644 (2000)). Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. (Hymowitz et al., supra; Bodmer et al., J. Biol. Chem., 275:20632-20637 (2000)).

It has been reported in the literature that Apo2L/TRAIL may play a role in immune system modulation, including autoimmune diseases such as rheumatoid arthritis [see, e.g., Thomas et al., J. Immunol., 161:2195-2200 (1998); Johnsen et al., Cytokine, 11:664-672 (1999); Griffith et al., J. Exp. Med., 189:1343-1353 (1999); Song et al., J. Exp. Med., 191: 1095-1103 (2000)].

Soluble forms of Apo2L/TRAIL have also been reported to induce apoptosis in a variety of cancer cells, including colon, lung, breast, prostate, bladder, kidney, ovarian and brain tumors, as well as melanoma, leukemia, and multiple myeloma (see, e.g., Wiley et al., supra; Pitti et al., supra; U.S. Pat. No. 6,030,945 issued Feb. 29, 2000; U.S. Pat. No. 6,746, 668 issued Jun. 8, 2004; Rieger et al., FEBS Letters, 427:124-

128 (1998); Ashkenazi et al., J. Clin. Invest., 104:155-162 (1999); Walczak et al., Nature Med., 5:157-163 (1999); Keane et al., Cancer Research, 59:734-741 (1999); Mizutani et al., Clin. Cancer Res., 5:2605-2612 (1999); Gazitt, Leukemia, 13:1817-1824 (1999); Yu et al., Cancer Res., 60:2384-2389 (2000); Chinnaiyan et al., Proc. Natl. Acad. Sci., 97:1754-1759 (2000)). In vivo studies in murine tumor models further suggest that Apo2L/TRAIL, alone or in combination with chemotherapy or radiation therapy, can exert substantial anti-tumor effects (see, e.g., Ashkenazi et al., supra; Walzcak et al., supra; Gliniak et al., Cancer Res., 59:6153-6158 (1999); Chinnaiyan et al., supra; Roth et al., Biochem. Biophys. Res. Comm., 265:1999 (1999); PCT Application US/00/15512; PCT Application US/01/23691). In contrast to many types of cancer cells, most normal human cell types appear to be resistant to apoptosis induction by certain recombinant forms of Apo2L/TRAIL (Ashkenazi et al., supra; Walzcak et al., supra). Jo et al. has reported that a polyhistidine-tagged soluble form of Apo2L/TRAIL induced apoptosis in vitro in normal isolated human, but not non-human, hepatocytes (Jo et al., Nature Med., 6:564-567 (2000); see also, Nagata, Nature Med., 6:502-503 (2000)). It is believed that certain recombinant Apo2L/TRAIL preparations may vary in terms of biochemical properties and biological activities on diseased versus normal cells, depending, for example, on the presence or absence of a tag molecule, zinc content, and % trimer content (See, Lawrence et al., Nature Med., Letter to the Editor, 7:383-385 (2001); Qin et al., Nature Med., Letter to the Editor, 7:385-386 (2001)).

Apo2L/TRAIL has been found to bind at least five different receptors. At least two of the receptors which bind Apo2L/TRAIL contain a functional, cytoplasmic death domain. One such receptor has been referred to as "DR4" (and alternatively as TR4 or TRAIL-R1) (Pan et al., Science, 276:111-113 (1997); see also WO98/32856 published Jul. 30, 1998; WO99/37684 published Jul. 29, 1999; WO 00/73349 published Dec. 7, 2000; U.S. Pat. No. 6,433,147 issued Aug. 13, 2002; U.S. Pat. No. 6,461,823 issued Oct. 8, 2002, and U.S. Pat. No. 6,342,383 issued Jan. 29, 2002).

Another such receptor for Apo2L/TRAIL has been referred to as DR5 (it has also been alternatively referred to as Apo-2; TRAIL-R or TRAIL-R2, TR6, Tango-63, hAPO8, TRICK2 or KILLER) (see, e.g., Sheridan et al., Science, 277:818-821 (1997), Pan et al., Science, 277:815-818 (1997), WO98/51793 published Nov. 19, 1998; WO98/41629 published Sep. 24, 1998; Screaton et al., Curr. Biol., 7:693-696 (1997); Walczak et al., EMBO J., 16:5386-5387 (1997); Wu et al., Nature Genetics, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/01255540 published Jul. 3, 2003; US 2002/0160446 published Oct. 31, 2002, US 2002/0048785 published Apr. 25, 2002; U.S. Pat. No. 6,342,369 issued February, 2002; U.S. Pat. No. 6,569,642 issued May 27, 2003, U.S. Pat. No. 6,072,047 issued Jun. 6, 2000, U.S. Pat. No. 6,642,358 issued Nov. 4, 2003; U.S. Pat. No. 6,743,625 issued Jun. 1, 2004). Like DR4, DR5 is reported to contain a cytoplasmic death domain and be capable of signaling apoptosis upon ligand binding (or upon binding a molecule, such as an agonist antibody, which mimics the activity of the ligand). The crystal structure of the complex formed between Apo-2L/TRAIL and DR5 is described in Hymowitz et al., Molecular Cell, 4:563-571 (1999).

Upon ligand binding, both DR4 and DR5 can trigger apoptosis independently by recruiting and activating the apoptosis initiator, caspase-8, through the death-domain-containing adaptor molecule referred to as FADD/Mort1 [Kischkel et al., Immunity, 12:611-620 (2000); Sprick et al., Immunity, 12:599-609 (2000); Bodmer et al., Nature Cell Biol., 2:241-243 (2000)].

Apo2L/TRAIL has been reported to also bind those receptors referred to as DcR1, DcR2 and OPG, which believed to function as inhibitors, rather than transducers of signaling (see., e.g., DCR1 (also referred to as TRID, LIT or TRAIL-R3) [Pan et al., Science, 276:111-113 (1997); Sheridan et al., Science, 277:818-821 (1997); McFarlane et al., J. Biol. Chem., 272:25417-25420 (1997); Schneider et al., FEBS Letters, 416:329-334 (1997); Degli-Esposti et al., J. Exp. Med., 186:1165-1170 (1997); and Mongkolsapaya et al., J. Immunol., 160:3-6 (1998); DCR2 (also called TRUNDD or TRAIL-R4) [Marsters et al., Curr. Biol., 7:1003-1006 (1997); Pan et al., FEBS Letters, 424:41-45 (1998); Degli-Esposti et al., Immunity, 7:813-820 (1997)], and OPG [Simonet et al., supra]. In contrast to DR4 and DR5, the DcR1 and DcR2 receptors do not signal apoptosis.

Certain antibodies which bind to the DR4 and/or DR5 receptors have been reported in the literature. For example, anti-DR4 antibodies directed to the DR4 receptor and having agonistic or apoptotic activity in certain mammalian cells are described in, e.g., WO 99/37684 published Jul. 29, 1999; WO 00/73349 published Jul. 12, 2000; WO 03/066661 published Aug. 14, 2003. See, also, e.g., Griffith et al., J. Immunol., 162:2597-2605 (1999); Chuntharapai et al., J. Immunol., 166: 4891-4898 (2001); WO 02/097033 published Dec. 2, 2002; WO 03/042367 published May 22, 2003; WO 03/038043 published May 8, 2003; WO 03/037913 published May 8, 2003. Certain anti-DR5 antibodies have likewise been described, see, e.g., WO 98/51793 published Nov. 8, 1998; Griffith et al., J. Immunol., 162:2597-2605 (1999); Ichikawa et al., Nature Med., 7:954-960 (2001); Hylander et al., "An Antibody to DR5 (TRAIL-Receptor 2) Suppresses the Growth of Patient Derived Gastrointestinal Tumors Grown in SCID mice", Abstract, 2d International Congress on Monoclonal Antibodies in Cancers, Aug. 29-Sep. 1, 2002, Banff, Alberta, Canada; WO 03/038043 published May 8, 2003; WO 03/037913 published May 8, 2003. In addition, certain antibodies having cross-reactivity to both DR4 and DR5 receptors have been described (see, e.g., U.S. Pat. No. 6,252,050 issued Jun. 26, 2001).

Neoplastic transformation of some mammalian cells has in certain instances, been associated with characteristic changes in the expression of sialyl Lewis A and sialyl Lewis X antigens. Relatively high amounts of sialyl Lewis A/X are present, for example, in some human adenocarcinomas of the colon, pancreas and stomach, and assays using antibodies directed to the carbohydrate structures on these antigens have been employed as a means to detect pancreatic and gastrointestinal cancers. (see, e.g., Ugorski et al., Acta Biochimica Polonica, 49:2:303-311 (2002). The level of expression of these carbohydrate tumor markers has also been correlated with clinical outcome, patient survival times and an indicator of metastatic disease.

Both sialyl Lewis A and sialyl Lewis X have been shown to bind to a family of carbohydrate-binding proteins involved in the extravasation of cells from the bloodstream, called the selectins. Some reports suggest that sialyl Lewis A and X are ligands for E-selectin, and may be responsible for the adhesion of human cancer cells to endothelium. Sialylated Lewis structures present on the surface of cancer cells are carried by the carbohydrate chains of glycoproteins and glycolipids and bind E-selectin present on endothelial cells. Selectins and their carbohydrate ligands may accordingly play an important role in the selective homing of tumor cells during metastasis.

The biosynthesis of sialyl Lewis A and X is believed to be dependent upon the final addition of fucose from guanosine diphosphate-fucose (GDP-Fuc) in alpha (1,3) and alpha (1,4) linkage to sialylated precursors by cell type-specific and developmental stage-specific enzymes, a step catalyzed by alpha-1,3/1,4-fucosyltransferases (alpha 1,3/1,4 Fuc-T, FUT).

Several human fucosyltransferase genes have been cloned and characterized to date. Expression of these genes (FUT 3-7) and their enzyme products (Fuc-TIII-VII) appears to be tissue specific. The enzymes encoded by the five genes are named FUTIII, FUTIV, FUTV, FUTVI and FUTVII. The three genes encoding FUTIII, FUTV and FUTVI are localized at close physical positions on chromosome 19p13.3. Biochemical and molecular cloning studies suggest that lineage-specific expression of the sialyl Lewis A/X moiety is determined by lineage-specific expression of alpha-1,3-fucosyltransferase genes, whose enzyme products operate on constitutively expressed oligosaccharide precursors to yield surface-localized sialyl Lewis A/X determinants. The human fucosyltransferases responsible for activity in epithelial tissues are FUT3 and FUT6. FUT3 [also called the Lewis alpha (1,3/1,4)fucosyltransferase gene] and FUT6 [the plasma alpha (1,3)fucosyltransferase gene] transcripts are present in both normal and transformed tissues. Fucosyltransferase transcripts are also prevalent in numerous adenocarcinoma cell lines, with notably high expression of FUT3 and 6 in colon carcinoma. (see, e.g, Ugorski et al., *Acta Biochimica Polonica*, 49:303-311 (2002); Nakamori et al., *Dis. Colon Rectum.*, 40:420-431 (1997); Takada et al., *Cancer Res.*, 53:354-361 (1993); Ichikawa et al., *J. Surg. Oncol.*, 75:98-102 (2000)); Nakagoe et al., J Exp Clin Cancer Res., 2002 March;21(1):107-13; Matsumoto et al., Br J Cancer. 2002 Jan. 21;86(2):161-7; Ito et al., J Gastroenterol. 2001 December;36(12):823-9; Nakagoe et al., Cancer Detect Prev. 2001; 25(3):299-308; Kumamoto et al., Cancer Res. 2001 Jun. 1;61 (11):4620-7; Murata et al., Dis Colon Rectum. 2001 April;44 (4):A2-A4; Nakagoe et al., J Exp Clin Cancer Res. 2001 March;20(1):85-90; Nakagoe et al., J Gastroenterol. 2001 March;36(3):166-72; Nakagoe et al., Tumour Biol. 2001 March-April;22(2):115-22; Nakagoe et al., Can J Gastroenterol. 2000 October;14(9):753-60; Izawa et al., Cancer Res. 2000 Mar. 1;60(5):1410-6; Tanaka et al., Hepatogastroenterology. 1999 March-April; 46(26):875-82; Matsushita et al., Cancer Lett. 1998 Nov. 27;133(2):151-60; Sato et al. , Anticancer Res. 1997 September-October;17(5A):3505-11; Yamada et al., Br J Cancer. 1997;76(5):582-7; Nakamori et al., Dis Colon Rectum. 1997 April;40(4):420-31; Srinivas et al., Scand J Immunol. 1996 September;44(3):197-203; Matsushita et al., Lab Invest. 1990 December;63(6):780-91; Ashizawa et al., J Exp Clin Cancer Res. 2003 March;22(1):91-8; Nakagoe et al., J Exp Clin Cancer Res. 2002 September;21 (3):363-9; Nakagoe et al., Anticancer Res. 2002 January-Febuary;22(1A):451-8; Nakagoe et al., J Clin Gastroenterol. 2002 April;34(4):408-15; Nakagoe et al., Cancer Lett. 2002 Jan. 25;175(2):213-21; Tatsumi et al., Clin Exp Metastasis. 1998 November;16(8):743-50; Ikeda et al., J Surg Oncol. 1996 July;62(3):171-6; Ikeda et al., Eur J Surg Oncol. 1995 April;21(2):168-75; Togayachi et al., Int J Cancer. 1999 Sep. 24;83(1):70-9; Satoh et al., Clin Cancer Res. 1997 April;3(4): 495-9; Satoh et al., Respiration. 1998;65(4):295-8; Satoh et al., Anticancer Res. 1998 July-August;18(4B):2865-8; Fukuoka et al., Lung Cancer. 1998 May;20(2):109-16; Fujiwara et al., Anticancer Res. 1998 March-April;18(2A):1043-6; Ogawa et al., Int J Cancer. 1997 Apr. 22;74(2):189-92; Ogawa et al., J Thorac Cardiovasc Surg. 1994 August;108(2): 329-36; Asao et al., Cancer. 1989 Dec. 15;64(12):2541-5; Narita et al., Breast Cancer. 1996 Mar. 29;3(l):19-23; Yamaguchi et al., Oncology. 1998 July-August;55(4):357-62; Sikut et al., Int J Cancer. 1996 May 29;66(5):617-23; Saito et al., Anticancer Res. 2003 July-August;23(4):3441-6; Fujii et al., Urol Int. 2000;64(3):129-33; Idikio et al., Glycoconj J. 1997 November;14(7):875-7; Inoue et al., Obstet Gynecol. 1992 March;79(3):434-40; Yamashita et al., Eur J Cancer. 2000 January;36(1):113-20; Hamanaka et al., Pancreas. 1996 August;13(2):160-5; Ho et al., Cancer Res. 1995 Aug. 15;55(16):3659-63.

SUMMARY OF THE INVENTION

The invention disclosed herein provides methods and assays examining expression of one or more biomarkers in a mammalian tissue or cell sample, wherein the expression of one or more such biomarkers is predictive of whether the tissue or cell sample will be sensitive to apoptosis-inducing agents such as Apo2L/TRAIL and anti-DR5 agonist antibodies. In various embodiments of the invention, the methods and assays examine expression of biomarkers such as certain fucosyltransferases, in particular fucosyltransferase 3 (FUT3) and/or fucosyltransferase 6 (FUT6), as well as sialyl Lewis A and/or X antigens.

As discussed above, most normal human cell types appear to be resistant to apoptosis induction by certain recombinant forms of Apo2L/TRAIL (Ashkenazi et al., supra; Walzcak et al., supra). It has also been observed that some populations of diseased human cell types (such as certain populations of cancer cells) are resistant to apoptosis induction by certain recombinant forms of Apo2L/TRAIL (Ashkenazi et al., *J. Clin. Invest.*, 1999, supra; Walczak et al., *Nature Med.*, 1999, supra). Consequently, by examining a mammalian tissue or cell sample for expression of certain biomarkers by way of an assay, one can conveniently and efficiently obtain information useful in assessing appropriate or effective therapies for treating patients. For example, information obtained from an assay to detect FUT3 or FUT6 expression in a mammalian tissue or cell sample can provide physicians with useful data that can be used to determine an optimal therapeutic regimen (using Apo2L/TRAIL or death receptor agonist antibodies) for patients suffering from a disorder such as cancer.

The invention provides methods for predicting the sensitivity of a mammalian tissue or cells sample (such as a cancer cell) to Apo2L/TRAIL or a death receptor agonist antibody. In certain embodiments, the methods comprise obtaining a mammalian tissue or cell sample and examining the tissue or cell for expression of fucosyltransferase 3 or fucosyltransferase 6. The methods may also comprise examining the tissue or cell for expression of another biomarker such as sialyl Lewis A and/or X antigen(s). The methods may be conducted in a variety of assay formats, including assays detecting mRNA expression, enzymatic assays detecting presence of enzymatic activity, immunohistochemistry assays, and others discussed herein. Determination of expression of such biomarkers in said tissues or cells will be predictive that such tissues or cells will be sensitive to the apoptosis-inducing activity of Apo2/TRAIL and/or death receptor antibody. In optional embodiments, the tissues or cells may also be examined for expression of DR4, DR5, DcR1 or DcR2 receptors.

Further methods of the invention include methods of inducing apoptosis in a mammalian tissue or cell sample, comprising steps of obtaining a mammalian tissue or cell sample, examining the tissue or cell for expression of one or more biomarkers, such as fucosyltransferase 3, fucosyltransferase 6, sialyl Lewis A and/or X antigen(s), and upon determining said tissue or cell sample expresses said one or more biomarkers, exposing said tissue or cell sample to an effective amount of Apo2L/TRAIL or death receptor agonist antibody. The steps in the methods for examining expression of one or more biomarkers may be conducted in a variety of assay formats, including assays detecting mRNA expression, enzymatic assays detecting presence of enzymatic activity, and immunohistochemistry assays. In optional embodiments, the methods also comprise examining the tissue or cell sample for expression of DR4, DR5, DcR1, or DcR2 receptors. optionally, the tissue or cell sample comprises cancer tissue or cells.

Still further methods of the invention include methods of treating a disorder in a mammal, such as an immune related disorder, or cancer, comprising steps of obtaining tissue or a cell sample from the mammal, examining the tissue or cells for expression of one or more biomarkers, such as fucosyltransferase 3, fucosyltransferase 6, sialyl Lewis A and/or x antigen(s), and upon determining said tissue or cell sample expresses said one or more biomarkers, administering an effective amount of Apo2L/TRAIL or death receptor agonist antibody to said mammal. The steps in the methods for examining expression of one or more biomarkers may be conducted in a variety of assay formats, including assays detecting mRNA expression, enzymatic assays detecting presence of enzymatic activity, and immunohistochemistry assays. In optional embodiments, the methods also comprise examining the tissue or cell sample for expression of DR4, DR5, DcR1, or DcR2 receptors. optionally, the methods comprise treating cancer in a mammal. Optionally, the methods comprise, in addition to administering an effective amount of Apo2L/TRAIL and/or death receptor agonist antibody, administering chemotherapeutic agent(s) or radiation therapy to said mammal.

Further embodiments are more particularly disclosed by the following claims:

1. A method for predicting the sensitivity of a mammalian tissue or cells sample to Apo2L/TRAIL, comprising the steps of:
   obtaining a mammalian tissue or cell sample;
   examining the tissue or cell sample to detect expression of one or more biomarkers selected from the group of fucosyltransferase 3, fucosyltransferase 6, sialyl Lewis A and/or X antigen(s), wherein expression of said one or more biomarkers is predictive that said tissue or cell sample is sensitive to apoptosis-inducing activity of Apo2L/TRAIL.
2. The method of claim 1 wherein said expression of one or more biomarkers is examined by detecting mRNA expression of fucosyltransferase 3 or fucosyltransferase 6.
3. The method of claim 1 wherein said expression of one or more biomarkers is examined by immunohistochemistry to detect expression of sialyl Lewis A and/or X antigen(s).
4. The method of claim 1 further comprising the step of examining expression of DR4, DR5, DcR1, or DcR2 receptors in said tissue or cell sample.
5. The method of claim 1 wherein tissue or cell sample comprises cancer tissue or cells.
6. The method of claim 5 wherein said cancer cells are colon, colorectal, gastrointestinal, or pancreatic cancer cells or tissue.
7. A method for inducing apoptosis in a mammalian tissue or cell sample, comprising the steps of:
   obtaining a mammalian tissue or cell sample;
   examining the tissue or cell sample to detect expression of one or more biomarkers selected from the group of fucosyltransferase 3, fucosyltransferase 6, sialyl Lewis A and/or X antigen(s), and subsequent to detecting expression of said one or more biomarkers, exposing said tissue or cell sample to an effective amount of Apo2L/TRAIL.
8. The method of claim 7 wherein said expression of one or more biomarkers is examined by testing for mRNA expression of fucosyltransferase 3 or fucosyltransferase 6.
9. The method of claim 7 wherein said expression of one or more biomarkers is examined by immunohistochemistry to detect expression of sialyl Lewis A and/or X antigen(s).
10. The method of claim 7 further comprising the step of examining expression of DR4, DR5, DcR1 or DcR2 receptors in said tissue or cell sample.
11. The method of claim 7 wherein said tissue or cell sample comprises cancer tissue or cells.
12. The method of claim 11 wherein said cancer cells are colon, colorectal, gastrointestinal, or pancreatic cancer cells or tissue.
13. The method of claim 7 wherein said cells are exposed to an effective amount of Apo2L/TRAIL polypeptide comprising amino acids 114-281 of FIG. 1.
14. A method of treating a disorder in a mammal, such as an immune related disorder or cancer, comprising the steps of:
   obtaining a tissue or cell sample from said mammal;
   examining the tissue or cell sample to detect expression of one or more biomarkers selected from the group of fucosyltransferase 3, fucosyltransferase 6, sialyl Lewis A and/or X antigen(s), and subsequent to detecting expression of said one or more biomarkers, administering to said mammal an effective amount of Apo2L/TRAIL.
15. The method of claim 14 wherein said expression of one or more biomarkers is examined by detecting MRNA expression of fucosyltransferase 3 or fucosyltransferase 6.
16. The method of claim 14 wherein said expression of one or more biomarkers is examined by immunohistochemistry to detect expression of sialyl Lewis A and/or X antigen(s).
17. The method of claim 14 further comprising the step of examining expression of DR4, DR5, DcR1 or DcR2 receptors in said tissue or cell.
18. The method of claim 14 wherein tissue or cell sample comprises cancer tissue or cells.
19. The method of claim 18 wherein said cancer cells or tissue comprises colon, colorectal, gastrointestinal, or pancreatic cancer cells or tissue.
20. The method of claim 14 wherein an effective amount of Apo2L/TRAIL polypeptide comprising amino acids 114-281 of FIG. 1 is administered to said mammal.
21. The method of claim 14 wherein a chemotherapeutic agent(s) or radiation therapy is also administered to said mammal.
22. The method of claim 14 wherein a cytokine, cytotoxic agent or growth inhibitory agent is also administered to said mammal.
23. The method of claim 7 wherein said Apo2L/TRAIL polypeptide is linked to a polyethylene glycol molecule.
24. The method of claim 14 wherein said Apo2L/TRAIL polypeptide is linked to a polyethylene glycol molecule.
25. The method of claim 6 wherein said cancer cells are colon or colorectal cancer cells.
26. The method of claim 1 wherein said Apo2L/TRAIL is a polypeptide comprising amino acids 41-281 of FIG. 1 (SEQ ID NO:1) or a biologically active fragment thereof.

27. The method of claim 26 wherein said Apo2L/TRAIL is a polypeptide comprising amino acids 114-281 of FIG. 1 (SEQ ID NO:1).

28. The method of claim 12 wherein said cancer cells are colon or colorectal cancer cells.

29. The method of claim 20 wherein said Apo2L/TRAIL polypeptide consists of amino acids 114-281 of FIG. 1 (SEQ ID NO:1).

30. A method for predicting the sensitivity of a mammalian colon or colorectal cancer cells to Apo2L/TRAIL, comprising the steps of:
   obtaining mammalian mammalian colon or colorectal cancer cells;
   examining the cancer cells to detect expression of one or more biomarkers selected from the group of fucosyltransferase 3, fucosyltransferase 6, sialyl Lewis A and/or X antigen(s), wherein expression of said one or more biomarkers is predictive that said cancer cells are sensitive to apoptosis-inducing activity of Apo2L/TRAIL.

31. A method for inducing apoptosis in mammalian colon or colorectal cancer cells, comprising the steps of:
   obtaining mammalian colon or colorectal cancer cells;
   examining the cancer cells to detect expression of one or more biomarkers selected from the group of fucosyltransferase 3, fucosyltransferase 6, sialyl Lewis A and/or X antigen(s), and subsequent to detecting expression of said one-or more biomarkers, exposing said cancer cells to an effective amount of Apo2L/TRAIL polypeptide.

32. The method of claim 31 wherein said Apo2L/TRAIL polypeptide comprises amino acids 41-281 of FIG. 1 (SEQ ID NO:1) or a fragment thereof which has apoptotic activity.

33. The method of claim 32 wherein said Apo2L/TRAIL polypeptide is linked to a polyethylene glycol molecule.

34. The method of claim 32 wherein said Apo2L/TRAIL polypeptide comprises amino acids 114-281 of FIG. 1 (SEQ ID NO:1).

35. A method of treating colon or colorectal cancer in a mammal, comprising the steps of:
   obtaining a colon or colorectal cancer cell sample from said mammal;
   examining the cancer cell sample to detect expression of one or more biomarkers selected from the group of fucosyltransferase 3, fucosyltransferase 6, sialyl Lewis A and/or X antigen(s), and subsequent to detecting expression of said one or more biomarkers, administering to said mammal an effective amount of Apo2L/TRAIL.

36. The method of claim 35 wherein said Apo2L/TRAIL polypeptide comprises amino acids 41-281 of FIG. 1 (SEQ ID NO:1) or a fragment thereof which has apoptotic activity.

37. The method of claim 36 wherein said Apo2L/TRAIL polypeptide is linked to a polyethylene glycol molecule.

38. The method of claim 36 wherein said Apo2L/TRAIL polypeptide comprises amino acids 114-281 of FIG. 1 (SEQ ID NO:1).

BRIEF DESCRIPTION OF THE FIGURES

FIG. 1 shows the nucleotide sequence of human Apo-2 ligand cDNA (SEQ ID NO:2) and its derived amino acid sequence (SEQ ID NO:1). The "N" at nucleotide position 447 is used to indicate the nucleotide base may be a "T" or "G".

FIGS. 2A and 2B show the nucleotide sequence of a cDNA (SEQ ID NO:4) for full length human DR4 and its derived amino acid sequence (SEQ ID NO:3). The respective nucleotide and amino acid sequences for human DR4 are also reported in Pan et al., *Science,* 276:111 (1997).

FIG. 3A shows the 411 amino acid sequence (SEQ ID NO:5) of human DR5 as published in WO 98/51793 on Nov. 19, 1998. A transcriptional splice variant of human DR5 is known in the art. This DR5 splice variant encodes the 440 amino acid sequence (SEQ ID NO:6) of human DR5 shown in FIGS. 3B and 3C as published in WO 98/35986 on Aug. 20, 1998.

FIG. 3D shows the nucleotide sequences of cDNA (SEQ ID NO:7) for full length human DcR1 and its derived amino acid sequence (SEQ ID NO:8). The respective nucleotide and amino acid sequences for human DcR1 (and particular domains thereof) are also shown and described in WO 98/58062.

FIG. 3E shows the nucleotide sequences of cDNA (SEQ ID NO:9) for full length human DcR2 and its derived amino acid sequence (SEQ ID NO:10). The respective nucleotide and amino acid sequences for human DcR2 (and particular domains thereof) are shown in WO 99/10484.

FIG. 4 shows the nucleotide sequence of a cDNA (SEQ ID NO:11) for full length human (1,3/1,4) fucosyltransferase (FUT3) and its derived amino acid sequence (SEQ ID NO:12). These sequences correspond to GenBank Accession Number HSU27328 and are described for example in Kukowska-Latallo et al., Genes Dev. 1990 August;4(8):1288-303.

FIG. 5 shows the nucleotide sequence of a cDNA (SEQ ID NO:13) for full length human alpha (1,3) fucosyltransferase (FUT6) and its derived amino acid sequence (SEQ ID NO:14). These sequences correspond to GenBank Accession Number HSU27333 and are described for example in Koszdin and Bowen, Biochem Biophys Res Commun. 1992 Aug. 31;187(1):152-7.

FIG. 6 provides a summary chart of the data obtained in analyzing 28 colon or colorectal cancer cell lines for sensitivity or resistance to apoptotic activity of Apo2L (+0.5% fetal bovine serum "FBS" or 10% FBS) or DR5 monoclonal antibody "mab", cross-linked "XL" or not crosslinked, +0.5% fetal bovine serum "FBS" or 10% FBS) and expression of FUT 3, FUT 6, Sialyl Lewis A and Sialyl Lewis X.

FIG. 9B shows the results of a Fisher's Exact test analyzing sensitivity ("sens") or resistance ("res") of the various colon or colorectal cancer cell lines and the statistical significance between FUT 3 and sialyl Lewis A/X expression and sensitivity of the respective cell lines to DR5 antibody apoptotic activity.

FIG. 10 provides a comparison of various colon or colorectal cancer cell lines for expression of DcR1 or DcR2 receptors (as determined by quantitative PCR) and the status (sensitive or resistant) of certain cell lines to Apo2L or DR5 antibody.

FIG. 12 show immunohistochemical staining for sialyl Lewis A and X on four colorectal cancer cell lines, CaCo2, SW 1417, DLD-1, and Colo 205, and its correlation to expression of sialyl Lewis A and X as measured by FACS and its correlation to sensitivity to Apo2L.

FIG. 13 shows a summary of IHC experiments demonstrating expression of sialyl Lewis A and X in tissue samples of normal colon mucosa, normal liver tissue, primary colon cancer, and colon cancer metastases.

DETAILED DESCRIPTION OF THE INVENTION

Figure 7:
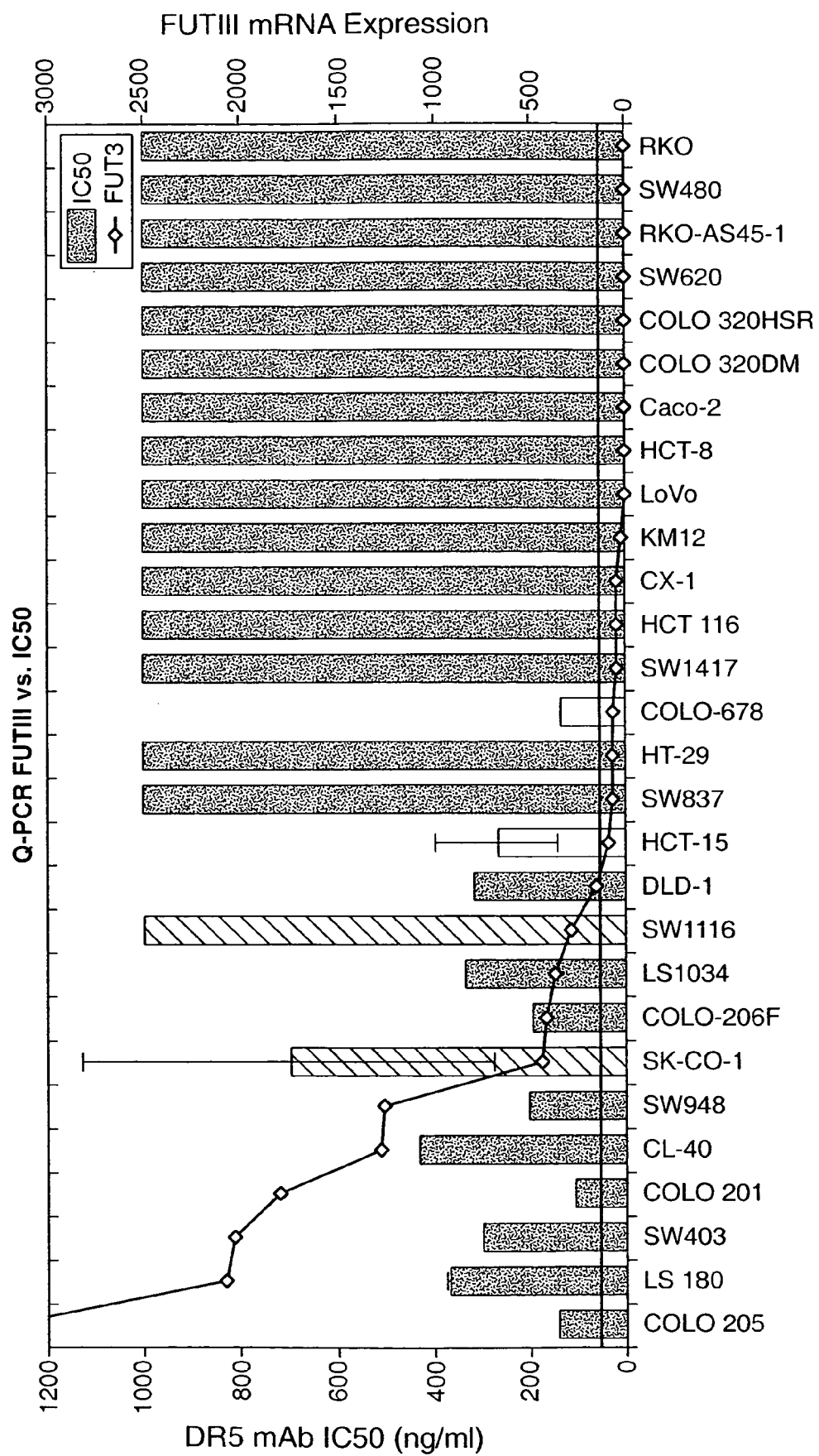
FIG. 7 provides a comparison of sensitivity of various colon or colorectal cancer cell lines to DR5 antibody and the expression of FUT 3, as measured by quantitative PCR.

The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Before the present methods and assays are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a genetic alteration" includes a plurality of such alterations and reference to "a probe" includes reference to one or more probes and equivalents thereof known to those skilled in the art, and so forth.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

I. Definitions

The terms "Apo2L/TRAIL", "Apo-2L", and "TRAIL" are used herein to refer to a polypeptide sequence which includes amino acid residues 114-281, inclusive, 95-281, inclusive, residues 92-281, inclusive, residues 91-281, inclusive, residues 41-281, inclusive, residues 15-281, inclusive, or residues 1-281, inclusive, of the amino acid sequence shown in FIG. 1, as well as biologically active fragments, deletional, insertional, or substitutional variants of the above sequences. In one embodiment, the polypeptide sequence comprises residues 114-281 of FIG. 1), and optionally, consists of residues 114-281 of FIG. 1. Optionally, the polypeptide sequence comprises residues 92-281 or residues 91-281 of FIG. 1. The Apo-2L polypeptides may be encoded by the native nucleotide sequence shown in FIG. 1. Optionally, the codon which encodes residue Pro119 (FIG. 1. may be "CCT" or "CCG". In other embodiments, the fragments or variants are biologically active and have at least about 80% amino acid sequence identity, more preferably at least about 90% sequence identity, and even more preferably, at least 95%, 96%, 97%, 98%, or 99% sequence identity with any one of the above recited Apo2L/TRAIL sequences. Optionally, the Apo2L/TRAIL polypeptide is encoded by a nucleotide sequence which hybridizes under stringent conditions with the encoding polynucleotide sequence provided in FIG. 1. The definition encompasses substitutional variants of Apo2L/TRAIL in which at least one of its native amino acids are substituted by an alanine residue. Particular substitutional variants of the Apo2L/TRAIL include those in which at least one amino acid is substituted by an alanine residue. These substitutional variants include those identified, for example, as "D203A"; "D218A" and "D269A." This nomenclature is used to identify Apo2L/TRAIL variants wherein the aspartic acid residues at positions 203, 218, and/or 269 (using the numbering shown in FIG. 1) are substituted by alanine residues. Optionally, the Apo2L variants may comprise one or more of the alanine substitutions which are recited in Table I of published PCT application WO 01/00832. Substitutional variants include one or more of the residue substitutions identified in Table I of WO 01/00832 published Jan. 4, 2001. The definition also encompasses a native sequence Apo2L/TRAIL isolated from an Apo2L/TRAIL source or prepared by recombinant or synthetic methods. The Apo2L/TRAIL of the invention includes the polypeptides referred to as Apo2L/TRAIL or TRAIL disclosed in PCT Publication Nos. WO97/01633 and WO97/25428. The terms "Apo2L/TRAIL" or "Apo2L" are used to refer generally to forms of the Apo2L/TRAIL which include monomer, dimer or trimer forms of the polypeptide. All numbering of amino acid residues referred to in the Apo2L sequence use the numbering according to FIG. 1, unless specifically stated otherwise. For instance, "D203" or "Asp203" refers to the aspartic acid residue at position 203 in the sequence provided in FIG. 1.

The term "Apo2L/TRAIL extracellular domain" or "Apo2L/TRAIL ECD" refers to a form of Apo2L/TRAIL which is essentially free of transmembrane and cytoplasmic domains. Ordinarily, the ECD will have less than 1% of such transmembrane and cytoplasmic domains, and preferably, will have less than 0.5% of such domains. It will be understood that any transmembrane domain(s) identified for the polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified. In preferred embodiments, the ECD will consist of a soluble, extracellular domain sequence of the polypeptide which is free of the transmembrane and cytoplasmic or intracellular domains (and is not membrane bound). Particular extracellular domain sequences of Apo-2L/TRAIL are described in PCT Publication Nos. WO97/01633 and WO97/25428.

The term "Apo2L/TRAIL monomer" or "Apo2L monomer" refers to a covalent chain of an extracellular domain sequence of Apo2L.

The term "Apo2L/TRAIL dimer" or "Apo2L dimer" refers to two Apo-2L monomers joined in a covalent linkage via a disulfide bond. The term as used herein includes free standing Apo2L dimers and Apo2L dimers that are within trimeric forms of Apo2L (i.e., associated with another, third Apo2L monomer).

The term "Apo2L/TRAIL trimer" or "Apo2L trimer" refers to three Apo2L monomers that are non-covalently associated.

The term "Apo2L/TRAIL aggregate" is used to refer to self-associated higher oligomeric forms of Apo2L/TRAIL, such as Apo2L/TRAIL trimers, which form, for instance, hexameric and nanomeric forms of Apo2L/TRAIL. Determination of the presence and quantity of Apo2L/TRAIL monomer, dimer, or trimer (or other aggregates) may be made using methods and assays known in the art (and using commercially available materials), such as native size exclusion HPLC ("SEC"), denaturing size exclusion using sodium dodecyl sulphate ("SDS-SEC"), reverse phase HPLC and capillary electrophoresis.

"Apo-2 ligand receptor" includes the receptors referred to in the art as "DR4" and "DR5" whose polynucleotide and polypeptide sequences are shown in FIGS. 2 and 3 respectively. Pan et al. have described the TNF receptor family member referred to as "DR4" (Pan et al., Science, 276:111-113 (1997); see also WO98/32856 published Jul. 30, 1998; WO 99/37684 published Jul. 29, 1999; WO 00/73349 published Dec. 7, 2000; U.S. Pat. No. 6,433,147 issued Aug. 13, 2002; U.S. Pat. No. 6,461,823 issued Oct. 8, 2002, and U.S. Pat. No. 6,342,383 issued Jan. 29, 2002). Sheridan et al., Science, 277:818-821 (1997) and Pan et al., Science, 277: 815-818 (1997) described another receptor for Apo2L/TRAIL (see also, WO98/51793 published Nov. 19, 1998; WO98/41629 published Sep. 24, 1998). This receptor is referred to as DR5 (the receptor has also been alternatively referred to as Apo-2; TRAIL-R, TR6, Tango-63, hAPO8, TRICK2 or KILLER; Screaton et al., Curr. Biol., 7:693-696 (1997); Walczak et al., EMBO J., 16:5386-5387 (1997); Wu et al., Nature Genetics, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/01255540 published Jul. 3, 2003; US 2002/0160446 published Oct. 31, 2002, US 2002/0048785 published Apr. 25, 2002; U.S. Pat. No. 6,569,642 issued May 27, 2003, U.S. Pat. No. 6,072,047 issued Jun. 6, 2000, U.S. Pat. No. 6,642,358 issued Nov. 4, 2003). As described above, other receptors for Apo-2L include DcR1, DcR2, and OPG (see, Sheridan et al., supra; Marsters et al., supra; and Simonet et al., supra). The term "Apo-2L receptor" when used herein encompasses native sequence receptor and receptor variants. These terms encompass Apo-2L receptor expressed in a variety of mammals, including humans. Apo-2L receptor may be endogenously expressed as occurs naturally in a variety of human tissue lineages, or may be expressed by recombinant or synthetic methods. A "native sequence Apo-2L receptor" comprises a polypeptide having the same amino acid sequence as an Apo-2L receptor derived from nature. Thus, a native sequence Apo-2L receptor can have the amino acid sequence of naturally-occurring Apo-2L receptor from any mammal. Such native sequence Apo-2L receptor can be isolated from nature or can be produced by recombinant or synthetic means. The term "native sequence Apo-2L receptor" specifically encompasses naturally-occurring truncated or secreted forms of the receptor (e.g., a soluble form containing, for instance, an extracellular domain sequence), naturally-occurring variant forms (e.g., alternatively spliced forms) and naturally-occurring allelic variants. Receptor variants may include fragments or deletion mutants of the native sequence Apo-2L receptor. FIG. 3A shows the 411 amino acid sequence of human DR5 as published in WO 98/51793 on Nov. 19, 1998. A transcriptional splice variant of human DR5 is known in the art. This DR5 splice variant encodes the 440 amino acid sequence of human DR5 shown in FIGS. 3B and 3C as published in WO 98/35986 on Aug. 20, 1998.

"Death receptor antibody" is used herein to refer generally to antibody or antibodies directed to a receptor in the tumor necrosis factor receptor superfamily and containing a death domain capable of signalling apoptosis, and such antibodies include DR5 antibody and DR4 antibody.

"DR5 receptor antibody", "DR5 antibody", or "anti-DR5 antibody" is used in a broad sense to refer to antibodies that bind to at least one form of a DR5 receptor or extracellular domain thereof. Optionally the DR5 antibody is fused or linked to a heterologous sequence or molecule. Preferably the heterologous sequence allows or assists the antibody to form higher order or oligomeric complexes. Optionally, the DR5 antibody binds to DR5 receptor but does not bind or cross-react with any additional Apo-2L receptor (e.g. DR4, DcR1, or DcR2). Optionally the antibody is an agonist of DR5 signalling activity.

Optionally, the DR5 antibody of the invention binds to a DR5 receptor at a concentration range of about 0.1 nM to about 20 mM as measured in a BIAcore binding assay. Optionally, the DR5 antibodies of the invention exhibit an Ic 50 value of about 0.6 nM to about 18 mM as measured in a BIAcore binding assay.

"DR4 receptor antibody", "DR4 antibody", or "anti-DR4 antibody" is used in a broad sense to refer to antibodies that bind to at least one form of a DR4 receptor or extracellular domain thereof. Optionally the DR4 antibody is fused or linked to a heterologous sequence or molecule. Preferably the heterologous sequence allows or assists the antibody to form higher order or oligomeric complexes. Optionally, the DR4 antibody binds to DR4 receptor but does not bind or cross-react with any additional Apo-2L receptor (e.g. DR5, DcR1, or DcR2). Optionally the antibody is an agonist of DR4 signalling activity.

Optionally, the DR4 antibody of the invention binds to a DR4 receptor at a concentration range of about 0.1 nM to about 20 mM as measured in a BIAcore binding assay. Optionally, the DR5 antibodies of the invention exhibit an Ic 50 value of about 0.6 nM to about 18 mM as measured in a BIAcore binding assay.

The term "agonist" is used in the broadest sense, and includes any molecule that partially or fully enhances, stimulates or activates one or more biological activities of Apo2L/TRAIL, DR4 or DR5, in vitro, in situ, or in vivo. Examples of such biological activities binding of Apo2L/TRAIL to DR4 or DR5, include apoptosis as well as those further reported in the literature. An agonist may function in a direct or indirect manner. For instance, the agonist may function to partially or fully enhance, stimulate or activate one or more biological activities of DR4 or DR5, in vitro, in situ, or in vivo as a result of its direct binding to DR4 or DR5, which causes receptor activation or signal transduction. The agonist may also function indirectly to partially or fully enhance, stimulate or activate one or more biological activities of DR4 or DR5, in vitro, in situ, or in vivo as a result of, e.g., stimulating another effector molecule which then causes DR4 or DR5 activation or signal transduction. It is contemplated that an agonist may act as an enhancer molecule which functions indirectly to enhance or increase DR4 or DR5 activation or activity. For instance, the agonist may enhance activity of endogenous Apo-2L in a mammal. This could be accomplished, for example, by pre-complexing DR4 or DR5 or by stabilizing complexes of the respective ligand with the DR4 or DR5 receptor (such as stabilizing native complex formed between Apo-2L and DR4 or DR5).

The term "biomarker" as used in the present application refers generally to a molecule, including a gene, protein, carbohydrate structure, or glycolipid, the expression of which in or on a mammalian tissue or cell can be detected by standard methods (or methods disclosed herein) and is predictive for a mammalian cell's or tissue's sensitivity to Apo2L/TRAIL or death receptor antibody. Such biomarkers contemplated by the present invention include but are not limited to "(1,3/1,4) fucosyltransferase" or "FUT3", "alpha (1,3) fucosyltransferase" or "FUT6", "Sialyl Lewis A", and "Sialyl Lewis X". Optionally, the expression of such a biomarker is determined to be higher than that observed for a control tissue or cell sample. Optionally, for example, the expression of such a biomarker will be determined in a PCR or FACS assay to be at least 50-fold, or preferably at least 100-fold higher in the test tissue or cell sample than that observed for a control tissue or cell sample. Optionally, the expression of such a biomarker will be determined in an IHC assay to score at least 2 or higher for staining intensity.

"(1,3/1,4) fucosyltransferase" or "FUT3" is used herein to refer to a molecule having structural features as described herein and optionally, catalyzing the transfer of a fucose residue from the donor substrate, GDP-fucose, to an acceptor substrate in an α3- or α4-linkage to GlcNAc (FUTs III-VII and IX). The DNA sequence and amino acid sequence for human FUT3 is provided in FIG. 4. These sequences correspond to GenBank Accession Number HSU27328 and are described for example in Kukowska-Latallo et al., Genes Dev. 1990 August;4(8):1288-303. FUTs generally are type II transmembrane glycoproteins residing in the Golgi vaccules, and typically composed of an N-terminal cytoplasmic tail, a membrane-spanning region, and a catalytic domain oriented lumenally in the Golgi apparatus. Between the membrane-spanning region and the catalytic domain is a region called the stem (Paulson and Colley, J. Biol. Chem., 264:17615-17618 (1989)).

"alpha (1,3) fucosyltransferase" or "FUT6" is used herein to refer to a molecule which structurally relates to, e.g, the DNA sequence and amino acid sequence for human FUT6 provided in FIG. 5. These sequences correspond to GenBank Accession Number HSU27333 and are described for example in Koszdin and Bowen, Biochem Biophys Res Commun. 1992 Aug. 31;187(1):152-7. FUT 6 is typically expressed in epithelial cells and in liver, kidney, and gastrointestinal tissues, specifically, stomach, jejunum and colon (and typically minimally expressed in spleen, lung and cervix uteri). FUT 6 is typically not detected in brain, adrenal cortex, or peripheral blood leukocytes.

"Sialyl Lewis A" is used herein to refer to a tetrasaccharide carbohydrate structure or antigen having the following sequence or structure, which may be membrane bound or in soluble form, circulating, for instance, in serum:

NeuAcα2-->3Galβ1-->3[Fucα1-->4]GlcNAcβ1-->R
(NeuAcalpha2-->3Galbeta1-->3(Fucalpha1-- >4)GlcNAc-beta1-->R)

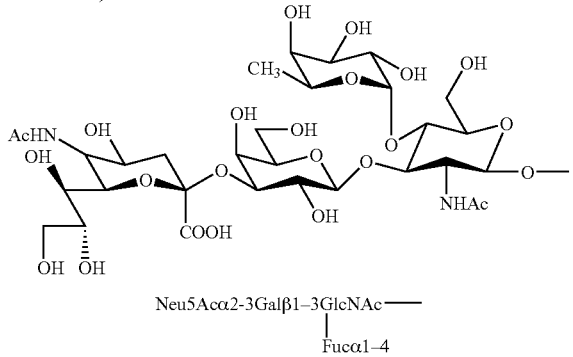

Neu5Acα2-3Galβ1-3GlcNAc——
|
Fucα1-4

"Sialyl Lewis X" is used herein to refer to tetrasaccharide carbohydrate structure or antigen having the following sequence or structure, which may be membrane bound or in soluble form, circulating, for instance, in serum:

NeuAcα2-->3Galβ1-->4 [Fucα1-->3]GlcNAcβ1-->R
(NeuAcalpha2-->3Galbeta1-- >4 (Fucalpha1-->3)GlcNAc-beta1-->R)

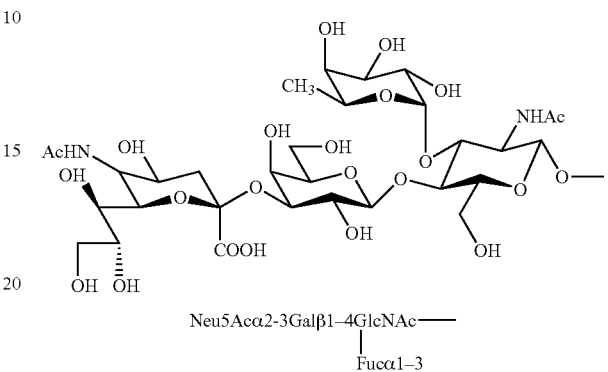

Neu5Acα2-3Galβ1-4GlcNAc——
|
Fucα1-3

By "subject" or "patient" is meant any single subject for which therapy is desired, including humans, cattle, dogs, guinea pigs, rabbits, chickens, insects and so on. Also intended to be included as a subject are any subjects involved in clinical research trials not showing any clinical sign of disease, or subjects involved in epidemiological studies, or subjects used as controls.

The term "mammal" as used herein refers to any mammal classified as a mammal, including humans, cows, horses, dogs and cats. In a preferred embodiment of the invention, the mammal is a human.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a primary or metastatic tumor. The tissue sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of immununohistochemical analysis or protocol one may use the results of IHC to determine whether a specific therapeutic regimen should be performed.

By "nucleic acid" is meant to include any DNA or RNA. For example, chromosomal, mitochondrial, viral and/or bacterial nucleic acid present in tissue sample. The term "nucleic acid" encompasses either or both strands of a double stranded nucleic acid molecule and includes any fragment or portion of an intact nucleic acid molecule.

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable or complementarity determining regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$).

By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the amino acid residues of an antibody which are responsible for antigen-binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196: 901-917 (1987)). "Framework" or "FR" residues are those variable domain residues other than the hypervariable region residues as herein defined.

An antibody "which binds" an antigen of interest is one capable of binding that antigen with sufficient affinity and/or avidity such that the antibody is useful as a therapeutic or diagnostic agent for targeting a cell expressing the antigen.

For the purposes herein, "immunotherapy" will refer to a method of treating a mammal (preferably a human patient) with an antibody, wherein the antibody may be an unconjugated or "naked" antibody, or the antibody may be conjugated or fused with heterologous molecule(s) or agent(s), such as one or more cytotoxic agent(s), thereby generating an "immunoconjugate".

An "isolated" antibody is one which has been identified and separated and/or recovered from a component of its natural environment. Contaminant components of its natural environment are materials which would interfere with diagnostic or therapeutic uses for the antagonist or antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The expression "effective amount" refers to an amount of an agent (e.g. Apo2L/TRAIL, anti-DR4 or DR5 antibody etc.) which is effective for preventing, ameliorating or treating the disease or condition in question.

The terms "treating", "treatment" and "therapy" as used herein refer to curative therapy, prophylactic therapy, and preventative therapy. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors; platelet-growth factor; transforming growth factors (TGFs) such as TGF-α and TGF-β; insulin-like growth factor-I and -II; erythropoietin (EPO); osteoinductive factors; interferons such as interferon-α, -β, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-11, IL-12, IL-13, IL-17; and other polypeptide factors including LIF and kit ligand (KL). As used herein, the term cytokine includes proteins from natural sources or from recombinant cell culture and biologically active equivalents of the native sequence cytokines.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammaI1 and calicheamicin phi1, see, e.g., Agnew, Chem Intl. Ed. Engl., 33:183-186 (1994); dynemicin, including dynemicin A; bisphosphonates, such as clodronate; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest.

Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995), especially p. 13.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays (such as Alamar blue assays or MTT assays), FACS analysis, caspase activation, DNA fragmentation (see, for example, Nicoletti et al., *J. Immunol. Methods*, 139:271-279 (1991), and poly-ADP ribose polymerase, "PARP", cleavage assays known in the art.

As used herein, the term "disorder" in general refers to any condition that would benefit from treatment with the compositions described herein, including any disease or disorder that can be treated by effective amounts of Apo2L/TRAIL, an anti-DR4 antibody, and/or an anti-DR5 antibody. This includes chronic and acute disorders, as well as those pathological conditions which predispose the mammal to the disorder in question. Non-limiting examples of disorders to be treated herein include benign and malignant cancers; inflammatory, angiogenic, and immunologic disorders, autoimmune disorders, arthritis (including rheumatoid arthritis), multiple sclerosis, and HIV/AIDS.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, neuroblastoma, pancreatic cancer, glioblastoma multiforme, cervical cancer, brain cancer, stomach cancer, bladder cancer, hepatoma, breast cancer, colon carcinoma, and head and neck cancer.

The term "immune related disease" means a disease in which a component of the immune system of a mammal causes, mediates or otherwise contributes to morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

"Autoimmune disease" is used herein in a broad, general sense to refer to disorders or conditions in mammals in which destruction of normal or healthy tissue arises from humoral or cellular immune responses of the individual mammal to his or her own tissue constituents. Examples include, but are not limited to, lupus erythematous, thyroiditis, rheumatoid arthritis, psoriasis, multiple sclerosis, autoimmune diabetes, and inflammatory bowel disease (IBD).

The term "tagged" when used herein refers to a chimeric molecule comprising an antibody or polypeptide fused to a "tag polypeptide". The tag polypeptide has enough residues to provide an epitope against which an antibody can be made or to provide some other function, such as the ability to oligomerize (e.g. as occurs with peptides having leucine zipper domains), yet is short enough such that it generally does not interfere with activity of the antibody or polypeptide. The tag polypeptide preferably also is fairly unique so that a tag-specific antibody does not substantially cross-react with other epitopes. Suitable tag polypeptides generally have at least six amino acid residues and usually between about 8 to about 50 amino acid residues (preferably, between about 10 to about 20 residues).

The term "divalent metal ion" refers to a metal ion having two positive charges. Examples of divalent metal ions include but are not limited to zinc, cobalt, nickel, cadmium, magnesium, and manganese. Particular forms of such metals that may be employed include salt forms (e.g., pharmaceutically acceptable salt forms), such as chloride, acetate, carbonate, citrate and sulfate forms of the above mentioned divalent metal ions. Optionally, a divalent metal ion for use in the present invention is zinc, and preferably, the salt form, zinc sulfate or zinc chloride "Isolated," when used to describe the various peptides or proteins disclosed herein, means peptide or protein that has been identified and separated and/or recovered from a component of its natural environment. Contaminant components of its natural environment are materials that would typically interfere with diagnostic or therapeutic uses for the peptide or protein, and may include enzymes, hormones, and other proteinaceous or non-proteinaceous solutes. In preferred embodiments, the peptide or protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain, or (3) to homogeneity by mass spectroscopic or peptide mapping techniques. Isolated material includes peptide or protein in situ within recombinant cells, since at least one component of its natural environment will not be present. Ordinarily, however, isolated peptide or protein will be prepared by at least one purification step.

"Percent (%) amino acid sequence identity" with respect to the sequences identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can be obtained using the sequence comparison computer program, ALIGN-2, which was authored by Genentech, Inc. and the source code of which has been filed with user documentation in the U.S. Copyright Office, Washington, D.C., 20559, registered under the U.S. Copyright Registration No. TXU510087. The ALIGN-2 program is publicly available through Genentech, Inc., South San Francisco, Calif. All sequence comparison parameters are set by the ALIGN-2 program and do not vary.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"High stringency conditions", as defined herein, are identified by those that: (1) employ low ionic strength and high temperature for washing; 0.015 M sodium chloride/0.0015 M sodium citrate/0.1% sodium dodecyl sulfate at 50° C.; (2) employ during hybridization a denaturing agent; 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "primer" or "primers" refers to oligonucleotide sequences that hybridize to a complementary RNA or DNA target polynucleotide and serve as the starting points for the stepwise synthesis of a polynucleotide from mononucleotides by the action of a nucleotidyltransferase, as occurs for example in a polymerase chain reaction.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and carry out ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)). FcRs herein include polymorphisms such as the genetic dimorphism in the gene that encodes FcγRIIIa resulting in either a phenylalanine (F) or a valine (V) at amino acid position 158, located in the region of the receptor that binds to IgG1. The homozygous valine FcγRIIIa (FcγRIIIa-158V) has been shown to have a higher affinity for human IgG1 and mediate increased ADCC in vitro relative to homozygous phenylalanine FcγRIIIa (FcγRIIIa-158F) or heterozygous (FcγRIIIa-158F/V) receptors.

"Complement dependent cytotoxicity" or "CDC" refer to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

II. Typical Methods and Materials of the Invention

The methods and assays disclosed herein are directed to the examination of expression of one or more biomarkers in a mammalian tissue or cell sample, wherein the determination of that expression of one or more such biomarkers is predictive or indicative of whether the tissue or cell sample will be sensitive to apoptosis-inducing agents such as Apo2L/TRAIL and anti-DR5 agonist antibodies. The methods and assays include those which examine expression of biomarkers such as certain fucosyltransferases, in particular fucosyltransferase 3 (FUT3) and/or fucosyltransferase 6 (FUT6), as well as sialyl Lewis A and/or X antigens.

As discussed above, there are some populations of diseased human cell types (such as certain populations of cancer cells) which are resistant to apoptosis induction. It is therefore believed that the disclosed methods and assays can provide for convenient, efficient, and potentially cost-effective means to obtain data and information useful in assessing appropriate or effective therapies for treating patients. For example, a patient having been diagnosed with cancer or an immune related condition could have a biopsy performed to obtain a tissue or cell sample, and the sample could be examined by way of various in vitro assays to determine whether the patient's cells would be sensitive to a therapeutic agent such as Apo2L/TRAIL or death receptor antibody.

The invention provides methods for predicting the sensitivity of a mammalian tissue or cell sample (such as a cancer cell) to Apo2L/TRAIL or a death receptor agonist antibody. In the methods, a mammalian tissue or cell sample is obtained and examined for expression of one or more biomarkers. The methods may be conducted in a variety of assay formats, including assays detecting MRNA expression, enzymatic assays detecting presence of enzymatic activity, and immunohistochemistry assays. Determination of expression of such biomarkers in said tissues or cells will be predictive that such tissues or cells will be sensitive to the apoptosis-inducing activity of Apo2L/TRAIL and/or death receptor antibody. Applicants surprisingly found that the expression of such particular biomarkers correlates with the sensitivity of such tissues and cells to apoptosis-inducing agents such as Apo2L/TRAIL and death receptor agonist antibodies.

As discussed below, expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA) (to examine, for example, levels of protein expression), biochemical enzymatic activity assays, in situ hybridization, Northern analysis and/or PCR analysis of mRNAs, and genomic Southern analysis (to examine, for example, gene deletion or amplification), as well as any one of the wide variety of assays that can be performed by gene and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis).

The protocols below relating to detection of particular biomarkers, such as fucosyltransferase 3 (FUT3), fucosyltransferase 6 (FUT6), Sialyl Lewis A, and Sialyl Lewis X, in a sample are provided below for illustrative purposes.

Optional methods of the invention include protocols which examine or test for presence of sialyl Lewis A and/or sialyl Lewis X proteins in a mammalian tissue or cell sample. A variety of methods for detecting sialyl Lewis A and/or sialyl Lewis X-related protein can be employed and include, for example, immunohistochemical analysis, immunoprecipitation, Western blot analysis, molecular binding assays, ELISA, ELIFA, fluorescence activated cell sorting (FACS) and the like. For example, an optional method of detecting the expression of sialyl Lewis A and/or sialyl Lewis X-related protein in a tissue or sample comprises contacting the sample with a sialyl Lewis A and/or sialyl Lewis X antibody, a sialyl Lewis A and/or sialyl Lewis X-reactive fragment thereof, or a recombinant protein containing an antigen binding region of a sialyl Lewis A and/or sialyl Lewis X antibody; and then detecting the binding of sialyl Lewis A and/or sialyl Lewis X-related protein in the sample.

In particular embodiments of the invention, the expression of sialyl Lewis A and/or sialyl Lewis X proteins in a sample is examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. The sample can be obtained by a variety of procedures known in the art including, but not limited to surgical excision, aspiration or biopsy. The tissue may be fresh or frozen. In one embodiment, the sample is fixed and embedded in paraffin or the like.

The tissue sample may be fixed (i.e. preserved) by conventional methodology (See e.g., "Manual of Histological Staining Method of the Armed Forces Institute of Pathology," 3$^{rd}$ edition (1960) Lee G. Luna, HT (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Optionally, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen (e.g., sialyl Lewis A and/or sialyl Lewis X) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immnunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this.

For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Optionally, the antibodies employed in the IHC analysis to detect expression of sialyl Lewis A or anti-sialyl Lewis X, are anti-sialyl Lewis A and anti-sialyl Lewis X antibody, respectively. Optionally, the anti-sialyl Lewis A and the anti-sialyl Lewis X antibody is a monoclonal antibody. Anti-sialyl Lewis A and an anti-sialyl Lewis X antibodies are readily available in the art, including from various commercial sources.

Specimens thus prepared may be mounted and coverslipped. Slide evaluation is then determined, e.g. using a microscope, and staining intensity criteria, routinely used in the art, may be employed. Where the antigen is sialyl Lewis A and/or sialyl Lewis X protein, staining intensity criteria may be evaluated as follows:

TABLE 1

| Staining Pattern | Score |
| --- | --- |
| No staining is observed in cells. | 0 |
| Faint/barely perceptible staining is detected in more than 10% of cells. | 1+ |
| Weak to moderate staining is observed in more than 10% of the cells. | 2+ |
| Moderate to strong staining is observed in more than 10% of the cells. | 3+ |

Typically, a staining pattern score of about 2+ or higher in such an IHC assay is believed to be predictive or indicative of sensitivity of a mammalian cell (such as a mammalian cancer cell) to Apo2L/TRAIL or a death receptor agonist antibody.

In alternative methods, the sample may be contacted with an antibody specific for said biomarker under conditions sufficient for an antibody-biomarker complex to form, and then detecting said complex. The presence of the biomarker may be accomplished in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labelled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

It is contemplated that the above described techniques may also be employed to detect expression of FUT3 or FUT 6 polypeptides.

Methods of the invention further include protocols which examine the presence and/or expression of mRNAs, such as FUT3 and/or FUT6 mRNAs, in a tissue or cell sample. Methods for the evaluation of mRNAs in cells are well known and include, for example, hybridization assays using complementary DNA probes (such as in situ hybridization using labeled FUT3 and/or FUT6 riboprobes, Northern blot and related techniques) and various nucleic acid amplification assays (such as RT-PCR using complementary primers specific for FUT3 and/or FUT6, and other amplification type detection methods, such as, for example, branched DNA, SISBA, TMA and the like).

Tissue or cell samples from mammals can be conveniently assayed for, e.g., FUT3 and/or FUT6 mRNAs using Northern, dot blot or PCR analysis. For example, RT-PCR assays such as quantitative PCR assays are well known in the art. In an illustrative embodiment of the invention, a method for detecting an FUT3 and/or FUT6 mRNA in a biological sample comprises producing cDNA from the sample by reverse transcription using at least one primer; amplifying the cDNA so produced using an FUT3 and/or FUT6 polynucleotide as sense and antisense primers to amplify FUT3 and/or FUT6 cDNAs therein; and detecting the presence of the amplified FUT3 and/or FUT6 cDNA. In addition, such methods can include one or more steps that allow one to determine the levels of FUT3 and/or FUT6 mRNA in a biological sample (e.g. by simultaneously examining the levels a comparative control mRNA sequence of a "housekeeping" gene such as an actin family member). Optionally, the sequence of the amplified FUT3 and/or FUT6 cDNA can be determined.

Material embodiments of this aspect of the invention include FUT3 and/or FUT6 primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of FUT3 and/or FUT6 polynucleotides in a sample and as a means for detecting a cell expressing FUT3 and/or FUT6 proteins. As will be understood by the skilled artisan, a great many different primers and probes may be prepared based on the sequences provided in herein and used effectively to amplify, clone and/or determine the presence and/or levels of FUT3 and/or FUT6 mRNAs.

Optional methods of the invention include protocols which examine or detect mRNAs, such as FUT3 and FUT6 or other fucosyltransferase mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, 5,445, 934, and 5,807,522, Lockart, Nature Biotechnology, 14:1675-1680 (1996); Cheung, V. G. et al., Nature Genetics 21(Suppl): 15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1. preparation of fluorescently labeled target from RNA isolated from the sample, 2. hybridization of the labeled target to the microarray, 3. washing, staining, and scanning of the array, 4. analysis of the scanned image and 5. generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

The expression of a selected biomarker may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. By way of example, these methods may be employed to detect deletion of amplification of the FUT3 and/or FUT6 genes.

Additionally, one can examine the methylation status of the biomarker, such as the FUT3 and/or FUT6 gene, in a tissue or cell sample. Aberrant demethylation and/or hypermethylation of CpG islands in gene 5' regulatory regions frequently occurs in immortalized and transformed cells, and can result in altered expression of various genes. A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995; De Marzo et al., Am. J. Pathol. 155(6): 1985-1992 (1999); Brooks et al, Cancer Epidemiol. Biomarkers Prev., 1998, 7:531-536); and Lethe et al., Int. J. Cancer 76(6): 903-908 (1998).

Expression of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

Figure 11:
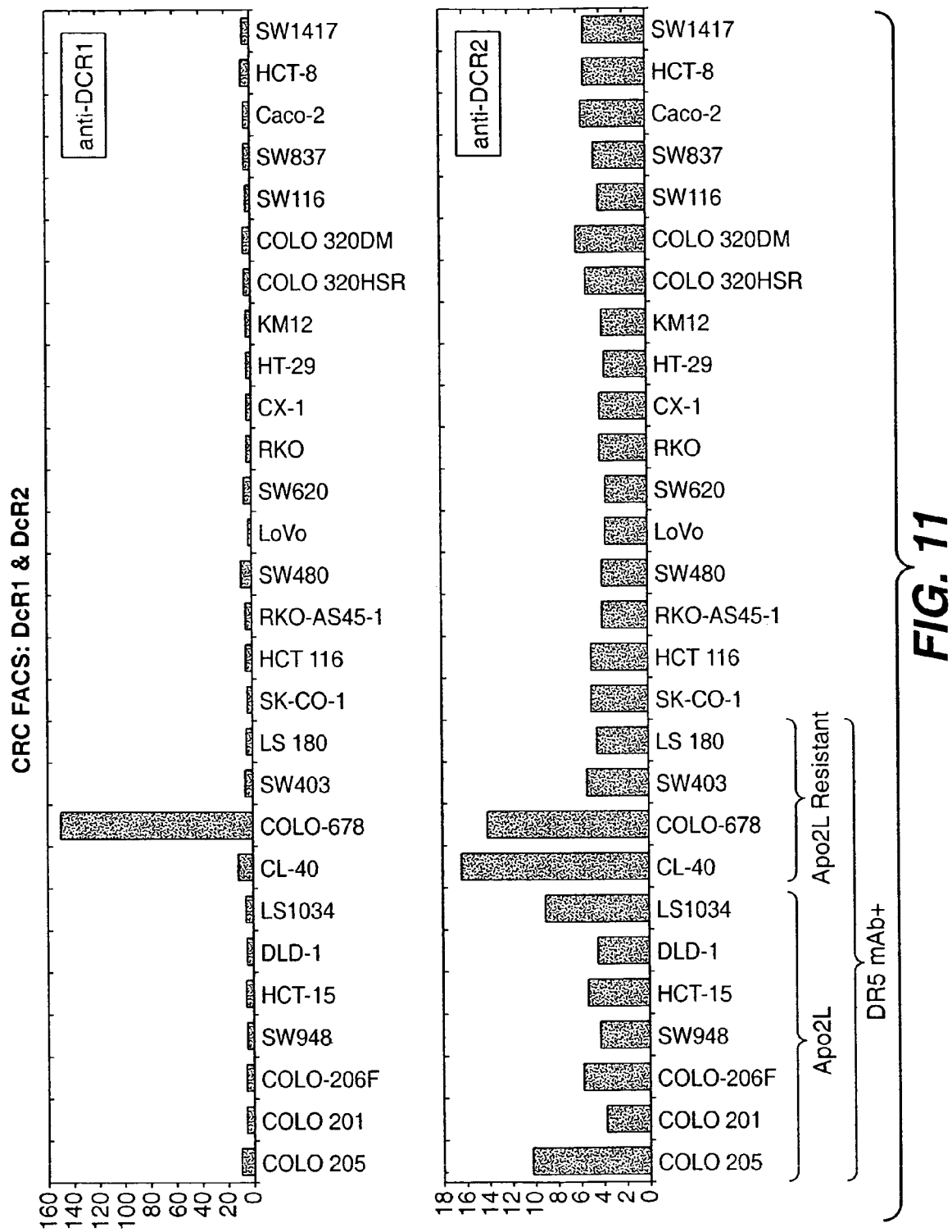
FIG. 11 provides a comparison of various colon or colorectal cancer cell lines for expression of DcR1 or DcR2 receptors (as determined by FACS) and the status (sensitive or resistant) of certain cell lines to Apo2L or DR5 antibody.

In the methods of the present invention, it is contemplated that the tissue or cell sample may also be examined for the expression of Apo2L/TRAIL or receptors in the sample which bind Apo2L/TRAIL or death receptor antibody. As described above and in the art, it is presently believed Apo2L/TRAIL binds to at least five different receptors: DR4, DR5, DcR1, DcR2, and OPG. Using methods known in the art, including those described herein, the expression of Apo2L/TRAIL, DR4, DR5, DcR1, DcR2 and/or OPG can be detected on the MRNA level and on the protein level. As shown in FIGS. 10 and 11, data suggests that examining the tissue or cell sample for expression of DcR1 and/or DcR2 receptors may give further information as to whether the tissue or cell sample will be sensitive to either Apo2L/TRAIL or death receptor antibody. By way of example, the IHC techniques described above may be employed to detect the presence of one of more such molecules in the sample. It is contemplated that in methods in which a tissue or sample is being examined not only for the presence of a FUT or Lewis antigen marker, but also for the presence, e.g., DR4, DR5 or DcR1, separate slides may be prepared from the same tissue or sample, and each slide tested with a reagent specific for each specific biomarker or receptor. Alternatively, a single slide may be prepared from the tissue or cell sample, and antibodies directed to each biomarker or receptor may be used in connection with a multi-color staining protocol to allow visualization and detection of the respective biomarkers or receptors.

Subsequent to the determination that the tissue or cell sample expresses one or more of the biomarkers indicating the tissue or cell sample will be sensitive to the activity of Apo2L/TRAIL or death receptor antibody, it is contemplated that an effective amount of the Apo2L/TRAIL or death receptor antibody may be administered to the mammal to treat a disorder, such as cancer or immune related disorder which is afflicting the mammal. Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like. Immune related diseases can also be readily identified.

The Apo2L/TRAIL or death receptor antibody can be administered in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Optionally, administration may be performed through mini-pump infusion using various commercially available devices.

Effective dosages and schedules for administering Apo2L/TRAIL or death receptor antibody may be determined empirically, and making such determinations is within the skill in the art. Single or multiple dosages may be employed. It is presently believed that an effective dosage or amount of Apo2L/TRAIL used alone may range from about 1 μg/kg to about 100 mg/kg of body weight or more per day. Interspecies scaling of dosages can be performed in a manner known in the art, e.g., as disclosed in Mordenti et al., *Pharmaceut. Res.*, 8:1351 (1991).

When in vivo administration of Apo2L/TRAIL is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

It is contemplated that yet additional therapies may be employed in the methods. The one or more other therapies may include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors which are known in the art and defined further with particularity above. It is contemplated that such other therapies may be employed as an agent separate from the Apo2L/TRAIL or death receptor antibody. In addition, therapies based on therapeutic antibodies that target tumor antigens such as Rituxan™ or Herceptin™ as well as anti-angiogenic antibodies such as anti-VEGF.

Preparation and dosing schedules for chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the Apo2L/TRAIL or death receptor antibody, or may be given simultaneously therewith.

It may be desirable to also administer antibodies against other antigens, such as antibodies which bind to CD20, CD11a, CD18, CD40, ErbB2, EGFR, ErbB3, ErbB4, vascular endothelial factor (VEGF), or other TNFR family members (such as OPG, TNFR1, TNFR2, GITR, Apo-3, TACI, BCMA, BR3). Alternatively, or in addition, two or more antibodies binding the same or two or more different antigens disclosed herein may be co-administered to the patient. Sometimes, it may be beneficial to also administer one or more cytokines to the patient. Following administration, treated cells in vitro can be analyzed. Where there has been in vivo treatment, a treated mammal can be monitored in various ways well known to the skilled practitioner. For instance, tumor cells can be examined pathologically to assay for necrosis or serum can be analyzed for immune system responses.

For use in the applications described or suggested above, kits or articles of manufacture are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a FUT3 and/or FUT6 protein or a FUT3 and/or FUT6 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the invention have a number of embodiments. A typical embodiment is a kit comprising a container, a label on said container, and a composition contained within said container; wherein the composition includes a primary antibody that binds to a FUT3 and/or FUT6 polypeptide sequence, the label on said container indicates that the composition can be used to evaluate the presence of FUT3 and/or FUT6 proteins in at least one type of mammalian cell, and instructions for using the FUT3 and/or FUT6 antibody for evaluating the presence of FUT3 and/or FUT6 proteins in at least one type of mammalian cell. The kit can further comprise a set of instructions and materials for preparing a tissue sample and applying antibody and probe to the same section of a tissue sample. The kit may include both a primary and secondary antibody, wherein the secondary antibody is conjugated to a label, e.g., an enzymatic label.

Another embodiment is a kit comprising a container, a label on said container, and a composition contained within said container; wherein the composition includes a polynucleotide that hybridizes to a complement of the FUT3 and/or FUT6 polynucleotide under stringent conditions, the label on said container indicates that the composition can be used to evaluate the presence of FUT3 and/or FUT6 in at least one type of mammalian cell, and instructions for using the FUT3 and/or FUT6 polynucleotide for evaluating the presence of FUT3 and/or FUT6 RNA or DNA in at least one type of mammalian cell.

Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

EXAMPLES

Various aspects of the invention are further described and illustrated by way of the examples that follow, none of which are intended to limit the scope of the invention.

Methods and Materials:

Cell Culture and Cell Lines.

The following human colorectal adenocarcinoma cell lines: HCT-8, COLO 205, HCT 116, SW403, LoVo, SW948, Caco-2, COLO 201, SW1417, DLD-1, CX-1, HCT-15, LS 180, RKO, RKO-AS45-1, SK-CO-1, SW480, SW620, SW837, CL-40, COLO-206F, COLO 320DM, COLO 320HSR, COLO-678, HT-29, KM12, LS1034, SW1116 were obtained from ATCC Depository (Manassas, Va.), DSMZ (German Collection of Microorganisms and Cell Cultures), JCRB (Japanese Cell Resources Bank) or ECACC (European Collection of Cell Cultures) and cultured in RPMI-1640 media supplemented with 10% heat inactivated fetal bovine serum, 2 mM L-glutamine and 10 mM HEPES.

Cytotoxicity Assays.

The MTT assay (CellTiter 96® Non-Radioactive Cell Proliferation Assay from Promega), which is a colorimetric assay based on the ability of viable cells to reduce a soluble yellow tetrazolium salt (MTT) to blue formazan crystals), was used to determine the amount of viable cells after treatment with Apo2L/TRAIL or DR5 antibody. The MTT assay was performed by the addition of a premixed optimized dye solution to culture wells of a 96-well plate containing various concentrations (0 to 1000 ng/ml) of Apo2L/TRAIL or DR5 antibody. During a 4-hour incubation, living cells convert the tetrazolium component of the dye solution into a formazan product. The solubilization/stop solution was then added to the culture wells to solubilize the formazan product, and the absorbance at 570 nm was recorded using a 96-well plate reader (SpectraMax). The 570 nm absorbance reading is directly proportional to the number of cells normally used in proliferation assays. Although the absorbance maximum for the formazan product is 570 nm and pure solutions appear blue, the color at the end of the assay may not be blue and depends on the quantity of formazan present relative to other components (including serum, acidified phenol red and unreduced MTT) in the culture medium.

Cell numbers were optimized by performing a cell titration to produce an assay signal near the high end of the linear range of the assay. Since different cell types have different levels of metabolic activity, this was done for each cell line separately. For most tumor cells examined, 5,000 cells per well to 20,000 cells per well were used.

The following is a step by step description of the assays employed:

1. Cells used for bioassay were from stock cultures.
2. Determination of cell number and trypan blue viability, and suspension of the cells to a final number of 5,000 to 20,000 cells per well.
3. Dispensed 50 µl of the cell suspension into 96-well plate.
4. Incubation of the plates at 37° C. in a humidified 5% $CO_2$ atmosphere over night.
5. Addition of 50 µl culture medium containing various concentrations ranging from 0 to 1000 ng/ml of Apo2L/TRAIL or DR5 antibody to samples of the 96-well plate. The controls were 50 µl of culture medium (without Apo2L/TRAIL or DR5 antibody) and 100 µl culture medium (without cells). Every experiment was performed in a triplicate set of wells and at three independent days. The total volume of the wells was 100 µl/well.
6. Incubation of the plates at 37° C. for 72 hours in a humidified 5% $CO_2$ atmosphere.
7. Addition of 15 µl of dye solution to each well.
8. Incubation of the plates at 37° C. for up to 4 hours in a humidified 5% $CO_2$ atmosphere.
9. Addition of 100 µl of the solubilization/stop solution to each well.
10. Incubation of the plates overnight at 37° C. overnight.
11. Record the absorbance at 570 nm wavelength using a 96-well plate reader. A reference wavelength of 750 nm was used to reduce background contributed by cell debris, fingerprints and other nonspecific absorbance.
12. The average of the absorbance values for the negative control was used as a blank value and subtracted from all other readings. The average of the absorbance values for each concentration of Apo2L/TRAIL or DR5 antibody was divided by the average of the absorbance values of the positive control (100% viable cells—untreated) to calculate the amount of viable cells (in %).
13. Percent viable cells (Y axis) versus concentration of Apo2L/TRAIL or DR5 antibody (X axis, log scale) was plotted and the IC50 value was determined by locating the X-axis value (ng/ml) corresponding to 50% viable cells.

Affymetrix Labeling Protocol

An OD260/280 reading was taken for all samples, and samples were run on the BioAnalyzer. 5 µg high quality Total RNA was used.

A. First Strand cDNA Synthesis:

1. Primer Hybridization

| | | |
|---|---|---|
| DEPC-H2O | x µl | Mix by vortexing. Quick spin. |
| RNA (5 ug) | y µl | Incubate at 70° C. for 10 minutes. |
| Spike (1:4 dil of stock for 5 ug) | 1 µl | Quick spin and put on ice |
| T7-(dT)24 primer | 1 µl | |
| volume | 12 µl | |

2. Temperature Adjustment

| | | |
|---|---|---|
| 5X -1st strand cDNA buffer | 4 µl | |
| Add | 7 µl | (of the mix to the left) to each sample. |
| 0.1 M DTT | 2 µl | Mix by vortexing. Quick spin. |
| 10 mM dNTP mix | 1 µl | Incubate at 42° C. for 2 minutes. |
| volume | 7 µl | |

3. First Strand Synthesis

| | | |
|---|---|---|
| Add | 1 µl | SSII RT to each sample. |
| SSII RT | 1 µl | Mix by pipetting up and down -OR- vortex lightly. |
| Quick spin. | | |
| Total volume | 20 µl | Incubate at 42° C. for 1 hour. |

B. Second Strand cDNA Synthesis
1. Place First Strand reactions on ice. Centrifuge briefly to bring down condensation on sides of tube.
2. Make the following Second strand master-mix.

| | |
|---|---|
| DEPC-treated H2O | 91 µl |
| 5X -2nd Strand Reaction Buffer | 30 µl |
| 10 mM dNTP mix | 3 µl |
| 10 U/µl DNA Ligase | 1 µl |
| 10 U/µl DNA Polymerase I | 4 µl |
| 2 U/µl RNase H | 1 µl |
| Total volume | 130 µl |

3. Add 130 µl Second strand master-mix to the 20 µl First strand cDNA. (Final volume=150 µl)
4. Mix by pipetting up and down —OR— by vortexing lightly. Quick spin.
5. Incubate at 16° C. for 2 hours in a cooling water bath.
6. Add 2 µl [10 U] T4 DNA Polymerase. Mix by pipetting up and down —OR—vortex lightly. Quick spin.
7. Incubate for 5 minutes at 16° C.
8. Add 10 µl 0.5 M EDTA. Vortex lightly. Quick spin.
9. Proceed to cleanup procedure for cDNA —OR— store at −20° C. for later use.

Cleanup of Double-Stranded cDNA (GeneChip Sample Cleanup Module)
1. Add 600 µl cDNA Binding Buffer to the 162 µl final double-stranded cDNA synthesis preparation.
   Mix by vortexing for 3 seconds.
2. Check that the color of the mixture is yellow (similar to cDNA Binding Buffer w/o the cDNA synthesis reaction). If the color of the mixture is orange or violet, add 10 µl of 3 M sodium acetate, pH5.0 and mix.
   The color of the mixture will turn to yellow.
3. Apply 500 µl of the sample to the cDNA Cleanup Spin Column sitting in a 2 ml Collection Tube, and centrifuge for 1 minute at ≧8,000×g (≧10,000 rpm). Discard flow-through as hazardous waste.
4. Reload the spin column with the remaining mixture (262 µl) and centrifuge as above.
   Discard flow-through as hazardous waste and discard the Collection Tube.
5. Transfer spin column into a new 2 ml Collection Tube (supplied). Pipet 750 µl cDNA Wash Buffer onto the spin column. Centrifuge for 1 minute at ≧8,000×g (≧10,000 rpm).
   Discard flow-through.
6. Open the cap of the spin column and centrifuge for 5 minutes at maximum speed (≦25,000×g). Place
   columns into the centrifuge using every second bucket. Position caps over the adjoining bucket so that
   they are oriented in the opposite direction to the rotation, i.e., if rotation is clockwise, orient caps
   in a counter-clockwise direction. This avoids damage to caps.
   Discard flow-through and Collection Tube.
7. Transfer spin column into a 1.5 ml Collection Tube. Pipet 10 µl of cDNA Elution Buffer directly onto the spin
   column membrane. Ensure that the cDNA Elution buffer is dispensed directly onto the membrane.
   Incubate for 1 minute at room temperature and centrifuge 1 minute at max. speed (≦25,000×g) to elute.

Setting Up and Running the IVT Reaction
Enzo: Bioarray HighYield RNA transcript Labeling Kit (Part No. 900182)
1. Use 10 µl of the Cleaned-up Double-stranded cDNA
2. Make the following IVT master-mix:

| | |
|---|---|
| Distilled or Deionized H2O | 12 µl |
| 10X HY Reaction buffer | 4 µl |
| 10X Biotin labeled Ribonucleotides | 4 µl |
| 10X DTT | 4 µl |
| 10X RNase Inhibitor Mix | 4 µl |
| 20X T7 RNA Polymerase | 2 µl |
| Total volume: | 30 µl |

3. Add 30 µl of the IVT master-mix to 10 µl double-stranded cDNA. (Total volume =40 µl)
4. Mix by pipetting up and down —OR— by vortexing lightly. Quick spin.
5. Immediately place the tube in a 37° C. water bath. Incubate for 5 hours.
6. Store at −20° C. if not purifying RNA immediately.

Cleanup of Biotin-Labeled cRNA (GeneChip Sample Cleanup Module)
1. Add 60 µl H2O to the IVT reaction and mix by vortexing for 3 seconds.
2. Add 350 µl IVT cRNA Binding Buffer to the sample, mix by vortexing for 3 seconds.
3. Add 250 µl ethanol (96-100%) to the lysate, and mix well by pipetting. Do not centrifuge.
4. Apply sample (700 µl) to the IVT cRNA Cleanup Spin Column sitting in a 2 ml collection tube.
   Centrifuge for 15 seconds at ≧8,000×g (≧10,000 rpm).
5. Pass the eluate through the column once more.
   Centrifuge for 15 seconds at ≧8,000×g (≧10,000 rpm).
   Discard the flow-through as hazardous waste and discard the collection tube.
6. Transfer the spin column into a new 2-ml collection tube (supplied).
7. Add 500 µl IVT cRNA Wash Buffer and centrifuge for 15 seconds at ≧8,000×g (≧10,000 rpm) to wash.
   Discard the flow-through.
8. Pipet 500 µl 80% (v/v) ethanol onto the spin column, and centrifuge for 15 seconds at
   ≧8,000×g (≧10,000 rpm). Discard flow-though.
9. Open the cap of the spin column and centrifuge for 5 minutes at max speed (≦25,000×g).
   Discard flow-through and Collection Tube.
10. Transfer the spin column into a new 1.5 ml collection tube.
11. Pipet 11 µl RNase-free water directly onto the spin column membrane.

Let stand for 1 minute.
   Centrifuge for 1 minute at maximum speed (≦25,000×g) to elute.
12. Pipet 10 µl RNase-free water directly onto the spin column membrane.

Let stand for 1 minute.
   Centrifuge for 1 minute at maximum speed (≦25,000×g) to elute.

Quantifying the cRNA (IVT Product)
Use spectrophotometric analysis to determine the RNA yield. Apply the convention that 1 OD at 260 nm equals 40 µg/ml RNA.

Check the OD at 260 nm and 280 nm to determine sample concentration and purity.

Maintain the A260/A280 ratio close to 2.0 for pure RNA (ratios between 1.9 and 2.1 are acceptable). For quantification of cRNA when using total RNA as starting material, an adjusted cRNA yield must be calculated to reflect carryover of unlabeled total RNA. Using an estimate of 100% carryover, use the formula below to determine adjusted cRNA yield:

adjusted cRNA yield=RNAm−(total RNAi)(y)
RNAm=amount of cRNA measured after IVT (µg)
total RNAi=starting amount of total RNA (µg)
y=fraction of cDNA reaction used in IVT Fragmenting the cRNA for Target Preparation For fragmentation, use the adjusted cRNA concentration.

1. Add 2 µl of 5× Fragmentation Buffer for every 8 µl of RNA plus H2O.

| | |
|---|---|
| 20 µg cRNA | 1 to 32 µl |
| 5X Fragmentation Buffer | 8 µl |
| RNase-free water to | 40 µl |
| Total volume: | 40 µl |

2. Incubate at 94° C. for 30 minutes. Immediately, put on ice following the incubation.

Preparing the Hybridization Target

1. Heat the 20X Eukaryotic Hybridization Controls and the Oligo B2 for 5 minutes at 65° C.

Affymetrix GeneChip Eukaryotic Hybridization Control Kit, Part #900362 (for 150 rxns)

2. Lightly vortex, spin down
3. Master mix (Assuming the fragmented cRNA concentration is 0.5 µg/µl):

| | Standard Array (µl) | Final Conc. |
|---|---|---|
| Fragmented cRNA 15 µg | 30 | 0.05 µg/µl |
| Oligo B2 (3 nM) | 5 | 50 pM |
| 20x Control Spike (Bio B, C, D, Cre) | 15 | 1.5, 5, 25, 100 pM |
| Herring Sperm DNA | 3 | 0.1 mg/ml |
| Acetylated BSA | 3 | 0.5 mg/ml |
| Hu cot-1 DNA (1 mg/ml) | 30 | 0.1 mg/ml |
| 2X MES Hyb Buffer | 150 | 1X |
| H2O | 64 | |
| Final Volume | 300 | |

4. Aliquot 270 µl master mix into tubes and add 30 µl of fragmented cRNA to each. This is the Hybridization Mix.
5. Equilibrate the probe arrays to room temperature immediately before use.
6. Fill the probe array with 1×MES Hyb Buffer, and incubate in the rotisserie oven for 10 minutes at 45° C., 60 rpm.
7. Heat the Hybridization Mix in a 99° C. waterbath for 5 minutes.
8. Transfer the Hybridization Mix to a 45° C. waterbath for 5 minutes.
9. Centrifuge the Hybridization Mix for 5 minutes at maximum speed.
10. Remove the 1×MES Hyb Buffer from the probe arrays.
11. Fill the probe array with the top 200 µl of the Hybridization Mix.
12. Seal the septa with Tough-Spots.
13. Hybridize the probe array at 45° C., 60 RPM for 19 hours.
14. Wash, stain and scan the probe array according to the Affymetrix protocols.

Affymetrix Materials

| Item | Vendor | Catalog # |
|---|---|---|
| T7-(dT)24 primer | Biosearch Technologies | custom |
| Control spikes | in-house | — |
| Superscript II/5X First Strand Buffer/0.1 M DTT | Invitrogen | 18064-014 |
| 5X Second Strand Buffer | Invitrogen | 10812-014 |
| 10 mM dNTP | Invitrogen | 18427-088 |
| 10 U/ul E. coli DNA Ligase | Invitrogen | 18052-019 |
| 10 U/ul E. coli DNA Polymerase I | Invitrogen | 18010-025 |
| 2 U/ul RNase H | Invitrogen | 18021-071 |
| 10 U/ul T4 DNA Polymerase | Invitrogen | 18005-025 |
| 0.5 M EDTA | Sigma | E-7889 |
| ENZO High Yield RNA Transcript labeling kit | Affymetrix or ENZO | 900182 (ENZO) |
| GeneChip Sample Cleanup Module | Affymetrix | 900371 |
| Acetylated Bovine Serum Albumin | Invitrogen | 15561-020 |
| Goat IgG - Reagent Grade | Sigma | I-5256 |
| Anti-streptavidin antibody (goat), biotinylated | Vector Labs | BA-0500 |
| R-Phycoerythrin Streptavidin | Molecular Probes | S-866 |
| 20X SSPE | BioWhittaker | 51214 |
| Eukaryotic Control Kit | Affymetrix | 900362 |
| Water, Molecular Biology Grade | Ambion | 9934 |
| Human Cot-1 DNA | Roche | 1-581-074 |
| 5 M NaCl RNase-free, DNase-free | Ambion | 9760 |
| Antifoam 0-30 | Sigma | A-8082 |
| 10% Tween-20 | Pierce Chemical | 28320 |
| MES Free Acid Monohydrate | Sigma | M5287 |
| MES Sodium Salt | Sigma | M3885 |
| EDTA Disodium Salt, 0.5 M solution | Sigma | E7889 |
| Tough Spots, Label Dots | USA Scientific | 9902 |
| GeneChip Hybridization Oven 640 | Affymetrix | 800139 |
| GeneChip Scanner 3000 w/Workstation | Affymetrix | 00-0074 |
| Fluidics Station | Affymetrix | 00-0081 |
| Autoloader w/External Barcode Reader | Affymetrix | 00-0129 |

Quantitative PCR

CDNA Synthesis:

| Component | Volume (uL) |
|---|---|
| 10X RT Buffer | 10 |
| 25X dNTP mixture | 4 |
| 10X Random Primers | 10 |
| MultiScribe RT (50 U/uL) | 5 |
| RNase-free H2O | 21 |
| RNA (100 ng) | 50 |
| Final Volume | 100 |

Incubation Conditions:

25° for 10 minutes

37° for 2 hours

TaqMan Reaction using the ABI Prism 7700 Sequencing Detector:

| Component | Volume (uL) |
|---|---|
| TaqMan Universal PCR Master Mix (2X) | 25 |
| TaqMan probe (20X) (Assays-on-Demand ™) | 2.5 |
| cDNA (100 ng) | 2 |
| H2O | 20.5 |
| Final Volume | 50 |

Thermal Cycling Conditions:

95° for 10 minutes 40 cycles: 95° for 15 seconds

60° for 1 minute

TaqMan probes: Assays-on-Demand™ (TaqMan® MGB probes, FAM™ dye-labeled)

Amplification of the endogenous control, GAPDH (probe concentration 100 nM, forward & reverse primer concentrations 200 nM), was performed to standardize the amount of sample RNA (cDNA) added to each reaction.

Relative quantitation was performed using the standard curve method. For quantitation normalized to an endogenous control, standard curves were prepared for both the target and the endogenous reference. For each experimental sample, the amount of target and endogenous reference was determined from the appropriate standard curve. Then, the target amount was divided by the endogenous reference amount to obtain a normalized target value. One of the experimental samples served as the calibrator, or 1× sample. Each of the normalized target values was then divided by the calibrator normalized target value to generate the relative expression levels.

FACS/Flow Cytometry (2° Antibody Staining Protocol):

All incubations and spins were performed at 4° C. and the tubes kept on ice while not in the refrigerator.

1. Determine the tube format by identifying the cell lines to be used, the antibodies of interest, and any special conditions or treatments.
   a. controls.
      i. Unstained, 2° Antibody, and compensation if the fluorochromes have overlapping emission spectra.
   b. Example:

| Tube | Cell Line | Time (min) | 1° Antibody | 2° Antibody |
|---|---|---|---|---|
| 1 | e.g., COLO-205 | 0 | — | — |
| 2 | e.g., COLO-205 | 0 | — | anti-Mouse-FITC |
| 3 | e.g., COLO-205 | 0 | anti-Sialyl Lewis A | anti-Mouse-FITC |
| 4 | e.g., COLO-205 | 0 | anti-CD15s (Sialyl Lewis X) | anti-Mouse-FITC |

2. Label the FACS tubes.
   a. BD Falcon 12×75 mm Polystyrene Round-Bottom. Catalog #: 352052
3. Prepare the cells for staining.
   a. Treat adherent cells with Accutase or Trypsin.
      i. Innovative Cell Technologies Inc, Accutase.
      ii. Gibco, Trypsin. Catalog #: 25200-106.
   b. Proceed with the remaining steps if the cells are suspension.
4. Aliquot the cells into a 15 mL or 50 mL conical tube.
5. Spin the cells for 5 min, 1200 rpm, 4° C.
6. Aspirate the supernatant.
7. Resuspend the cells in 5 mLs FACS Buffer.
8. Spin the cells for 5 min, 1200 rpm, 4° C.
9. Aspirate the supernatant.
10. Resuspend the cells in Blocking Buffer.
    a. Determine the volume of blocking buffer needed:
       i. Number of tubes per cell line/treatment X 100 µl Blocking Buffer per tube.
       ii. Want 1×10$^6$ cells per 100 µl of Blocking Buffer.
11. Aliquot 100 µl of the cells into the appropriate tube.
    a. Based on the pre-determined tube format.
12. Add the 1° antibody to the appropriate tube.
    a. Lewis A:
       i. Use 10 µl of 0.2 µg/µl stock per tube.
          1. Final concentration is 2 µg.
       ii. Chemicon: anti-Sialyl Lewis A. Catalog #: MAB2095.
    b. Lewis X:
       i. Use 5 µl of 0.5 µg/µl stock per tube.
          1. Final concentration is 2.5 µg.
       ii. BD Pharmingen: CD15s (Sialyl Lewis X). Catalog #: 551344.
13. Incubate for 30 min at 4° C.
14. Add 1 mL of FACS Buffer to each tube.
15. Spin the cells for 5 min, 1200 rpm, 4° C.
16. Aspirate the supernatant
17. Gently rack the tubes to dislodge the pellet.
    a. "Rack"-Run the tubes across the surface of the 12×75 mm tube rack.

18. Repeat steps 14-17.
19. Add 100 μl of Blocking Buffer to each tube.
20. Add the 2° antibody into the appropriate tube.
    a. Use 10 μl per tube.
    b. Jackson, Goat-anti-Mouse FITC. Catalog #: 115-096-068.
21. Incubate for 30 min at 4° C.
22. Repeat steps 14-17 twice.
23. Resuspend cells in FACS Buffer/PI.
    a. Determine volume needed:
        i. Need 1 mL of solution per tube.
        ii. PI=1 μl per 1 mL of Buffer.
    b. Molecular Probes, Propidium Iodide. Catalog #: P3566.
24. Place tubes in an ice bucket or iced tube rack.
25. Cover with aluminum foil and take to the FACS lab for a qualified operator to acquire and analyze samples.

5% Blocking Buffer:
1. FBS to 5% of total volume.
2. FACS Buffer.
3. Filter the solution through a 0.2 μm filter.

FACS Buffer:
1. 980 mLs PBS.
2. 8 mLs 0.25 M EDTA.
3. 20 mLs FBS.
4. Filter the solution through a 0.2 μm filter.

Immunohistochemistry Procedure: Sialyl Lewis A
Antibody: Sialyl Lewis A AB-1
Clone: 121SLE
Supplier: NeoMarkers
Catalog No. MS-279-P
Ig Species: Mouse
IHC Method: Paraffin
Pretreatment: None
IHC Handling: Autostainer
Isotype: Mouse IgM
Procedure Species: Human
IgG Concentration: 200 ug/ml Normal Procedure:
Deparaffinize and hydrate to distilled water.
Block endogenous biotin with Vector Avidin Biotin Blocking System.
Rinse with TBS: 2 changes, 5 minutes each.
Block with 10% Normal Horse Serum for 30 minutes at RT.
Incubate sections with Mouse Monoclonal Sialyl Lewis A antibody diluted to
5 ug/ml with 10% normal Horse Serum for 60 minutes at RT.
    Use a mouse isotype IgM diluted at 5 ug/ml in 10% Normal Horse Serum for the negative control.
Rinse with TBS: 2 changes, 5 minutes each.
Incubate sections with biotinylated horse anti-mouse antibody; 1:200
diluted in 10% Normal Horse Serum for 30 minutes at RT.
Rinse with TBS: 2 changes, 5 minutes each.
Incubate sections with diluted Vector ABC Elite System for 30 minutes at RT.
Rinse with TBS: 2 changes, 5 minutes each.
Incubate sections with Pierce Metal Enhanced DAB for 5 minutes
Rinse in Running Tap water for 5 minutes.
Counterstain with Mayers Hematoxylin for 1 minute.
Rinse in Running Tap water for 5 minutes.
Blue Hematoxylin with Richard-Allan Bluing Reagent for 1 minute.
Rinse in Running Tap water for 2 minutes.
Dehydrate, clear and mount in synthetic mounting media.

Immunohistochemistry Procedure: Sialyl Lewis X
Antibody: Mouse anti-Sialyl Lewis X
Clone: KM93
Supplier: Chemicon
Catalog No. MAB2096
Ig Species: Mouse
IHC Method: Paraffin
Pretreatment: DAKO Target Retrieval
IHC Handling: Autostainer
Isotype: Mouse IgM
Procedure Species: Human
IgG Concentration: 100 ug/ml Normal Procedure:
Deparaffinize and hydrate to distilled water.
Quench endogenous peroxidase activity with KPL Blocking Solution—dilute
concentrate 1:10 in dH2O, RT for 4 minutes.
Rinse in Distilled water for 5 minutes.
Incubate in DAKO Target Retrieval (S1700) preheated to 99 degrees for 20
minutes in a boiling water bath. Remove from boiling bath and let cool for 20 minutes.
Block endogenous biotin with Vector Avidin Biotin Blocking System.
Block with 10% Normal Horse Serum for 30 minutes at RT.
Incubate sections with Mouse Monoclonal Sialyl Lewis X antibody diluted to
5 μg/ml with 10% normal Horse Serum for 60 minutes at RT.
    Use a mouse isotype IgM diluted at 5 μg/ml in 10% Normal Horse Serum for the negative control.
Rinse with TBS: 2 changes, 5 minutes each.
Incubate sections with Vector biotinylated horse anti-mouse antibody;
1:200 diluted in 10% Normal Horse Serum for 30 minutes at RT.
Rinse with TBS: 2 changes, 5 minutes each.
Incubate sections with diluted Vector ABC Elite System for 30 minutes at RT.
Rinse with TBS: 2 changes, 5 minutes each.
Incubate sections with Pierce Metal Enhanced DAB for 5 minutes
Rinse in Running Tap water for 5 minutes.
Counterstain with Mayers Hematoxylin for 1 minute.
Rinse in Running Tap water for 5 minutes.
Blue Hematoxylin with Richard-Allan Bluing Reagent for 1 minute.
Rinse in Running Tap water for 2 minutes.
Dehydrate, clear and mount in synthetic mounting media.

Experimental Results:
Experiments were conducted using the methods and materials described above. Results of these experiments are illustrated in FIGS. 6-13, as discussed below.

FIG. 6 provides a summary chart of the data obtained in analyzing 28 colon or colorectal cancer cell lines for sensitivity or resistance to apoptotic activity of Apo2L (+0.5% fetal bovine serum "FBS" or 10% FBS) or DR5 monoclonal antibody "mab", cross-linked "XL" or not crosslinked, +0.5% fetal bovine serum "FBS" or 10% FBS) and expression of FUT 3, FUT 6, Sialyl lewis A and Sialyl lewis X.

FIG. 7 provides a comparison of sensitivity of various colon or colorectal cancer cell lines to DR5 antibody and the expression of FUT 3, as measured by quantitative PCR).

Figure 8:
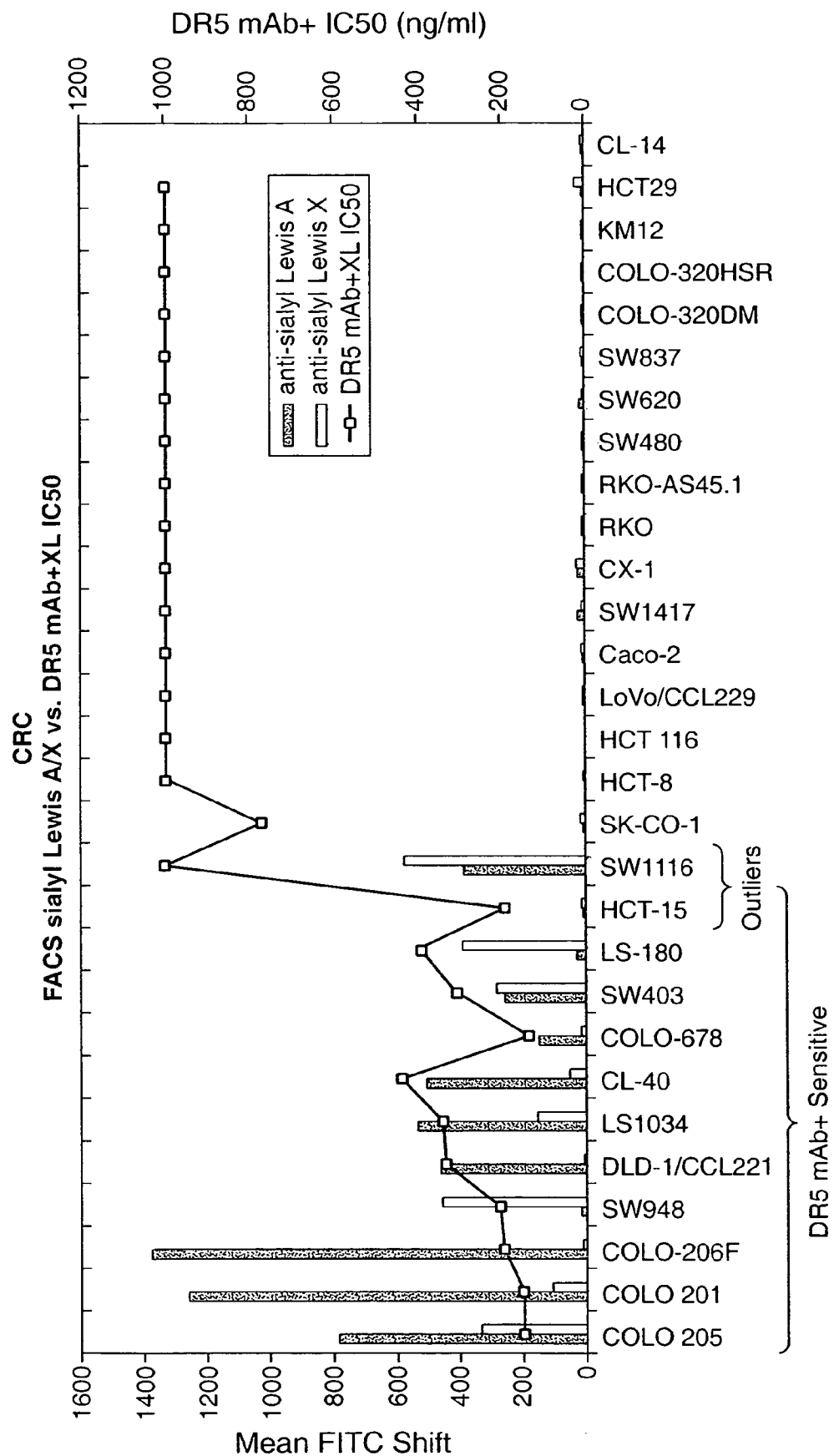
FIG. 8 provides a comparison of various colon or colorectal cancer cell lines for sensitivity or resistance to DR5 antibody (plus cross-linker) and expression of sialyl lewis X or A, as determined by FACS.

FIG. 8 provides a comparison of various colon or colorectal cancer cell lines for sensitivity or resistance to DR5 antibody (plus cross-linker) and expression of sialyl lewis X or A, as determined by FACS.

Figure 9A:
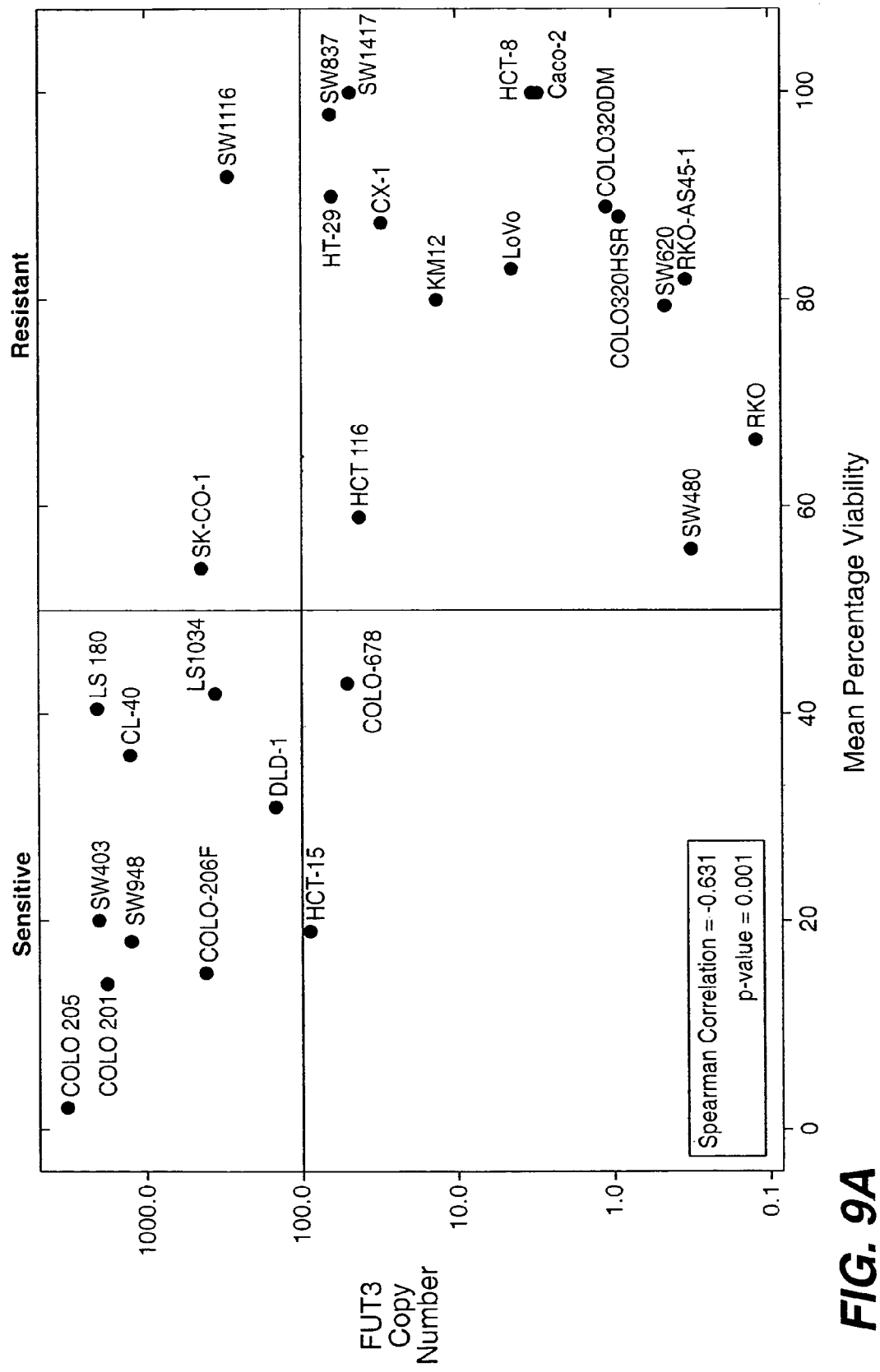
FIG. 9A shows a Spearman Rank Correlation test analyzing sensitivity or resistance of various colon or colorectal cancer cell lines and correlation to expression of FUT3.

FIG. 9A shows a Spearman Rank Correlation test analyzing sensitivity or resistance of various colon or colorectal cancer cell lines and correlation to expression of FUT3.

FIG. 9B shows the results of a Fisher's Exact test analyzing sensitivity ("sens") or resistance ("res") of the various colon or colorectal cancer cell lines and the statistical significance between FUT 3 and sialyl lewis A/X expression and sensitivity of the respective cell lines to DR5 antibody apoptotic activity.

FIG. 10 provides a comparison of various colon or colorectal cancer cell lines for expression of DcR1 or DcR2 receptors (as determined by quantitative PCR) and the status (sensitive or resistant) of certain cell lines to Apo2L or DR5 antibody.

FIG. 11 provides a comparison of various colon or colorectal cancer cell lines for expression of DcR1 or DcR2 receptors (as determined by FACS) and the status (sensitive or resistant) of certain cell lines to Apo2L or DR5 antibody.

FIG. 12 shows immunohistochemical staining for sialyl lewis A and X on four colorectal cancer cell lines, CaCo 2 (Colo2), SW 1417, DLD-1, and Colo 205, and its correlation to expression of sialyl Lewis A and X as measured by FACS and its correlation to sensitivity to Apo2L/TRAIL. Colorectal cancer cell lines Colo 2 and SW1417 show no and weak staining, respectively, or sialyl Lewis antigens, are negative and weakly positive, respectively, by FACS and are resistant to Apo2L/TRAIL. Colorectal cancer cells lines DLD-1 and Colo 205 show moderate and strong staining, respectively for sialyl Lewis antigens, are moderately and strongly positive, respectively, by FACS and are sensitive to Apo2L/TRAIL.

FIG. 13 shows a summary of IHC experiments demonstrating expression of sialyl Lewis A and X in tissue samples of normal colon mucosa, normal liver tissue, primary colon cancer, and colon cancer metastases. Tissue samples of normal colon and primary colon cancer arrayed in a tissue microarray were tested in the IHC experiment, while tissue samples of the normal liver and metastatic colon cancer were on individual glass slides. The prevalence of expression of sialyl Lewis A and X and the immunohistochemical staining intensity increases from normal colon tissue to primary colon cancer to metastatic colon cancer. The normal liver cells did not stain for for either sialyl Lewis A or X.

What is claimed is:

1. A method for inducing apoptosis in a mammalian tissue or cell sample, comprising the steps of:
    obtaining a mammalian tissue or cell sample;
    examining the tissue or cell sample to detect expression of one or more biomarkers selected from the group of fucosyltransferase 3, fucosyltransferase 6, sialyl Lewis A and/or X antigen(s), and
    subsequent to detecting expression of said one or more biomarkers, exposing said tissue or cell sample to an effective amount of Apo2L/TRAIL.

2. The method of claim 1 wherein said expression of one or more biomarkers is examined by testing for mRNA expression of fucosyltransferase 3 or fucosyltransferase 6.

3. The method of claim 1 wherein said expression of one or more biomarkers is examined by immunohistochemistry to detect expression of sialyl Lewis A and/or X antigen(s).

4. The method of claim 1 further comprising the step of examining expression of DR4, DR5, DcR1 or DcR2 receptors in said tissue or cell sample.

5. The method of claim 1 wherein said tissue or cell sample comprises cancer tissue or cells.

6. The method of claim 5 wherein said cancer cells are colon, colorectal, gastrointestinal, or pancreatic cancer cells or tissue.

7. The method of claim 1 wherein said cells are exposed to an effective amount of Apo2L/TRAIL polypeptide comprising amino acids 114-281 of FIG. 1 (SEQ ID NO:1).

8. The method of claim 1 wherein said Apo2L/TRAIL polypeptide is linked to a polyethylene glycol molecule.

9. The method of claim 6 wherein said cancer cells are colon or colorectal cancer cells.

10. A method for inducing apoptosis in mammalian colon or colorectal cancer cells, comprising the steps of:
    obtaining mammalian colon or colorectal cancer cells;
    examining the cancer cells to detect expression of one or more biomarkers selected from the group of fucosyltransferase 3, fucosyltransferase 6, sialyl Lewis A and/or X antigen(s), and subsequent to detecting expression of said one or more biomarkers, exposing said cancer cells to an effective amount of Apo2L/TRAIL polypeptide.

11. The method of claim 10 wherein said Apo2L/TRAIL polypeptide comprises amino acids 41-281 of FIG. 1 (SEQ ID NO:1) or a fragment thereof which has apoptotic activity.

12. The method of claim 11 wherein said Apo2L/TRAIL polypeptide is linked to a polyethylene glycol molecule.

13. The method of claim 11 wherein said Apo2L/TRAIL polypeptide comprises amino acids 114-281 of FIG. 1 (SEQ ID NO:1).

* * * * *

SEQUENCE LISTING

```
<160> NUMBER OF SEQ ID NOS: 14

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr
  1               5                  10                  15

Cys Val Leu Ile Val Ile Phe Thr Val Leu Leu Gln Ser Leu Cys
                 20                  25                  30

Val Ala Val Thr Tyr Val Tyr Phe Thr Asn Glu Leu Lys Gln Met
                 35                  40                  45

Gln Asp Lys Tyr Ser Lys Ser Gly Ile Ala Cys Phe Leu Lys Glu
                 50                  55                  60

Asp Asp Ser Tyr Trp Asp Pro Asn Asp Glu Glu Ser Met Asn Ser
                 65                  70                  75

Pro Cys Trp Gln Val Lys Trp Gln Leu Arg Gln Leu Val Arg Lys
                 80                  85                  90

Met Ile Leu Arg Thr Ser Glu Glu Thr Ile Ser Thr Val Gln Glu
                 95                 100                 105

Lys Gln Gln Asn Ile Ser Pro Leu Val Arg Glu Arg Gly Pro Gln
                110                 115                 120

Arg Val Ala Ala His Ile Thr Gly Thr Arg Gly Arg Ser Asn Thr
                125                 130                 135

Leu Ser Ser Pro Asn Ser Lys Asn Glu Lys Ala Leu Gly Arg Lys
                140                 145                 150

Ile Asn Ser Trp Glu Ser Ser Arg Ser Gly His Ser Phe Leu Ser
                155                 160                 165

Asn Leu His Leu Arg Asn Gly Glu Leu Val Ile His Glu Lys Gly
                170                 175                 180
```

-continued

```
Phe Tyr Tyr Ile Tyr Ser Gln Thr Tyr Arg Phe Gln Glu Glu
            185                 190                 195

Ile Lys Glu Asn Thr Lys Asn Asp Lys Gln Met Val Gln Tyr Ile
        200                 205                 210

Tyr Lys Tyr Thr Ser Tyr Pro Asp Pro Ile Leu Leu Met Lys Ser
            215                 220                 225

Ala Arg Asn Ser Cys Trp Ser Lys Asp Ala Glu Tyr Gly Leu Tyr
            230                 235                 240

Ser Ile Tyr Gln Gly Gly Ile Phe Glu Leu Lys Glu Asn Asp Arg
            245                 250                 255

Ile Phe Val Ser Val Thr Asn Glu His Leu Ile Asp Met Asp His
            260                 265                 270

Glu Ala Ser Phe Phe Gly Ala Phe Leu Val Gly
            275                 280
```

<210> SEQ ID NO 2
<211> LENGTH: 1042
<212> TYPE: DNA
<213> ORGANISM: Homo sapiens
<220> FEATURE:
<221> NAME/KEY: Unsure
<222> LOCATION: 447
<223> OTHER INFORMATION: Unknown base

<400> SEQUENCE: 2

```
tttcctcact gactataaaa gaatagagaa ggaagggctt cagtgaccgg          50
ctgcctggct gacttacagc agtcagactc tgacaggatc atggctatga         100
tggaggtcca gggggaccc agcctgggac agacctgcgt gctgatcgtg          150
atcttcacag tgctcctgca gtctctctgt gtggctgtaa cttacgtgta         200
ctttaccaac gagctgaagc agatgcagga caagtactcc aaaagtggca         250
ttgcttgttt cttaaaagaa gatgacagtt attgggaccc caatgacgaa         300
gagagtatga cagcccctg ctggcaagtc aagtggcaac tccgtcagct          350
cgttagaaag atgatttga gaacctctga ggaaaccatt tctacagttc          400
aagaaaagca acaaaatatt tctcccctag tgagagaaag aggtccncag         450
agagtagcag ctcacataac tgggaccaga ggaagaagca acacattgtc         500
ttctccaaac tccaagaatg aaaaggctct gggccgcaaa ataaactcct         550
gggaatcatc aaggagtggg cattcattcc tgagcaactt gcacttgagg         600
aatggtgaac tggtcatcca tgaaaagggg ttttactaca tctattccca         650
aacatacttt cgatttcagg aggaaataaa agaaaacaca aagaacgaca         700
aacaaatggt ccaatatatt tacaaataca caagttatcc tgaccctata         750
ttgttgatga aaagtgctag aaatagttgt tggtctaaag atgcagaata         800
tggactctat tccatctatc aagggggaat atttgagctt aaggaaaatg         850
acagaatttt tgtttctgta acaaatgagc acttgataga catggaccat         900
gaagccagtt ttttcggggc cttttagtt ggctaactga cctggaaaga         950
aaagcaata acctcaaagt gactattcag ttttcaggat gatacactat        1000
gaagatgttt caaaaatct gaccaaaaca aacaaacaga aa                 1042
```

<210> SEQ ID NO 3
<211> LENGTH: 468
<212> TYPE: PRT

<213> ORGANISM: Homo sapiens

<400> SEQUENCE: 3

```
Met Ala Pro Pro Pro Ala Arg Val His Leu Gly Ala Phe Leu Ala
 1               5                  10                  15

Val Thr Pro Asn Pro Gly Ser Ala Ala Ser Gly Thr Glu Ala Ala
                20                  25                  30

Ala Ala Thr Pro Ser Lys Val Trp Gly Ser Ala Gly Arg Ile
                35                  40                  45

Glu Pro Arg Gly Gly Gly Arg Gly Ala Leu Pro Thr Ser Met Gly
                50                  55                  60

Gln His Gly Pro Ser Ala Arg Ala Arg Ala Gly Arg Ala Pro Gly
                65                  70                  75

Pro Arg Pro Ala Arg Glu Ala Ser Pro Leu Arg Val His Lys
                80                  85                  90

Thr Phe Lys Phe Val Val Gly Val Leu Leu Gln Val Val Pro
                95                  100                 105

Ser Ser Ala Ala Thr Ile Lys Leu His Asp Gln Ser Ile Gly Thr
                110                 115                 120

Gln Gln Trp Glu His Ser Pro Leu Gly Glu Leu Cys Pro Pro Gly
                125                 130                 135

Ser His Arg Ser Glu Arg Pro Gly Ala Cys Asn Arg Cys Thr Glu
                140                 145                 150

Gly Val Gly Tyr Thr Asn Ala Ser Asn Asn Leu Phe Ala Cys Leu
                155                 160                 165

Pro Cys Thr Ala Cys Lys Ser Asp Glu Glu Glu Arg Ser Pro Cys
                170                 175                 180

Thr Thr Thr Arg Asn Thr Ala Cys Gln Cys Lys Pro Gly Thr Phe
                185                 190                 195

Arg Asn Asp Asn Ser Ala Glu Met Cys Arg Lys Cys Ser Thr Gly
                200                 205                 210

Cys Pro Arg Gly Met Val Lys Val Lys Asp Cys Thr Pro Trp Ser
                215                 220                 225

Asp Ile Glu Cys Val His Lys Glu Ser Gly Asn Gly His Asn Ile
                230                 235                 240

Trp Val Ile Leu Val Val Thr Leu Val Val Pro Leu Leu Leu Val
                245                 250                 255

Ala Val Leu Ile Val Cys Cys Cys Ile Gly Ser Gly Cys Gly Gly
                260                 265                 270

Asp Pro Lys Cys Met Asp Arg Val Cys Phe Trp Arg Leu Gly Leu
                275                 280                 285

Leu Arg Gly Pro Gly Ala Glu Asp Asn Ala His Asn Glu Ile Leu
                290                 295                 300

Ser Asn Ala Asp Ser Leu Ser Thr Phe Val Ser Glu Gln Gln Met
                305                 310                 315

Glu Ser Gln Glu Pro Ala Asp Leu Thr Gly Val Thr Val Gln Ser
                320                 325                 330

Pro Gly Glu Ala Gln Cys Leu Leu Gly Pro Ala Glu Ala Glu Gly
                335                 340                 345

Ser Gln Arg Arg Arg Leu Leu Val Pro Ala Asn Gly Ala Asp Pro
                350                 355                 360

Thr Glu Thr Leu Met Leu Phe Phe Asp Lys Phe Ala Asn Ile Val
                365                 370                 375
```

```
Pro Phe Asp Ser Trp Asp Gln Leu Met Arg Gln Leu Asp Leu Thr
            380                 385                 390
Lys Asn Glu Ile Asp Val Val Arg Ala Gly Thr Ala Gly Pro Gly
            395                 400                 405
Asp Ala Leu Tyr Ala Met Leu Met Lys Trp Val Asn Lys Thr Gly
            410                 415                 420
Arg Asn Ala Ser Ile His Thr Leu Leu Asp Ala Leu Glu Arg Met
            425                 430                 435
Glu Glu Arg His Ala Lys Glu Lys Ile Gln Asp Leu Leu Val Asp
            440                 445                 450
Ser Gly Lys Phe Ile Tyr Leu Glu Asp Gly Thr Gly Ser Ala Val
            455                 460                 465
Ser Leu Glu

<210> SEQ ID NO 4
<211> LENGTH: 1407
<212> TYPE: DNA
<213> ORGANISM: Homo sapiens

<400> SEQUENCE: 4
atggcgccac caccagctag agtacatcta ggtgcgttcc tggcagtgac          50
tccgaatccc gggagcgcag cgagtgggac agaggcagcc gcggccacac         100
ccagcaaagt gtggggctct ccgcggggga ggattgaacc acgaggcggg         150
ggccgaggag cgctccctac ctccatggga cagcacggac ccagtgcccg         200
ggcccgggca gggcgcgccc caggacccag gccggcgcgg aagccagcc          250 ctcggctccg ggtccacaag accttcaagt ttgtcgtcgt cggggtcctg         300
ctgcaggtcg tacctagctc agctgcaacc atgatcaatc aattggcaca         350
aattggcaca cagcaatggg aacatagccc tttgggagag ttgtgtccac         400
caggatctca tagatcagaa cgtcctggag cctgtaaccg gtgcacagag         450
ggtgtgggtt acaccaatgc ttccaacaat ttgtttgctt gcctcccatg         500
tacagcttgt aaatcagatg aagaagagag aagtccctgc accacgacca         550
ggaacacagc atgtcagtgc aaaccaggaa ctttccggaa tgacaattct         600
gctgagatgt gccggaagtg cagcacaggg tgccccagag ggatggtcaa         650
ggtcaaggat tgtacgccct ggagtgacat cgagtgtgtc acaaagaat           700 caggcaatgg acataatata tgggtgattt tggttgtgac tttggttgtt         750
ccgttgctgt tggtggctgt gctgattgtc tgttgttgca tcggctcagg         800
ttgtggaggg gacccccaagt gcatggacag ggtgtgtttc tggcgcttgg         850
gtctcctacg agggcctggg gctgaggaca atgctcacaa cgagattctg         900
agcaacgcag actcgctgtc cactttcgtc tctgagcagc aaatggaaag         950
ccaggagccg gcagatttga caggtgtcac tgtacagtcc ccaggggagg        1000
cacagtgtct gctgggaccg gcagaagctg aagggtctca gaggaggagg        1050
ctgctggttc cagcaaatgg tgctgacccc actgagactc tgatgctgtt        1100 cttttgacaag tttgcaaaca tcgtgccctt tgactcctgg gaccagctca        1150
tgaggcagct ggacctcacg aaaaatgaga tcgatgtggt cagagctggt        1200
acagcaggcc caggggatgc cttgtatgca atgctgatga aatgggtcaa        1250
caaaactgga cggaacgcct cgatccacac cctgctggat gccttggaga        1300
```

-continued

```
ggatggaaga gagacatgca aaagagaaga ttcaggacct cttggtggac      1350
tctggaaagt tcatctactt agaagatggc acaggctctg ccgtgtcctt      1400
ggagtga                                                     1407
```

<210> SEQ ID NO 5
<211> LENGTH: 411
<212> TYPE: PRT
<213> ORGANISM: Homo sapiens

<400> SEQUENCE: 5

```
Met Glu Gln Arg Gly Gln Asn Ala Pro Ala Ala Ser Gly Ala Arg
 1               5                  10                  15

Lys Arg His Gly Pro Gly Pro Arg Glu Ala Arg Gly Ala Arg Pro
                20                  25                  30

Gly Leu Arg Val Pro Lys Thr Leu Val Leu Val Val Ala Ala Val
                35                  40                  45

Leu Leu Leu Val Ser Ala Glu Ser Ala Leu Ile Thr Gln Gln Asp
                50                  55                  60

Leu Ala Pro Gln Gln Arg Ala Ala Pro Gln Gln Lys Arg Ser Ser
                65                  70                  75

Pro Ser Glu Gly Leu Cys Pro Pro Gly His His Ile Ser Glu Asp
                80                  85                  90

Gly Arg Asp Cys Ile Ser Cys Lys Tyr Gly Gln Asp Tyr Ser Thr
                95                 100                 105

His Trp Asn Asp Leu Leu Phe Cys Leu Arg Cys Thr Arg Cys Asp
               110                 115                 120

Ser Gly Glu Val Glu Leu Ser Pro Cys Thr Thr Thr Arg Asn Thr
               125                 130                 135

Val Cys Gln Cys Glu Glu Gly Thr Phe Arg Glu Glu Asp Ser Pro
               140                 145                 150

Glu Met Cys Arg Lys Cys Arg Thr Gly Cys Pro Arg Gly Met Val
               155                 160                 165

Lys Val Gly Asp Cys Thr Pro Trp Ser Asp Ile Glu Cys Val His
               170                 175                 180

Lys Glu Ser Gly Ile Ile Ile Gly Val Thr Val Ala Ala Val Val
               185                 190                 195

Leu Ile Val Ala Val Phe Val Cys Lys Ser Leu Leu Trp Lys Lys
               200                 205                 210

Val Leu Pro Tyr Leu Lys Gly Ile Cys Ser Gly Gly Gly Gly Asp
               215                 220                 225

Pro Glu Arg Val Asp Arg Ser Ser Gln Arg Pro Gly Ala Glu Asp
               230                 235                 240

Asn Val Leu Asn Glu Ile Val Ser Ile Leu Gln Pro Thr Gln Val
               245                 250                 255

Pro Glu Gln Glu Met Glu Val Gln Glu Pro Ala Glu Pro Thr Gly
               260                 265                 270

Val Asn Met Leu Ser Pro Gly Glu Ser Glu His Leu Leu Glu Pro
               275                 280                 285

Ala Glu Ala Glu Arg Ser Gln Arg Arg Arg Leu Leu Val Pro Ala
               290                 295                 300

Asn Glu Gly Asp Pro Thr Glu Thr Leu Arg Gln Cys Phe Asp Asp
               305                 310                 315

Phe Ala Asp Leu Val Pro Phe Asp Ser Trp Glu Pro Leu Met Arg
```

```
                    320                 325                 330
Lys Leu Gly Leu Met Asp Asn Glu Ile Lys Val Ala Lys Ala Glu
            335                 340                 345
Ala Ala Gly His Arg Asp Thr Leu Tyr Thr Met Leu Ile Lys Trp
        350                 355                 360
Val Asn Lys Thr Gly Arg Asp Ala Ser Val His Thr Leu Leu Asp
    365                 370                 375
Ala Leu Glu Thr Leu Gly Glu Arg Leu Ala Lys Gln Lys Ile Glu
380                 385                 390
Asp His Leu Leu Ser Ser Gly Lys Phe Met Tyr Leu Glu Gly Asn
            395                 400                 405
Ala Asp Ser Ala Leu Ser
            410

<210> SEQ ID NO 6
<211> LENGTH: 440
<212> TYPE: PRT
<213> ORGANISM: Homo sapiens

<400> SEQUENCE: 6

Met Glu Gln Arg Gly Gln Asn Ala Pro Ala Ala Ser Gly Ala Arg
 1               5                  10                  15
Lys Arg His Gly Pro Gly Pro Arg Glu Ala Arg Gly Ala Arg Pro
            20                  25                  30
Gly Pro Arg Val Pro Lys Thr Leu Val Leu Val Val Ala Ala Val
        35                  40                  45
Leu Leu Leu Val Ser Ala Glu Ser Ala Leu Ile Thr Gln Gln Asp
    50                  55                  60
Leu Ala Pro Gln Gln Arg Ala Ala Pro Gln Gln Lys Arg Ser Ser
65                  70                  75
Pro Ser Glu Gly Leu Cys Pro Pro Gly His His Ile Ser Glu Asp
            80                  85                  90
Gly Arg Asp Cys Ile Ser Cys Lys Tyr Gly Gln Asp Tyr Ser Thr
        95                  100                 105
His Trp Asn Asp Leu Leu Phe Cys Leu Arg Cys Thr Arg Cys Asp
        110                 115                 120
Ser Gly Glu Val Glu Leu Ser Pro Cys Thr Thr Thr Arg Asn Thr
        125                 130                 135
Val Cys Gln Cys Glu Glu Gly Thr Phe Arg Glu Glu Asp Ser Pro
        140                 145                 150
Glu Met Cys Arg Lys Cys Arg Thr Gly Cys Pro Arg Gly Met Val
        155                 160                 165
Lys Val Gly Asp Cys Thr Pro Trp Ser Asp Ile Glu Cys Val His
        170                 175                 180
Lys Glu Ser Gly Thr Lys His Ser Gly Glu Ala Pro Ala Val Glu
        185                 190                 195
Glu Thr Val Thr Ser Ser Pro Gly Thr Pro Ala Ser Pro Cys Ser
        200                 205                 210
Leu Ser Gly Ile Ile Ile Gly Val Thr Val Ala Ala Val Val Leu
        215                 220                 225
Ile Val Ala Val Phe Val Cys Lys Ser Leu Leu Trp Lys Lys Val
        230                 235                 240
Leu Pro Tyr Leu Lys Gly Ile Cys Ser Gly Gly Gly Gly Asp Pro
        245                 250                 255
```

```
Glu Arg Val Asp Arg Ser Ser Gln Arg Pro Gly Ala Glu Asp Asn
                260                 265                 270

Val Leu Asn Glu Ile Val Ser Ile Leu Gln Pro Thr Gln Val Pro
            275                 280                 285

Glu Gln Glu Met Glu Val Gln Glu Pro Ala Glu Pro Thr Gly Val
        290                 295                 300

Asn Met Leu Ser Pro Gly Glu Ser Glu His Leu Leu Glu Pro Ala
    305                 310                 315

Glu Ala Glu Arg Ser Gln Arg Arg Leu Leu Val Pro Ala Asn
320                 325                 330

Glu Gly Asp Pro Thr Glu Thr Leu Arg Gln Cys Phe Asp Asp Phe
            335                 340                 345

Ala Asp Leu Val Pro Phe Asp Ser Trp Glu Pro Leu Met Arg Lys
        350                 355                 360

Leu Gly Leu Met Asp Asn Glu Ile Lys Val Ala Lys Ala Glu Ala
    365                 370                 375

Ala Gly His Arg Asp Thr Leu Tyr Thr Met Leu Ile Lys Trp Val
380                 385                 390

Asn Lys Thr Gly Arg Asp Ala Ser Val His Thr Leu Leu Asp Ala
            395                 400                 405

Leu Glu Thr Leu Gly Glu Arg Leu Ala Lys Gln Lys Ile Glu Asp
        410                 415                 420

His Leu Leu Ser Ser Gly Lys Phe Met Tyr Leu Glu Gly Asn Ala
    425                 430                 435

Asp Ser Ala Met Ser
440

<210> SEQ ID NO 7
<211> LENGTH: 1180
<212> TYPE: DNA
<213> ORGANISM: Homo sapiens

<400> SEQUENCE: 7
gctgtgggaa cctctccacg cgcacgaact cagccaacga tttctgatag            50 attttttggga gtttgaccag agatgcaagg ggtgaaggag cgcttcctac           100
cgttagggaa ctctggggac agagcgcccc ggccgcctga tggccgaggc           150
agggtgcgac ccaggaccca ggacggcgtc gggaaccata ccatggcccg           200
gatccccaag accctaaagt tcgtcgtcgt catcgtcgcg gtcctgctgc           250
cagtcctagc ttactctgcc accactgccc ggcaggagga agttccccag           300
cagacagtgg ccccacagca acagaggcac agcttcaagg gggaggagtg           350
tccagcagga tctcatagat cagaacatac tggagcctgt aacccgtgca           400
cagagggtgt ggattacacc aacgcttcca caatgaacc ttcttgcttc           450 ccatgtacag tttgtaaatc agatcaaaaa cataaaagtt cctgcaccat           500
gaccagagac acagtgtgtc agtgtaaaga aggcaccttc cggaatgaaa           550
actccccaga gatgtgccgg aagtgtagca ggtgccctag tggggaagtc           600
caagtcagta attgtacgtc ctgggatgat atccagtgtg ttgaagaatt           650
tggtgccaat gccactgtgg aaaccccagc tgctgaagag acaatgaaca           700
ccagcccggg gactcctgcc ccagctgctg aagagacaat gaacaccagc           750
ccagggactc ctgccccagc tgctgaagag acaatgacca ccagcccggg           800
```

-continued

```
gactcctgcc ccagctgctg aagagacaat gaccaccagc ccggggactc        850
ctgccccagc tgctgaagag acaatgacca ccagcccggg gactcctgcc        900
tcttctcatt acctctcatg caccatcgta gggatcatag ttctaattgt        950
gcttctgatt gtgtttgttt gaaagacttc actgtggaag aaattccttc       1000
cttacctgaa aggttcaggt aggcgctggc tgagggcggg gggcgctgga       1050
cactctctgc cctgcctccc tctgctgtgt tcccacagac agaaacgcct       1100
gcccctgccc caaaaaaaaa aaaaaaaaaa aaaaaaaaaa aaaaaaaaaa       1150
aaaaaaaaaa aaaaaaaaaa aaaaaaaaaa                             1180
```

<210> SEQ ID NO 8
<211> LENGTH: 259
<212> TYPE: PRT
<213> ORGANISM: Homo sapiens

<400> SEQUENCE: 8

```
Met Ala Arg Ile Pro Lys Thr Leu Lys Phe Val Val Ile Val
  1               5                  10                  15

Ala Val Leu Leu Pro Val Leu Ala Tyr Ser Ala Thr Thr Ala Arg
                 20                  25                  30

Gln Glu Glu Val Pro Gln Gln Thr Val Ala Pro Gln Gln Arg
                 35                  40                  45

His Ser Phe Lys Gly Glu Glu Cys Pro Ala Gly Ser His Arg Ser
                 50                  55                  60

Glu His Thr Gly Ala Cys Asn Pro Cys Thr Glu Gly Val Asp Tyr
                 65                  70                  75

Thr Asn Ala Ser Asn Asn Glu Pro Ser Cys Phe Pro Cys Thr Val
                 80                  85                  90

Cys Lys Ser Asp Gln Lys His Lys Ser Ser Cys Thr Met Thr Arg
                 95                 100                 105

Asp Thr Val Cys Gln Cys Lys Glu Gly Thr Phe Arg Asn Glu Asn
                110                 115                 120

Ser Pro Glu Met Cys Arg Lys Cys Ser Arg Cys Pro Ser Gly Glu
                125                 130                 135

Val Gln Val Ser Asn Cys Thr Ser Trp Asp Asp Ile Gln Cys Val
                140                 145                 150

Glu Glu Phe Gly Ala Asn Ala Thr Val Glu Thr Pro Ala Ala Glu
                155                 160                 165

Glu Thr Met Asn Thr Ser Pro Gly Thr Pro Ala Pro Ala Ala Glu
                170                 175                 180

Glu Thr Met Asn Thr Ser Pro Gly Thr Pro Ala Pro Ala Ala Glu
                185                 190                 195

Glu Thr Met Thr Thr Ser Pro Gly Thr Pro Ala Pro Ala Ala Glu
                200                 205                 210

Glu Thr Met Thr Thr Ser Pro Gly Thr Pro Ala Pro Ala Ala Glu
                215                 220                 225

Glu Thr Met Thr Thr Ser Pro Gly Thr Pro Ala Ser Ser His Tyr
                230                 235                 240

Leu Ser Cys Thr Ile Val Gly Ile Ile Val Leu Ile Val Leu Leu
                245                 250                 255

Ile Val Phe Val
```

<210> SEQ ID NO 9

<211> LENGTH: 2082
<212> TYPE: DNA
<213> ORGANISM: Homo sapiens

<400> SEQUENCE: 9

```
ccaactgcac ctcggttcta tcgattgaat tccccgggga tcctctagag         50
atccctcgac ctcgacccac gcgtccggaa cctttgcacg cgcacaaact        100
acggggacga tttctgattg attttttggcg ctttcgatcc accctcctcc      150
cttctcatgg gactttgggg acaaagcgtc ccgaccgcct cgagcgctcg        200
agcagggcgc tatccaggag ccaggacagc gtcgggaacc agaccatggc        250
tcctggaccc caagatcctt aagttcgtcg tcttcatcgt cgcggttctg        300
ctgccggtcc gggttgactc tgccaccatc ccccggcagg acgaagttcc        350
ccagcagaca gtggccccac agcaacagag gcgcagcctc aaggaggagg        400
agtgtccagc aggatctcat agatcagaat atactggagc tgtaaccccg        450
tgcacagagg gtgtggatta ccattgct tccaacaatt tgccttcttg          500
cctgctatgt acagtttgta atcaggtca acaaataaa agttcctgta          550
ccacgaccag agacaccgtg tgtcagtgtg aaaaggaag cttccaggat          600
aaaaactccc ctgagatgtg ccggacgtgt agaacagggt gtcccagagg        650
gatggtcaag gtcagtaatt gtacgccccg gagtgacatc aagtgcaaaa        700
atgaatcagc tgccagttcc actgggaaaa ccccagcagc ggaggagaca        750
gtgaccacca tcctggggat gcttgcctct ccctatcact accttatcat        800
catagtggtt ttagtcatca ttttagctgt ggttgtggtt ggcttttcat        850
gtcggaagaa attcatttct tacctcaaag gcatctgctc aggtggtgga        900
ggaggtcccg aacgtgtgca cagagtcctt ttccggcggc gttcatgtcc        950
ttcacgagtt cctggggcgg aggacaatgc ccgcaacgag accctgagta       1000
acagatactt gcagcccacc caggtctctg agcaggaaat ccaaggtcag       1050
gagctggcag agctaacagg tgtgactgta gagtygccag aggagccaca       1100
gcgtctgctg gaacaggcag aagctgaagg gtgtcagagg aggaggctgc       1150
tggttccagt gaatgacgct gactccgctg acatcagcac cttgctggat       1200
gcctcggcaa cactggaaga aggacatgca aaggaaacaa ttcaggacca       1250
actggtgggc tccgaaaagc tcttttatga agaagatgag gcaggctctg       1300
ctacgtcctg cctgtgaaag aatctcttca ggaaaccaga gcttccctca       1350
tttacctttt ctcctacaaa gggaagcagc ctggaagaaa cagtccagta       1400
cttgacccat gccccaacaa actctactat ccaatatggg gcagcttacc       1450
aatggtccta gaactttgtt aacgcacttg gagtaatttt tatgaaatac       1500
tgcgtgtgat aagcaaacgg gagaaattta tatcagattc ttggctgcat       1550
agttatacga ttgtgtatta agggtcgttt taggccacat gcggtggctc       1600
atgcctgtaa tcccagcact tgataggct gaggcaggtg gattgcttga        1650
gctcgggagt ttgagaccag cctcatcaac acagtgaaac tccatctcaa       1700
tttaaaaaga aaaaaagtgg ttttaggatg tcattctttg cagttcttca       1750
tcatgagaca agtctttttt tctgcttctt atattgcaag ctccatctct       1800
actggtgtgt gcatttaatg acatctaact acagatgccg cacagccaca       1850
```

```
atgctttgcc ttatagtttt ttaactttag aacgggatta tcttgttatt          1900
acctgtattt tcagtttcgg atattttga cttaatgatg agattatcaa           1950
gacgtacccc tatgctaagt catgagcata tggacttacg agggttcgac          2000
ttagagtttt gagctttaag ataggattat tgggggctta cccccacctt          2050
aattagaaga aacattttat attgctttac ta                             2082
```

```
<210> SEQ ID NO 10
<211> LENGTH: 386
<212> TYPE: PRT
<213> ORGANISM: Homo sapiens
<220> FEATURE:
<221> NAME/KEY: Unsure
<222> LOCATION: 310
<223> OTHER INFORMATION: Unknown amino acid

<400> SEQUENCE: 10
```

```
Met Gly Leu Trp Gly Gln Ser Val Pro Thr Ala Ser Ser Ala Arg
 1               5                  10                  15

Ala Gly Arg Tyr Pro Gly Ala Arg Thr Ala Ser Gly Thr Arg Pro
            20                  25                  30

Trp Leu Leu Asp Pro Lys Ile Leu Lys Phe Val Val Phe Ile Val
            35                  40                  45

Ala Val Leu Leu Pro Val Arg Val Asp Ser Ala Thr Ile Pro Arg
            50                  55                  60

Gln Asp Glu Val Pro Gln Gln Thr Val Ala Pro Gln Gln Gln Arg
        65                  70                  75

Arg Ser Leu Lys Glu Glu Glu Cys Pro Ala Gly Ser His Arg Ser
            80                  85                  90

Glu Tyr Thr Gly Ala Cys Asn Pro Cys Thr Glu Gly Val Asp Tyr
            95                 100                 105

Thr Ile Ala Ser Asn Asn Leu Pro Ser Cys Leu Leu Cys Thr Val
           110                 115                 120

Cys Lys Ser Gly Gln Thr Asn Lys Ser Ser Cys Thr Thr Thr Arg
           125                 130                 135

Asp Thr Val Cys Gln Cys Glu Lys Gly Ser Phe Gln Asp Lys Asn
           140                 145                 150

Ser Pro Glu Met Cys Arg Thr Cys Arg Thr Gly Cys Pro Arg Gly
           155                 160                 165

Met Val Lys Val Ser Asn Cys Thr Pro Arg Ser Asp Ile Lys Cys
           170                 175                 180

Lys Asn Glu Ser Ala Ala Ser Ser Thr Gly Lys Thr Pro Ala Ala
           185                 190                 195

Glu Glu Thr Val Thr Thr Ile Leu Gly Met Leu Ala Ser Pro Tyr
           200                 205                 210

His Tyr Leu Ile Ile Ile Val Val Leu Val Ile Ile Leu Ala Val
           215                 220                 225

Val Val Val Gly Phe Ser Cys Arg Lys Lys Phe Ile Ser Tyr Leu
           230                 235                 240

Lys Gly Ile Cys Ser Gly Gly Gly Gly Pro Glu Arg Val His
           245                 250                 255

Arg Val Leu Phe Arg Arg Arg Ser Cys Pro Ser Arg Val Pro Gly
           260                 265                 270

Ala Glu Asp Asn Ala Arg Asn Glu Thr Leu Ser Asn Arg Tyr Leu
           275                 280                 285
```

```
Gln Pro Thr Gln Val Ser Glu Gln Glu Ile Gln Gly Gln Glu Leu
                290                 295                 300

Ala Glu Leu Thr Gly Val Thr Val Glu Xaa Pro Glu Glu Pro Gln
            305                 310                 315

Arg Leu Leu Glu Gln Ala Glu Ala Glu Gly Cys Gln Arg Arg Arg
        320                 325                 330

Leu Leu Val Pro Val Asn Asp Ala Asp Ser Ala Asp Ile Ser Thr
                335                 340                 345

Leu Leu Asp Ala Ser Ala Thr Leu Glu Glu Gly His Ala Lys Glu
                350                 355                 360

Thr Ile Gln Asp Gln Leu Val Gly Ser Glu Lys Leu Phe Tyr Glu
                365                 370                 375

Glu Asp Glu Ala Gly Ser Ala Thr Ser Cys Leu
                380                 385

<210> SEQ ID NO 11
<211> LENGTH: 1086
<212> TYPE: DNA
<213> ORGANISM: Homo sapiens

<400> SEQUENCE: 11
atggatcccc tgggtgcagc caagccacaa tggccatggc ccgctgtct         50 ggccgcactg ctatttcagc tgctggtggc tgtgtgtttc ttctcctacc        100
tgcgtgtgtc ccgagacgat gccactggat cccctagggc tcccagtggg        150
tcctcccgac aggacaccac tcccacccgc ccaccctcc tgatcctgct         200 atggacatgg cctttccaca tccctgtggc tctgtcccgc tgttcagaga        250
tggtgcccgg cacagccgac tgccacatca ctgccgaccg caaggtgtac        300
ccacaggcag acacggtcat cgtgcaccac tgggatatca tgtccaaccc        350
taagtcacgc ctcccacctt ccccgaggcc gcaggggcag cgctggatct        400
ggttcaactt ggagccaccc cctaactgcc agcacctgga agccctggac        450
agatacttca atctcaccat gtcctaccgc agcgactccg acatcttcac        500
gccctacggc tggctggagc cgtggtccgg ccagcctgcc cacccaccgc        550
tcaacctctc ggccaagacc gagctggtgg cctgggcggt gtccaactgg        600
aagccggact cagccagggt gcgctactac cagagcctgc aggctcatct        650
caaggtggac gtgtacggac gctcccacaa gcccctgccc aaggggacca        700
tgatggagac gctgtcccgg tacaagttct acctggcctt cgagaactcc        750
ttgcaccccg actacatcac cgagaagctg tggaggaacg ccctggaggc        800
ctgggccgtg cccgtggtgc tgggcccag cagaagcaac tacgagaggt         850
tcctgccacc cgacgccttc atccacgtgg acgacttcca gagccccaag        900
gacctggccc ggtacctgca ggagctggac aaggaccacg cccgctacct        950
gagctacttt cgctggcggg agacgctgcg gcctcgctcc ttcagctggg       1000
cactggattt ctgcaaggcc tgctggaaac tgcagcagga atccaggtac       1050
cagacggtgc gcagcatagc ggcttggttc acctga                     1086

<210> SEQ ID NO 12
<211> LENGTH: 361
<212> TYPE: PRT
<213> ORGANISM: Homo sapiens
```

<400> SEQUENCE: 12

```
Met Asp Pro Leu Gly Ala Ala Lys Pro Gln Trp Pro Trp Arg Arg
1               5                   10                  15

Cys Leu Ala Ala Leu Leu Phe Gln Leu Val Ala Val Cys Phe
            20                  25                  30

Phe Ser Tyr Leu Arg Val Ser Arg Asp Asp Ala Thr Gly Ser Pro
                35                  40                  45

Arg Ala Pro Ser Gly Ser Ser Arg Gln Asp Thr Thr Pro Thr Arg
            50                  55                  60

Pro Thr Leu Leu Ile Leu Leu Trp Thr Trp Pro Phe His Ile Pro
                65                  70                  75

Val Ala Leu Ser Arg Cys Ser Glu Met Val Pro Gly Thr Ala Asp
            80                  85                  90

Cys His Ile Thr Ala Asp Arg Lys Val Tyr Pro Gln Ala Asp Thr
                95                  100                 105

Val Ile Val His His Trp Asp Ile Met Ser Asn Pro Lys Ser Arg
            110                 115                 120

Leu Pro Pro Ser Pro Arg Pro Gln Gly Gln Arg Trp Ile Trp Phe
                125                 130                 135

Asn Leu Glu Pro Pro Asn Cys Gln His Leu Glu Ala Leu Asp
            140                 145                 150

Arg Tyr Phe Asn Leu Thr Met Ser Tyr Arg Ser Asp Ser Asp Ile
                155                 160                 165

Phe Thr Pro Tyr Gly Trp Leu Glu Pro Trp Ser Gly Gln Pro Ala
            170                 175                 180

His Pro Pro Leu Asn Leu Ser Ala Lys Thr Glu Leu Val Ala Trp
                185                 190                 195

Ala Val Ser Asn Trp Lys Pro Asp Ser Ala Arg Val Arg Tyr Tyr
            200                 205                 210

Gln Ser Leu Gln Ala His Leu Lys Val Asp Val Tyr Gly Arg Ser
                215                 220                 225

His Lys Pro Leu Pro Lys Gly Thr Met Met Glu Thr Leu Ser Arg
            230                 235                 240

Tyr Lys Phe Tyr Leu Ala Phe Glu Asn Ser Leu His Pro Asp Tyr
                245                 250                 255

Ile Thr Glu Lys Leu Trp Arg Asn Ala Leu Glu Ala Trp Ala Val
            260                 265                 270

Pro Val Val Leu Gly Pro Ser Arg Ser Asn Tyr Glu Arg Phe Leu
                275                 280                 285

Pro Pro Asp Ala Phe Ile His Val Asp Asp Phe Gln Ser Pro Lys
            290                 295                 300

Asp Leu Ala Arg Tyr Leu Gln Glu Leu Asp Lys Asp His Ala Arg
                305                 310                 315

Tyr Leu Ser Tyr Phe Arg Trp Arg Glu Thr Leu Arg Pro Arg Ser
            320                 325                 330

Phe Ser Trp Ala Leu Asp Phe Cys Lys Ala Cys Trp Lys Leu Gln
                335                 340                 345

Gln Glu Ser Arg Tyr Gln Thr Val Arg Ser Ile Ala Ala Trp Phe
            350                 355                 360

Thr
```

<210> SEQ ID NO 13

<211> LENGTH: 1080
<212> TYPE: DNA
<213> ORGANISM: Homo sapiens

<400> SEQUENCE: 13

| | |
|---|---:|
| atggatcccc tgggcccggc caagccacag tggtcgtggc gctgctgtct | 50 |
| gaccacgctg ctgtttcagc tgctgatggc tgtgtgtttc ttctcctatc | 100 |
| tgcgtgtgtc tcaagacgat cccactgtgt accctaatgg gtcccgcttc | 150 |
| ccagacagca cagggacccc cgcccactcc atcccctga tcctgctgtg | 200 |
| gacgtggcct tttaacaaac ccatagctct gccccgctgc tcagagatgg | 250 |
| tgcctggcac ggctgactgc aacatcactg ccgaccgcaa ggtgtatcca | 300 |
| caggcagacg cggtcatcgt gcaccaccga gaggtcatgt acaacccag | 350 |
| tgcccagctc ccacgctccc cgaggcggca ggggcagcga tggatctggt | 400 |
| tcagcatgga gtccccaagc cactgctggc agctgaaagc catggacgga | 450 |
| tacttcaatc tcaccatgtc ctaccgcagc gactccgaca tcttcacgcc | 500 |
| ctacggctgg ctggagccgt ggtccggcca gcctgcccac ccaccgctca | 550 |
| acctctcggc caagaccgag ctggtggcct gggcagtgtc caactggggg | 600 |
| ccaaactccg ccagggtgcg ctactaccag agcctgcagg cccatctcaa | 650 |
| ggtggacgtg tacggacgct cccacaagcc cctgccccag ggaaccatga | 700 |
| tggagacgct gtcccggtac aagttctatc tggccttcga gaactccttg | 750 |
| caccccgact acatcaccga gaagctgtgg aggaacgccc tggaggcctg | 800 |
| ggccgtgccc gtggtgctgg gccccagcag aagcaactac gagaggttcc | 850 |
| tgccacccga cgccttcatc cacgtggacg acttccagag ccccaaggac | 900 |
| ctggcccggt acctgcagga gctggacaag gaccacgccc gctacctgag | 950 |
| ctactttcgc tggcgggaga cgctgcggcc tcgctccttc agctgggcac | 1000 |
| tcgctttctg caaggcctgc tggaaactgc aggaggaatc caggtaccag | 1050 |
| acacgcggca tagcggcttg gttcacctga | 1080 |

<210> SEQ ID NO 14
<211> LENGTH: 359
<212> TYPE: PRT
<213> ORGANISM: Homo sapiens

<400> SEQUENCE: 14

Met Asp Pro Leu Gly Pro Ala Lys Pro Gln Trp Ser Trp Arg Cys
1               5                   10                  15

Cys Leu Thr Thr Leu Leu Phe Gln Leu Leu Met Ala Val Cys Phe
                20                  25                  30

Phe Ser Tyr Leu Arg Val Ser Gln Asp Asp Pro Thr Val Tyr Pro
                35                  40                  45

Asn Gly Ser Arg Phe Pro Asp Ser Thr Gly Thr Pro Ala His Ser
                50                  55                  60

Ile Pro Leu Ile Leu Leu Trp Thr Trp Pro Phe Asn Lys Pro Ile
                65                  70                  75

Ala Leu Pro Arg Cys Ser Glu Met Val Pro Gly Thr Ala Asp Cys
                80                  85                  90

Asn Ile Thr Ala Asp Arg Lys Val Tyr Pro Gln Ala Asp Ala Val
                95                  100                 105

-continued

```
Ile Val His His Arg Glu Val Met Tyr Asn Pro Ser Ala Gln Leu
            110                 115                 120

Pro Arg Ser Pro Arg Arg Gln Gly Gln Arg Trp Ile Trp Phe Ser
            125                 130                 135

Met Glu Ser Pro Ser His Cys Trp Gln Leu Lys Ala Met Asp Gly
            140                 145                 150

Tyr Phe Asn Leu Thr Met Ser Tyr Arg Ser Asp Ser Asp Ile Phe
            155                 160                 165

Thr Pro Tyr Gly Trp Leu Glu Pro Trp Ser Gly Gln Pro Ala His
            170                 175                 180

Pro Pro Leu Asn Leu Ser Ala Lys Thr Glu Leu Val Ala Trp Ala
            185                 190                 195

Val Ser Asn Trp Gly Pro Asn Ser Ala Arg Val Arg Tyr Tyr Gln
            200                 205                 210

Ser Leu Gln Ala His Leu Lys Val Asp Val Tyr Gly Arg Ser His
            215                 220                 225

Lys Pro Leu Pro Gln Gly Thr Met Met Glu Thr Leu Ser Arg Tyr
            230                 235                 240

Lys Phe Tyr Leu Ala Phe Glu Asn Ser Leu His Pro Asp Tyr Ile
            245                 250                 255

Thr Glu Lys Leu Trp Arg Asn Ala Leu Glu Ala Trp Ala Val Pro
            260                 265                 270

Val Val Leu Gly Pro Ser Arg Ser Asn Tyr Glu Arg Phe Leu Pro
            275                 280                 285

Pro Asp Ala Phe Ile His Val Asp Asp Phe Gln Ser Pro Lys Asp
            290                 295                 300

Leu Ala Arg Tyr Leu Gln Glu Leu Asp Lys Asp His Ala Arg Tyr
            305                 310                 315

Leu Ser Tyr Phe Arg Trp Arg Glu Thr Leu Arg Pro Arg Ser Phe
            320                 325                 330

Ser Trp Ala Leu Ala Phe Cys Lys Ala Cys Trp Lys Leu Gln Glu
            335                 340                 345

Glu Ser Arg Tyr Gln Thr Arg Gly Ile Ala Ala Trp Phe Thr
            350                 355
```